(12) United States Patent
Ye et al.

(10) Patent No.: US 6,387,677 B1
(45) Date of Patent: May 14, 2002

(54) NUCLEIC ACID MOLECULES ENCODING HUMAN CALCIUM/CALMODULIN (CAMK) DEPENDENT KINASE PROTEINS

(75) Inventors: Jane Ye; Chunhua Yan, both of Boyds; Valentina Di Francesco, Rockville; Ellen M. Beasley, Darnestown, all of MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/800,960

(22) Filed: Mar. 8, 2001

(51) Int. Cl.[7] .......................... C12N 9/12; C12N 15/00; C12Q 1/48; C12P 21/06; C07K 1/00
(52) U.S. Cl. ........................ 435/194; 536/23.2; 435/15; 435/69.1; 435/325; 435/252.3; 435/320.1; 530/350
(58) Field of Search .......................... 435/194, 6, 320.1, 435/252.3, 325; 536/23.2; 436/94

(56) References Cited

PUBLICATIONS

Breen, M. A., and Ashcroft, S. J. H., (1997) Biochem. Biophys. Res. Commun. (1997) 236, 473–478; TrEMBL accession No. O15378, Jan. 5, 1998.*

Urquidi, V., and Ashcroft, S. J. H., (1995) FEBS Lett. 358, 23–26; TrEMBL accession No. Q63094, Nov. 1, 1996.*

Breen, M. A., and Ashcroft, S. J. H., (1997) Biochem. Res. Commun. (1997) 236, 473–478; TrEMBL accession No. O15378, Jan. 5, 1998.*

Sambrook and Russell, Molecular Cloning: A Laboratory Manual, CSHL Press, Third Edition, 2001.*

Breen, M. A., and Ashcroft, S. J. H., (1997) Biochem. Biophys. Res. Commun. (1997) 236, 473–478; TrEMBL accession No. O15378, Jan. 5, 1998.*

\* cited by examiner

*Primary Examiner*—Ponnathapu Achutamurthy
*Assistant Examiner*—Della M. Ramirez
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifing orthologs and paralogs of the kinase peptides, and methods of identifying modulators of the kinase peptides.

10 Claims, 35 Drawing Sheets

```
   1 CGGTGCTGCC GGGCTCAGCC CCGTCTCCTC CTCTTGCTCC CTCGGCCGGG
  51 CGGCGGTGAC TGTGCACCGA CGTCGGCGCG GGCTGCACCG CCGCGTCCGC
 101 CCGCCCGCCA GCATGGCCAC CACCGCCACC TGCACCCGTT TCACCGACGA
 151 CTACCAGCTC TTCGAGGAGC TTGGCAAGGG TGCTTTCTCT GTGGTCCGCA
 201 GGTGTGTGAA GAAAACCTCC ACGCAGGAGT ACGCAGCAAA AATCATCAAT
 251 ACCAAGAAAT TGTCTGCCCG GGATCACCAG AAACTAGAAC GTGAGGCTCG
 301 GATATGTCGA CTTCTGAAAC ATCCAAACAT CGTGCGCCTC CATGACAGTA
 351 TTTCTGAAGA AGGGTTTCAC TACCTCGTGT TTGACCTTGT TACCGGCGGG
 401 GAGCTGTTTG AAGACATTGT GGCCAGAGAG TACTACAGTG AAGCAGATGC
 451 CAGCCACTGT ATACATCAGA TTCTGGAGAG TGTTAACCAC ATCCACCAGC
 501 ATGACATCGT CCACAGGGAC CTGAAGCCTG AGAACCTGCT GCTGGCGAGT
 551 AAATGCAAGG GTGCCGCCGT CAAGCTGGCT GATTTTGGCC TAGCCATCGA
 601 AGTACAGGGA GAGCAGCAGG CTTGGTTTGG TTTTGCTGGC ACCCCAGGTT
 651 ACTTGTCCCC TGAGGTCTTG AGGAAAGATC CCTATGGAAA ACCTGTGGAT
 701 ATCTGGGCCT GCGGGGTCAT CCTGTATATC CTCCTGGTGG CTATCCTCC
 751 CTTCTGGGAT GAGGATCAGC ACAAGCTGTA TCAGCAGATC AAGGCTGGAG
 801 CCTATGATTT CCCCATCACC AGAATGGGACA CGGTAACTCC TGAAGCCAAG
 851 AACTTGATCA ACCAGATGCT GACCATAAAC CCAGCAAAGC GCATCACGGC
 901 TGACCAGGCT CTCAAGCACC CGTGGGTCTG TCAACGATCC ACGGTGGCAT
 951 CCATGATGCA TCGTCAGGAG ACTGTGGAGT GTTTGCGCAA GTTCAATGCC
1001 CGGAGAAAAC TGAAGGGTGC CATCCTCACG ACCATGCTTG TCTCCAGGAA
1051 CTTCTCAGTT GGCAGGCAGA GCTCCGCCCC CGCCTCGCCT GCCGCGAGCG
1101 CCGCCGGCCT GGCCGGGCAA GCTGCCAAAA GCCTATTGAA CAAGAAGTCG
1151 GATGGCGGTG TCAAGAAAAG GAAGTCGAGT CCAGCGTGC ACCTAATGGA
1201 GCCACAAACC ACTGTGGTAC ACAACGCTAC AGATGGGATC AAGGGCTCCA
1251 CAGAGAGCTG CAACACCACC ACAGAAGATG AGGACCTCAA AGCTGCCCCG
1301 CTCCGCACTG GGAATGGCAG CTCGGTGCCT GAAGGACGGA GCTCCCGGGA
1351 CAGAACAGCC CCCTCTGCAG GCATGCAGCC CCAGCCTTCT CTCTGCTCCT
1401 CAGCCATGCG AAAACAGGAG ATCATTAAGA TTACAGAACA GCTGATTGAA
1451 GCCATCAACA ATGGGGACTT TGAGGCCTAC ACGAAGATTT GTGATCCAGG
1501 CCTCACTTCC TTTGAGCCTG AGGCCCTTGG TAACCTCGTG GAGGGGATGG
1551 ATTTCCATAA GTTTTACTTT GAGAATCTCC TGTCCAAGAA CAGCAAGCCT
1601 ATCCATACCA CCATCCTAAA CCCACACGTC CACGTGATTG GGGAGGACGC
1651 AGCGTGCATC GCCTACATCC GCCTCACCCA GTACATCGAC GGGCAGGGTC
1701 GGCCTCGCAC CAGCCAGTCA GAAGAGACCC GGGTCTGGCA CCGTCGGGAT
1751 GGCAAGTGGC TCAATGTCCA CTATCACTGC TCAGGGGCCC CTGCCGCACC
1801 GCTGCAGTGA GCTCAGCCAC AGGGGCTTTA GGAGATTCCA GCCGGAGGTC
1851 CAACCTTCGC AGCCAGTGGC TCTGGAGGGC CTGAGTGACA GCGGCAGTCC
1901 TGTTTGTTTG AGGTTTAAAA CAATTCAATT ACAAAAGCGG CAGCAGCCAA
1951 TGCACGCCCC TGCATGCAGC CCTCCCGCCC GCCCTTCGTG TCTGTCTCTG
2001 CTGTACCGAG GTGTTTTTTA CATTTAAGAA AAAAAAAAA AAAAAAAAA
2051 AAAAAAAAAA A   (SEQ ID NO:1)
```

FEATURES:
5'UTR:       1-112
Start Codon: 113
Stop Codon:  1808
3'UTR:       1811

FIGURE 1A

```
Homologous proteins:
Top 10 BLAST Hits
                                                                      Score    E
CRA|88000001156376  /altid=gi|7434378  /def=pir||JC5636 Ca2+/calm...   1083   0.0
CRA|18000004937293  /altid=gi|125289   /def=sp|P11730|KCCG_RAT CAL...  1066   0.0
CRA|18000005054755  /altid=gi|1657464  /def=gb|AAC48714.1| (U7297...   1038   0.0
CRA|105000014644765 /altid=gi|10443740 /def=gb|AAG17558.1|AF233...      994   0.0
CRA|105000014644764 /altid=gi|10443738 /def=gb|AAG17557.1|AF233...      989   0.0
CRA|18000004903800  /altid=gi|422770   /def=pir||A46619 Ca2+/calmo...   986   0.0
CRA|18000005152785  /altid=gi|3241847  /def=dbj|BAA28869.1| (D149...    986   0.0
CRA|18000004937876  /altid=gi|631810   /def=pir||S43845 Ca2+/calmo...   985   0.0
CRA|18000004937877  /altid=gi|560653   /def=gb|AAB30671.1| (S71571...   984   0.0
CRA|105000014644762 /altid=gi|10443734 /def=gb|AAG17555.1|AF233...      976   0.0

BLAST dbEST Hits:
                                               Score    E
gi|12893350 /dataset=dbest /taxon=960...       1778   0.0
gi|12790010 /dataset=dbest /taxon=960...       1463   0.0
gi|10142161 /dataset=dbest /taxon=96...         1443   0.0
gi|10158540 /dataset=dbest /taxon=96...         1366   0.0
gi|12796371 /dataset=dbest /taxon=960...       1356   0.0
gi|12340179 /dataset=dbest /taxon=96...         1320   0.0
gi|9342125  /dataset=dbest /taxon=960...       1185   0.0
gi|12386814 /dataset=dbest /taxon=96...         1180   0.0
gi|12421686 /dataset=dbest /taxon=96...         1172   0.0
gi|12886387 /dataset=dbest /taxon=960...       1063   0.0

EXPRESSION INFORMATION FOR MODULATORY USE:
library source (from BLAST dbEST hits):
gi|12893350   Placenta
gi|12790010   breast
gi|10142161   Skin melanotic melanoma
gi|10158540   Ovary adenocarcinoma cell line
gi|12796371   breast
gi|12340179   Uterus leiomyosarcoma
gi|9342125    Lymph Burkitt's lymphoma
gi|12386814   Small Interstine duodenal adenocarcinoma
gi|12421686   Breast mammary adenocarcinoma
gi|12886387   placenta Tissue Expression:
Human fetal whole brain
```

FIGURE 1B

```
  1 MATTATCTRF TDDYQLFEEL GKGAFSVVRR CVKKTSTQEY AAKIINTKKL
 51 SARDHQKLER EARICRLLKH PNIVRLHDSI SEEGFHYLVF DLVTGGELFE
101 DIVAREYYSE ADASHCIHQI LESVNHIHQH DIVHRDLKPE NLLLASKCKG
151 AAVKLADFGL AIEVQGEQQA WFGFAGTPGY LSPEVLRKDP YGKPVDIWAC
201 GVILYILLVG YPPFWDEDQH KLYQQIKAGA YDFPSPEWDT VTPEAKNLIN
251 QMLTINPAKR ITADQALKHP WVCQRSTVAS MMHRQETVEC LRKFNARRKL
301 KGAILTTMLV SRNFSVGRQS SAPASPAASA AGLAGQAAKS LLNKKSDGGV
351 KKRKSSSSVH LMEPQTTVVH NATDGIKGST ESCNTTTEDE DLKAAPLRTG
401 NGSSVPEGRS SRDRTAPSAG MQPQPSLCSS AMRKQEIIKI TEQLIEAINN
451 GDFEAYTKIC DPGLTSFEPE ALGNLVEGMD FHKFYFENLL SKNSKPIHTT
501 ILNPHVHVIG EDAACIAYIR LTQYIDGQGR PRTSQSEETR VWHRRDGKWL
551 NVHYHCSGAP AAPLQ (SEQ ID NO:2)
```

FEATURES:
Functional domains and key regions:
[1] PDOC00001 PS00001 ASN_GLYCOSYLATION
N-glycosylation site Number of matches: 4
```
    1    313-316  NFSV
    2    371-374  NATD
    3    384-387  NTTT
    4    401-404  NGSS
```

[2] PDOC00004 PS00004 CAMP_PHOSPHO_SITE
cAMP- and cGMP-dependent protein kinase phosphorylation site Number of matches: 5
```
    1     33-36   KKTS
    2     48-51   KKLS
    3    259-262  KRIT
    4    352-355  KRKS
    5    353-356  RKSS
```

[3] PDOC00005 PS00005 PKC_PHOSPHO_SITE
Protein kinase C phosphorylation site

Number of matches: 3
```
    1     47-49   TKK
    2     51-53   SAR
    3    410-412  SSR
```

[4] PDOC00006 PS00006 CK2_PHOSPHO_SITE
Casein kinase II phosphorylation site

Number of matches: 12
```
    1     36-39   STQE
    2     51-54   SARD
    3     79-82   SISE
    4     94-97   TGGE
    5    109-112  SEAD
    6    385-388  TTTE
    7    386-389  TTED
```

FIGURE 2A

```
     8    387-390  TEDE
     9    404-407  SVPE
    10    410-413  SSRD
    11    465-468  TSFE
    12    534-537  SQSE
```

[5] PDOC00008 PS00008 MYRISTYL
N-myristoylation site

```
Number of matches: 4
     1    302-307  GAILTT
     2    375-380  GIKGST
     3    378-383  GSTESC
     4    400-405  GNGSSV
```

[6] PDOC00100 PS00107 PROTEIN_KINASE_ATP
Protein kinases ATP-binding region signature 20-43 LGKGAFSVVRRCVKKTSTQEYAAK

[7] PDOC00100 PS00108 PROTEIN_KINASE_ST
Serine/Threonine protein kinases active-site signature 132-144 IVHRDLKPENLLL

[8] PDOC00364 PS00402 BPD_TRANSP_INN_MEMBR
Binding-protein-dependent transport systems inner membrane comp. sign 405-433 VPEGRSSRDRTAPSAGMQPQPSLCSSAMR Membrane spanning structure and domains:

| Helix | Begin | End | Score | Certainty |
|---|---|---|---|---|
| 1 | 195 | 215 | 1.665 | Certain |
| 2 | 319 | 339 | 0.818 | Putative |

FIGURE 2B

```
BLAST Alignment to Top Hit:
>CRA|88000001156376 /altid=gi|7434378 /def=pir||JC5636
            Ca2+/calmodulin-dependent protein kinase (EC 2.7.1.123)
            II gamma-E - human /org=human /taxon=9606 /dataset=nraa
            /length=556
       Length = 556

Score = 1083 bits (2771), Expect = 0.0
 Identities = 534/577 (92%), Positives = 539/577 (92%), Gaps = 12/577 (2%)
 Frame = +2

Query: 113   MATTATCTRFTDDYQLFEELGKGAFSVVRRCVKKTSTQEYAAKIINTKKLSARDHQKLER 292
             MATTATCTRFTDDYQLFEELGKGAFSVVRRCVKKTSTQEYAAKIINTKKLSARDHQKLER
Sbjct: 1     MATTATCTRFTDDYQLFEELGKGAFSVVRRCVKKTSTQEYAAKIINTKKLSARDHQKLER 60

Query: 293   EARICRLLKHPNIVRLHDSISEEGFHYLVFDLVTGGELFEDIVAREYYSEADASHCIHQI 472
             EARICRLLKHPNIVRLHDSISEEGFHYLVFDLVTGGELFEDIVAREYYSEADASHCIHQI
Sbjct: 61    EARICRLLKHPNIVRLHDSISEEGFHYLVFDLVTGGELFEDIVAREYYSEADASHCIHQI 120

Query: 473   LESVNHIHQHDIVHRDLKPENLLLASKCKGAAVKLADFGLAIEVQGEQQAWFGFAGTPGY 652
             LESVNHIHQHDIVHRDLKPENLLLASKCKGAAVKLADFGLAIEVQGEQQAWFGFAGTPGY
Sbjct: 121   LESVNHIHQHDIVHRDLKPENLLLASKCKGAAVKLADFGLAIEVQGEQQAWFGFAGTPGY 180

Query: 653   LSPEVLRKDPYGKPVDIWACGVILYILLVGYPPFWDEDQHKLYQQIKAGAYDFPSPEWDT 832
             LSPEVLRKDPYGKPVDIWACGVILYILLVGYPPFWDEDQHKLYQQIKAGAYDFPSPEWDT
Sbjct: 181   LSPEVLRKDPYGKPVDIWACGVILYILLVGYPPFWDEDQHKLYQQIKAGAYDFPSPEWDT 240

Query: 833   VTPEAKNLINQMLTINPAKRITADQALKHPWVCQRSTVASMMHRQETVECLRKFNARRKL 1012
             VTPEAKNLINQMLTINPAKRITADQALKHPWVCQRSTVASMMHRQETVECLRKFNARRKL
Sbjct: 241   VTPEAKNLINQMLTINPAKRITADQALKHPWVCQRSTVASMMHRQETVECLRKFNARRKL 300

Query: 1013  KGAILTTMLVSRNFSVGRQSSAPASPAASAAGLAGQAAKSLLNKKSDGGVKKRKSSSSVH 1192
             KGAILTTMLVSRNFS                    AAKSLLNKKSDGGVK + ++ +
Sbjct: 301   KGAILTTMLVSRNFS--------------------AAKSLLNKKSDGGVKPQSNNKNSL 339

Query: 1193  L-----------MEPQTTVVHNATDGIKGSTESCNTTTEDEDLKAAPLRTGNGSSVPEG 1336
             +           MEPQTTVVHNATDGIKGSTESCNTTTEDEDLKAAPLRTGNGSSVPEG
Sbjct: 340   VSPAQEPAPLQTAMEPQTTVVHNATDGIKGSTESCNTTTEDEDLKAAPLRTGNGSSVPEG 399

Query: 1337  RSSRDRTAPSAGMQPQPSLCSSAMRKQEIIKITEQLIEAINNGDFEAYTKICDPGLTSFE 1516
             RSSRDRTAPSAGMQPQPSLCSSAMRKQEIIKITEQLIEAINNGDFEAYTKICDPGLTSFE
Sbjct: 400   RSSRDRTAPSAGMQPQPSLCSSAMRKQEIIKITEQLIEAINNGDFEAYTKICDPGLTSFE 459

Query: 1517  PEALGNLVEGMDFHKFYFENLLSKNSKPIHTTILNPHVHVIGEDAACIAYIRLTQYIDGQ 1696
             PEALGNLVEGMDFHKFYFENLLSKNSKPIHTTILNPHVHVIGEDAACIAYIRLTQYIDGQ
Sbjct: 460   PEALGNLVEGMDFHKFYFENLLSKNSKPIHTTILNPHVHVIGEDAACIAYIRLTQYIDGQ 519

Query: 1697  GRPRTSQSEETRVWHRRDGKWLNVHYHCSGAPAAPLQ 1807
             GRPRTSQSEETRVWHRRDGKWLNVHYHCSGAPAAPLQ
Sbjct: 520   GRPRTSQSEETRVWHRRDGKWLNVHYHCSGAPAAPLQ 556    (SEQ ID NO:4)
```

FIGURE 2C

```
Hmmer search results (Pfam):
Model     Description                                    Score    E-value    N
PF00069   Eukaryotic protein kinase domain               309.5    4.1e-89    1
CE00022   CE00022 MAGUK_subfamily_d                      295.5    3.9e-87    1
CE00359   E00359 bone_morphogenetic_protein_receptor      14.8    0.0017     1
PF00534   Glycosyl transferases group 1                    3.3    9.1        1
CE00031   CE00031 VEGFR                                    0.3    3.2        1
CE00292   CE00292 PTK_membrane_span                      -59.7    1.5e-05    1
CE00287   CE00287 PTK_Eph_orphan_receptor                -63.5    0.00035    1
CE00291   CE00291 PTK_fgf_receptor                       -90.9    0.0016     1
CE00286   E00286 PTK_EGF_receptor                       -131.8    0.0056     1
CE00290   CE00290 PTK_Trk_family                        -154.9    0.00012    1
CE00016   CE00016 GSK_glycogen_synthase_kinase          -180.4    1.2e-06    1

Parsed for domains:
Model     Domain  seq-f  seq-t    hmm-f  hmm-t       score    E-value
PF00534   1/1        31     65 ..    161    195 .]      3.3    9.1
CE00031   1/1       133    161 ..   1068   1093 ..      0.3    3.2
CE00359   1/1       132    186 ..    272    327 ..     14.8    0.0017
CE00286   1/1        14    252 ..      1    263 []   -131.8    0.0056
CE00290   1/1        15    253 ..      1    282 []   -154.9    0.00012
CE00291   1/1        14    267 ..      1    285 []    -90.9    0.0016
CE00292   1/1        14    267 ..      1    288 []    -59.7    1.5e-05
CE00287   1/1        14    270 ..      1    260 []    -63.5    0.00035
PF00069   1/1        14    272 ..      1    278 []    309.5    4.1e-89
CE00022   1/1        10    305 ..     13    316 ..    295.5    3.9e-87
CE00016   1/1         1    345 [.      1    433 []   -180.4    1.2e-06
```

FIGURE 2D

```
   1 TTGCCCCTGG CCTGGTCTCC CTGATCAACC CGCGCCTGAA GGGTTTCTTT
  51 CTAATAATGG CCCTGGTGCT TGCGCAAGTC TAGACTGTCA GCTCCCAGAG
 101 GGAAGGCGGC TGGCAGCTGG CTCTGCGCAG GCTGGGGGCG CCTCCCGGGC
 151 GTGCAGCCTG GCACAGGCTC CTTGACCTTG GCTCTCTCCC CACGTGCTAG
 201 GAGCCCGGTT GGGGGCTCGG GACCCGCGTG TAGGACCCGT CCAGAGAGGT
 251 CAGTGGTCCA GACTCCTACA CTCCTAACAC ATGCACCCTC GCATGCACGT
 301 TCCCGAGCCC GCGCGGGGTC CGCCCCGGGA CAAGCCCATA AGTCGCGAAC
 351 CTTCCAGNNN NNNNNNNNNN NNNNNNNNNN NNNNNNNNNN NNNNNNNNNN
 401 NNNNNNNNNN NNNNNNNNNN NNNNNNNNNN NNNNNNNNNN NNNNNNNNNN
 451 NNNNNNNNNN NNNNNNNNNN NNNNNNNNNN NNNNNNNNNN NNNNNNNNNN
 501 NNNNNNNNNN NNNNNNNNNN NNNNNNNNNN NNNNNNNNNN NNNNNNNNNN
 551 NNNNNNNNNN NNNNNNNNNN NNNNNNNNNN NNNNNNNNNN NNNNNNNNNN
 601 NNNNNNNNNN NNNNNNNNNN NNNNNNNNNN NNNNNNNNNN NNNNNNNNNN
 651 NNNNNNNNNN NNNNNNNNNN NNNNNNNNNN NNNNNNNNNN NNNNNNNNNN
 701 NNNNNNNNNN NNNNNNNNNN NNNNNNNNNN NNNNNNNNNN NNNNNNNNNN
 751 NNNNNNNNNN NNNNNNNNNN NNNNNNNNNN NNNNNNNNNN NNNNNNNNNN
 801 NNNNNNNNNN NNNNNNNNNN NNNNNNNNNN NNNNNNNNNN NNNNNNNNNN
 851 NNNNNNNNNN NNNNNNNNNN NNNNNNNNNN NNNNNNNNNN NNNNNNNNNN
 901 NNNNNNNNNN NNNNNNNNNN NNNNNTGTAA GCCACCGGCG CCGGGCGGTC
 951 TCGACATTAA ATTTCAAAAT GTTTTCTCCG GTTTGTCACT TGTGGTTTTA
1001 CTATGTTCAA TGGGTCTCAC CAAGCAATTT TGCAAAATAG TTAACTTATT
1051 CTCTTTTTCT TACATGACTT CTTGACTTTG AGCCATAGTT AGGAAAGGTT
1101 TGCTCACTCT CACATTAGAG TAAAATTTAT CCACATTTTC ATCTAGGATT
1151 AGTGCTCATT TTTTTATTAT TATGAATATC TTCTTCATTT GGGGTTTGTT
1201 CATGTATATT CCATGAACAA TGGACGCGGG TGCAGCATTT TAGCATCAGC
1251 TATCCCCTTC CCATCCGCAA TGAGCTGGCC GCTGCAGCAG CCCCGGCCCC
1301 CCACCCCCAC CCGCGGCGCC GAGCCCGGCC ACTGCAGCCC CCGCCCCGCC
1351 CGCCCCCCCA GACGTTTCCA GAGCTCAGAG TGCGAGCTCC CGTTTGACGG
1401 GGACGTCAAG GAAAATAGCA TGGGAAGGGG AGTTCTTGAT GTCTGACTGT
1451 GTCCTCTCTT CCCTTGCTGT CAGTTGAGCC GGGATGCAGT GAGATGAAAC
1501 CGGCTGTGGG GGGGTTTGAG CCTCACTTTG CCCCATGGTT GAGGGAGATT
1551 TCTCTTTCAG GGGATGATAC CCTCTTTTTA ATCTTTCCTT CCCCGACCTT
1601 CAGCTGTTCC TGCTGAGAGA AGGGCAGGGT CTCTCTGCTC CCTTCTGCCC
1651 TGGTTCTCTT GGCCGGGACC GCAGGGCTGT CTGAGATGCA GCAGGTGTGT
1701 GTTTTCAGCA TCGCCCACCC GCTCCTGATG TGCAGCCTGA GGTGGAGGCT
1751 GTTGCCTTGC CCAGGGACTG GATGAGGGGG TGGGAGCGCG GCACGCCACC
1801 CACATCTGTT CAGTGTCCTG CGGTGGCCGC GTCCTTTTGC CTCATGTTGG
1851 ATGGTGGTGG TCACAGCGCC GGTGTGTGTG CATGTACGTG AGTGTGACTA
1901 GAGGTCTGGT GGTGGAGCA TCATCGTCCC CAGACTTGAA GTGTGTCTGT
1951 GTCACTCTGC CCTGCTCCGT GTCCCAGTTC TTTTCCCCTT CTCCCTCCAG
2001 GGGTGCTTTC TCTGTGGTCC GCAGGTGTGT GAAGAAAACC TCCACGCAGG
2051 AGTACGCAGC AAAAATCATC AATACCAAGA AATTGTCTGC CCGGGGTGAG
2101 TGTTCCCTGT CTTGACCTCT TCCTGAGGGT GCCTCCAGGG GCCATGGTTT
2151 CTTTTGAGGA AGCCCCAGGA ATTGGGGGTT GTGCGTTTTA GCACTTGGAG
2201 AGGAGTTGGA ATTTCAGACT GGTTGGACTT TGTGTCAGGC TGAAGCCAGA
2251 AAAGGAGTTG CATGGGGGAC TGGAAGCGCC CAGGTACAAA AGAATGAAGG
2301 AAGAGATGCA AGTAGCTGCA GTGGCCCCCA AAGGCTCAAG GGAGTTCGGT
2351 CTTCAGGGAG GTGGAGGATA TGGGGGTAGT GGGTGGTACA GAATGGGGAG
2401 CTCTTAATTT GGGGCATTTG GAGCCTCTCC CTTTGGGGCA GTGGTGGCTA
2451 CTGCAGGCCT TTCCTGGTCC CTTCTTCACC ACGGGCTGAG TTAGGATGGA
2501 AATGCAGTAA GTGAGCAGCT CTGACAAAGC CAGCCTCCCC TGCCCACCAG
2551 GCGGCAGAAC AGACTCCCAA GGGAAGGGAA TCTGTAAACA TCAGGGGAGG
2601 CTGCTACTGG CGAGGGCTTC TCAGGAACAA ATTCTGCCAG ATGAACTTGA
2651 TTGCTTTTTT GATCAAATTA CAAAGTTGGT GGTGCAGCAG CAGATGTAGT
```

FIGURE 3-1

```
2701 CTGTCCTGGG TGGAGGGTGA TGCCTCATGG TCTAGAAATC CCAAAGGCCC
2751 GGTTTGGGCA GGAACTGCAC TGCCTCCGAA CTGCACTGCC TCCGAGTCTG
2801 AGGAGCATAA AGGCCAAGGC CTTGGGGCCT CACTTGCGAG ATCCTCCCAA
2851 GTACCTGAGG CTTGGAGGGT CAGGGCCTGT CTTTCACACC TTGAACCTAC
2901 ACTCTCTGAA CTTCCTATTG GGTACTTGCC AAACTCACCT CATCTGATAG
2951 GTGTAGACCC AGCAATGTGT GAAGTGCTCT GGGAACAGGT CTGGTGAGTA
3001 CAGAGGTCAG ATCTCGGAGG GCTGCAGGGT GCAGCTGGGG GACAAAGGTT
3051 GTGAAACTCA GAGAAAGGAA TTAGGGCTGG GCAGTAGGAT GCCATAAATA
3101 TATTTGGAGC CAGGACACAT GCCCTGGGGA AGACATGGGC TTTGGCCAAT
3151 AATGACACGG GTTTCTCTGG GATAAGAGAC ATAATAGATG TCCCAAATGC
3201 TTAGAGAAGC TCTACAATTC CACGGGCTTC TGTCGTGTTG GCAGTTGTTC
3251 TGGGACCTGT TTAGCAGGGC CGTGTCCACT CCCTGACTGG GGACTCTCTC
3301 TCCATCCCTC TGGTAGGGCA CTAATTGCTG ACTCCCATCC AGCTCCATCT
3351 CTTGCTGTTC GTGTACATTG CCTATAAAGT TGGACTTGTT TGTTTTCTTT
3401 CTCTCTGGGT ACCTTGAGTC TGAGGATGGT TGCCATAGAG ATATGTGGGC
3451 AGTCAGATAC CCTGGAGTGG GGGTGGGGGG GACAACAGGG GCTGGGCTCT
3501 CTGGCAGACA TCCTCTGGCC AAGGATGGAA GGTGCAGGCA GGAACAATGG
3551 CTTGAGGCTG GATACCTCTC TTGCCCACAC AGCAGAGCCC TGGTGCATCA
3601 GAAACAGGGC TGGCATCTGG TGTCTCCAGT TGATGATGCA ATGCTTTGCT
3651 CTCTTCATCT CACCAGTGTC CTCTGACCCA TGGGTAAGAG AAGGAGAGAT
3701 GGCTGGGAGC CGAATTCTGG GATGTGAGGA TAGGTGATGT GGTGACTTCC
3751 TGCAGCTGCC TGACTGGGGC TTTCATTTCC TACTCCTTCC CTACCTGCGT
3801 AAATTTCCAT GACCTGTGTG ATAGCCTCCC TTTCCCTTCC TCACCTCCTT
3851 TTAACCTTGT CCCATCTTTC CAATGGATA TCTTTCCCTG GCCAAACTGG
3901 ATGAGACTTG ATTTCTCGTT GATTTTTTTT TTTTTCCCCT CAAGAAGAGG
3951 ATTCTTGTGT AAAAGTATAT GCTTCAGACA GCAACTCCCC CTCTCCCAAG
4001 ATGGATATGC CAAGACTGGG CTCTGTTGTG TGGCCTCATG TGCCAGGTTG
4051 ACTTTGGGAC AGAGGCACAG ATGATAGGCA CAGATGCCAG CCAGAGGGGT
4101 CAGAATGTGT AAGTGCCAGC CAGTACTGTG TGGAGGTGGG AAAGTGGAAA
4151 GGGGCTGTCT TGGAGATGGA GGGAACAAGG TGGGGCTGGA CTATAGGTGT
4201 GGGCATGGGA GATGTGAACT CCTGGAGAGA TCTGGGCCAG GGTAGCCATG
4251 GGCTGGTTCC CATGGGGTTA GGGAGTGAGG GCCATGGCTT CCCTGCAGAC
4301 TCTCAGTTTA CACTATATAT TTTATAAAGG TGCAGCCACT GGAGCTGGGT
4351 TTCACTCATC GCTGTCTGCC TAGGTCTCCG CAGGTGTTGG ATTTCTGTGT
4401 CTGGGAATGT CGTGGGCCCA CCAGGGTCAT CTGTGAAGGT CTGAAGGGGC
4451 TTGCTGTGTT CACTGGGTCT TCCTGCCTCC TGTCTTTCTT GTTTGTGATT
4501 CTCTGGGCTA CAAACTGAAA AGATAAAAAG AGGGTATAGA GCTGTTTCTC
4551 CTTGGCATCC CTGGTGAGGT GGCTAGGAGT CAGGGAGAGG GATCACCTGT
4601 TCTTCTGGGG GGGTCCAATC GAGACAGGAA GCCTTCTTTT GGGCTGTTGT
4651 GTCTTGTCAC TGTGGCCTCA GAGGCCCACA TTGGCGGCTA GGTTGCAAGG
4701 TGGGAGTTC ATGCGGATAT GCGTTGAGCA CTGTCTTTGT CTGCGGGCCT
4751 GTCTACATAA AGTCACTGAA AGTCACATAA CGTCACTCCG TTTGCTTCAG
4801 AACCGTGATA GGAGTGGAGC TGGGCTCTTA AGGGAGCCCA TGGTTCCAAG
4851 CTTAGCTCCA CTAGGCCGAA GGAGGCATTT AAAATAGGCT TGGATGCAGG
4901 AGCTAGTGGG CCAGGTGATG GCAATGATAA GTCGTTATTT TAAGATTTAA
4951 GAGCACCCCC CTCAAGGAGC CTGAGCCCTT ATGTCTTTTT TTATTTTTAA
5001 ATCTTCATAT TCCCTTCTTA TCTTTATTCA TATGCATACA GATTTTCACC
5051 TCGTGGAGCA TAACATTTTA TATCCTGCTC TCTTTGCTTA TATCCAAAGC
5101 ATTTCCCCCA TATTACTACA GTTGAAGGGC AAATGGTCCT TTCTTCTACG
5151 TCGTTTAGGA TTTATCCCTA AAACAATCAG CATCACAAGA AACTTCTGTA
5201 TATGTACCAT TTATCTGGAT TCCAGTTGCT TTTACCAAGA TAGATACTGG
5251 GGTAATGCCC TTGGCCTTAC TAAGAGATGC TACCGGAAAC AGTGTTTTGA
5301 AATCTGTTAT AATACTTTAA CATATTTATT TAATCTGTAC ATTCCGTGTG
5351 AAGAAATTTC TTTTGAAGCT AAATGTAAGC AAAAGCTTTC CTCTTTGTGA
```

FIGURE 3-2

```
5401 GGACCTGAGA GGTGAGGGAA GGGTCCTTAT GTGTTTCTAT ACTTCTGCAT
5451 GGGCAGGCCC TAGCGAAGTG CCTGACGTAT GCCAGCCACA TACACATTAA
5501 ATGAATGGGT CAAGAGGACT ATGTAACCAA TCATGGTTGC CTTTTGGCTT
5551 TGGCTCCTAG GAAACTCAGA GTCAAGTTGC CAGAGCCCTT GTACCCTGCT
5601 ACAGACTTGG GTCCTCCCTT TCTGATCCAG GGAGCCAAGC TGCAGACCTG
5651 ATACGGCTGC TGGAAGAGAG GACAGATGAG GATAAAGACC TGTGCTTGGG
5701 GCATAAGGCA GAGTGGGAGA TGTAGGCAGA CATTTAGCTG ATGATTCCTC
5751 CTTCCCTGTC ACTAAATGGC ACTATAGGGC CACTGTTGGG ATCTCTTCCA
5801 GGTAGTGATT TTCAATTTTA GTGTGCGTAA GGATCACCCT GAGTACTAGT
5851 TTAAAAAATA CAGACTTCTG GGCTTTAGCC ACAGAGATTC TGCTTTAGGA
5901 GGTCTAGGGT GGAGCTGCAG AATCTGCATT TTTAACACAT GCTCCAGTGA
5951 ATTTCATGCA GGTGAGGCAT GAGCCACTCT TTAAGAGATG CCACCTAAAA
6001 TCTGCAACAA CAGTTGCTCT TGCCATGCCC TCTGGAATTC AACAGACACA
6051 CCTTGGCCCA TCCTTCTCCA GATTGTGTGT CTGCCACTAT GTGGCCATCT
6101 GTGCACATGG GCTGTTCTGT GATTAGGGGC CTCGTTCTGG GCCTCGGGAT
6151 TGGGGTGTCT GTGTCTGAGG CTGCGGCAAG CTGGGTGGCT CGGGTTGTGG
6201 CATGTTGGCC ACCAGAAGGG TAAAGGCTGT CCCTTTCTGG GTCCAGCTGG
6251 CCCTGGGGAC TGAAATGGGA TCCCCTGGAT GGTGCCAGCT GAGAGTCCCC
6301 GCCCCCTTAG TGTTGGCCTG AGTAGCCCCC ATGACATTTG TGTCCCCTGT
6351 GGTATCTCCA AGTGAGACTT TCCTGTTAAG GATCTGGGTG AAGTGAGGGA
6401 AAGAGAAGGG AGGGGGAAGC AGTAATGCAG GGAGTGGGAG AAGGAAGAGA
6451 AATCCACACA GCACTGGAAC ACAGGCCTCG AGGAAGCATT TAAGGAGGCT
6501 GTGTGCGAAA CCATGCTTTC CTCCTGAGGA TAAAACAGGC CAATTTCTGT
6551 AAACAGAGAA ATGGGCATCC TGCATATCAG TGATGGAGCG CCTCTACTTT
6601 CTCTCCTGAA GGGATGGAAG CCGACTGCAG GTCCCTCTGT GCAAAGGCTT
6651 CTGCCAGGCG GCTTTTGTCA CGCGGTCACG TTGAGCTGTG GGCCTTAGCA
6701 CACACAACAC TGGCCTGTCC CCCTCCCCTC CCACCTGTCT TCCTAGAGTG
6751 ACTTGGGGTG CTGCATCATG GTGTGGGGAT GGAGGTGGGA AGGTTGCCCT
6801 GTCCTGTCAG GGAGGCCCCT GCCTTCTTCC TGCTGCTTCC TCTGGTCCCT
6851 TGTCACCATA CCCTTGTTCG AAGCTGTGCT GAAACCCTAG AGGTGAGTGG
6901 CTGACCCCAT TCTCTGCTGA GACTGGAGAT AGGGAAGGGG AGGCTGGGTG
6951 TGACCATTCC TGCTCCCATC TGTATGCTTG CTGCTCTCTG AACAGCTTTG
7001 GCAGACCAAC AAGGGCCTGA TCCCATGGGT GCCAAAAGGG TGGTGACAGG
7051 AGGAGATGGG CACTTTGCAC CTCTTGAATG CCTCTCTGCA GAGCCCCTTT
7101 GTCACCTACC CATGGCCAGA CAGATCTGCC GCAGGACCGC TGGGGAAATC
7151 AAAGCACAAA AGCTTTGTCT GGGGTCTTTT TTTTCTTTTT TGGTTTTGTG
7201 CTGCAGGTGC CCATGACTTT GCCAGGGCTC AGACCCAGCG TCCTCAGGCC
7251 GTGTGGCCTC CACCCACTCC TTGGCGCCTT TCTTTAAAAC ACAGGTTCTG
7301 GATACTTTGT TCCTGTGATG AATCTTGGCA TATCACCTCA CACCTCTCCA
7351 TCTAGGCCCC AAGCTCCAAG CCTGGTGGAG CAAATCCCTC CTCGTTGCTG
7401 GCTGAGGCCC CATTCCCGTC TGTACCCACC TCTCTGGGCT GTGCGGTGGG
7451 GAGATTTCCA GCCACTCCTC CCCAACACCA TCTCCGCTTC CTGGGCCCTA
7501 TCAGCAGCAG CCGCAGCTTC CCATCTGCTC CCCTCTTTTC TCCTCCCTTT
7551 CTTTCCCTTC CCCCCTGCTT GCTGCTGCCC TGGGAGGAGC TATTTTTAGG
7601 GGCTGCTTCC TGGGATGTTT TACTTGGGGC TGGTTACCAT GAAGGAAATG
7651 TCACCAAAAC AGTGGGCAAA GGCTGCAGGC ACCGGGAGCC CTGCCGGGGG
7701 GCATGGAGAA CAGACGGCTG ACCCTTTTCT GGCCCTTGAG AGCAGCCAGA
7751 GTGCCCCCAG GCAGAGCCTT GCCTTCTTGG GGCTTGCTAG TGACCCCTTG
7801 GGGATTTTCT CTGTCAAAGC TGATTGAGGG CCTTTTCGCT ATAGGGCATT
7851 TCTTGGAGCC TCTCGCTTCC CTTGCCTTGA GATCCAGAGG CCAAAGTGGG
7901 GCTCAGGTCT TTGTGTCACC AAGTTAAAAC TGCTTGAGTG AGGGTTGAAG
7951 ATAAGGGGAG GATGCTGGGT ACATGCACAG AGCCTTGGGG GTTCACATGG
8001 GACCATTTCA GGCCCCGTCC CTCTGTATCA CAGCCCCCAG CTAGTCACCA
8051 GGTGTACATG TGTGAGGGCA TTAGAAACCA TGGTCCTGCT CTTGTGTGTC
```

FIGURE 3-3

```
8101 GGATGGACTT TGCTTTTAAT TGGAGACTCT TTGCATCTTT AGAGTGAGAT
8151 TCAAAGAGGA AGGGATGTGG CATCACAGTG TCAGGGTGAG GTCGGTGGGA
8201 TCGTGGCTTG GGATTCCCAC TGGTCAGTGT CCCAGGCCCA GGGCTGTGCA
8251 TAAGCAGCTG GGGAAGGTGG ATTATGACAT CAAATCCCTG CGATGTCCTT
8301 GTTTCTGCTC CTCAGAGTGC CAAGGGGACC AGACGGCGGC CTCTGCTGCT
8351 TGGGAAGAAG ATGAAAGGCA CTCAGGAGGG CAGCAAGTGA GGCCGCCTCC
8401 CATGGAGCCC TGAAATCAGT GGGGTTGCAG GAAGTTTCTC ACATCCATGT
8451 TTAGGGTCAT AGGCACAGAC CTGCAAAATA CCCTTTGCAA AGTTAAGAAT
8501 GTCTTTGAGA TTGGAACTTG GGAGAGTCCT CAGTCAGAGT AGGAATGTGC
8551 ATCCTTTCCC ACGTACAGAG GATTGTATGT TTACGTGGCA GCAGGATCTT
8601 ATTTGAAGCT AGTGCTGGCA TTTGTGTTTT TTTTTTAGGA AAATGTCACT
8651 AAGTCAAGCA GGCCCATCCC TGAGAGGGCC ATGGAGAATC TGTGGCCAGC
8701 CCTCCCTGGC CCCCTGACCT GGCAGAGGAA GGAAAGGGCA TTGGAGTAGG
8751 CTTCTGTCTT CAGGCCAGAG GGGGAGGTGG TTCAGGGGCA GGCTTGGTGC
8801 ACCCCTTGGC TGCAAGCTAT CACCTCCCTA TCTGCTTCCT CTTTTCTGCC
8851 TCCCCTGGTG CATCTGGTCA CTTCTTGCTG CCCTTCCTGT GAAATCGTGG
8901 CACCTTGGAC CAAGTCCTGA AGCACTTGGG CAGAAGGCGG GAGAGGTTGG
8951 GTTTCTAGGA TCCTTGTTTC CCAGGGCCTG GCTCTGGCCT GGGCTCAGAC
9001 CACTCTGGTC TAGGCAGGCT GCTGGGAAA GGCTGGAGCT GCTTCTGCTT
9051 TCTGCTCCTG TTGCCACCTC TGCTAATGAT GGGGAAAACC TGCAGAGGGC
9101 TGTGGTTGGA GCTGGGCTGA AGGCCGGCAG GGGTGGGTCT CTCCATGGCA
9151 GTAGCACACA GGCAGGCAGG AAGTGGCCCT GTGCAAAAGC GGGAAGTGGC
9201 AGTTGTCAAA CAGGAAGGGG GGGGCTGGGC TGTGGGAGGG GCGGGGATGA
9251 GCCTGGTAGA AAGGTGCGTG GAGGAGGGTC CACCTTGGAA GGTCTGAGCC
9301 TCTCCCTAGT GGTTACTGGA AGGAGGGGTG TCTCAAGGGG AGACACCTTT
9351 GCAGCACCTT GAGATGCCGA GCCAGGGCCC TCCCACTGTG GACCAAGCCC
9401 ATTCAGTGGC CTCGCCCTTT TTGGGGTTGG AGATGCTGCG TCCAGCTGGG
9451 ATGCCCTTGC TTTTGGGAAA GATGCTCTAG AAACCACTAC TCCATCCTGG
9501 AACCCCTCTG CTGCCACTGC TGCTGGGATG GACCCTCTGC TTTTTTGCAG
9551 CCGTGGGCCA GCCCTGGATG TGACTACAGG ACAGGAAGTG TCAGGGGAAG
9601 AGACAGGAGA CAACAGCTGG AGAGGCTGGG TGGTGGCCGG GCAGTATGTG
9651 GCAGCAGGAA CGGGGAGAGC GGGGCAGGTA GAAACTGCTC TGTTCATTGA
9701 GGAGAGCTTG TGGATGGCAG GGTGCCACGG CTGCGAGGAA GAGGAGGGAA
9751 GCGGACAGTG GCACTTCCTG CGGCGTTCCC CTCTCTCTGA GGAGCCCCTG
9801 TTGCTGCCCA TCACCTGCAG ACTGTAGACA CAGGTGGGCC CCGCCAAAAC
9851 AGGGAGGGAC ACTCCACCTC CAGGACTGCA ATGGAGGACC ATGTGGGGAG
9901 CCCAGAAGCC AGGCAGGAGG GCTTAGTTGC TGTGTTGCAG ACCCTGCATC
9951 TGCCTGGGCT GAGGGGACAG TGGGTCCCAT TCACAGTGTC TCTGGTGATA
10001 GCTGTGGCCA CAAGCCCAGC CCAGGAGACC CTGTCAAGCT TCTCACTGGG
10051 CCCTTGGAAA GGAGCTATAT GCCAGACCTT ATGCAAAACT CTTGACCTGT
10101 ACCACCTCAG TTAAACCTCA GATCTTGCTG TCTCTATTTT AGAAGTGAGG
10151 AACCTCTTGG CCGGGTGCCG TGGCTCACGC CTGTAATCCC AGCACTTTGG
10201 GAGGCCGAGG CAGGAGGATC ATAAGGTCAG GAGATCGAGA CCATCCTGGC
10251 TAACACAGTG AAACCCCGTC TCTACTGAAA AATACAAAAA AATTAGCCGG
10301 GCATGGTGAT GGGCGCCTGC AGTCCCAGCT ACTCGGGAGG CTGAGGCAGG
10351 AGAAGGGCGT GAACCTGGGA GGCGGAGCTT GCAGTGAGCC GAGATCATGC
10401 CACTGCACTC CAGCCTGGGC AACAGAGTAA GACTCCATCT CAAAAAAAAG
10451 CAAAAAAAAC AAACAAAAGA AGTGAGGAAC CTCTTTCCCA AGATAATGTG
10501 CCTGGCTCAC TGTCTCACCT ACTTTGGGTC CTAATCAAAT GTCACCTCCT
10551 TACTGAGGCT TTCTTGGACT GCCCTACTCA AATCTGCACT CCCCACTTTC
10601 TCTGCTTTTT CTACGCAGCA CTTGCCGTGA CATCTAACGT GCTGTTGAGT
10651 TTTCTTACTG TCCATCCCTC CCCCATACAC AACCCACTAG AGTGTCAGCT
10701 CCATGAGGGC AGGGATTTTT GTCTGTTTTG TTCGCCACTG TCTTCCTAGC
10751 ATCTTGAATA CTGTCTGTCA CATAGTAGGC CTCAGTAAAT ATTTCTTTTT
```

FIGURE 3-4

```
10801 TTTTTTTGAC TTGCTCTGTC ACCCCAAGCT GGAGTGTAGT GGCCCAATCT
10851 TGGCTCACTG CAGCCTCCAC CTCCTGGGTT CTAGTGAGCA CATTTGGCTA
10901 AATTTTGTAT TTTTAGTAGA GATGGGGTTT TGCCATGTTG GCCAGGCTGG
10951 TCTTGAACTC CTGACCTCAA GTGATCCACC CACCTTGGCC TCCCAAAGTA
11001 CTGGACTGGG ATTACAGGCG TGACCCACCG CGCCCAGCCA CGATAAATAT
11051 TTCTTGAAGG AATGAATGAA GCTCGGGTGG GTTTAATAGC TTGCTGGATG
11101 TGGCAGTGTT GGGCTCAATC CAGGGCTGTC TGACTTCAAA ACCGATGTGT
11151 TGTTAATTGC CATACTCCAC AGCTTAGAAT CAGAATGAGG ATCAAGGTAT
11201 AGTCCTGGGG TTCAGAGAAG ACCTGGGCCT TGCCGGGAAC ACAGGGCTCA
11251 GCTCCTTGGA GTTAAGGCTG AACTAAGAGG CTAACAAGGA CCCTCTGGAT
11301 GCTGGGCAGC TCCTTTGAGG AGCTGGGAGC CTGAGTCTGT GTATCTTCTC
11351 TCCACTCAAA GTCACTGGTA AAGCAGAGTG CCCTTATTTT TAGTGCTGTT
11401 GCTGTTGTGG GACTGTAACC ATTAGCTAGT AAGAGACTTA AGGAAGGAGA
11451 TAAACATTAA TCTTCTGGGC CTTCCCTCAG CTGCCACCTC CGCATTGCAA
11501 GATGCTGTTC TCCTGCACCT GCCCAGGCAA CCAAGCCTGA GAGTTATGGG
11551 CTGGAGGGTG GTGAGGTTTG TGCCCAGAGA GAGGGCCGTG GGTCTGTAGC
11601 TTTGGGGCTG GCTGGCTTGG TACCTCCATC TCAAGTCCAG GGATGGAAGG
11651 AAGGTGGGGT CATGTCAACA TCCTGCCAGA TCTGGAAGAA GCAAGCCCCC
11701 CAGCCACCAG GCAAGGCTGT TACAGCCTCC TTGAGTGCCT CGCTTCTGGA
11751 GGTCACTGGC CACATCCCTG TGCCTGGGAC CAAGGGATGC CAGGTGATCT
11801 GGGAGTTGGG AGTTACTTGG GGTTCTCCTG GCTGCATCCT GGTCGGTGGT
11851 CATGCTGAAC CCAGGCACAG GAAGGAAGGC CTGACCCAGA TCTTTGGGCA
11901 GCTGGGACGG ATTAGCTGGG CAGCAGGAAC TAATCTCTGT CTGTCCCCAC
11951 CTCTTTCCAC AAAGTAGAGC TGTTGCTAGA GGGAAAGTTT AGGACAAAGC
12001 TGGGTTTGGT TAGTGAAACA ATAAATGTGA ATTTCTTCTA GTCCATAATC
12051 CCTACATTAT CTCACACTGA CAGTCCTGAG TTTGAATCCC CCTTTTATCC
12101 CTTTCCTGCT GTGGGATCTT GGGCAAGTTA CTTAACTTCC CTGGGCCTCC
12151 GTTTCTTCCA TCATCTGGAA ATGTGGACAA TCATAGCATT TACCTAATGG
12201 GATCATTGTG AGGGCTGTGG GAAGATTTAC AGAAGCTTTT TGCTGTTTAG
12251 GGTAGAGGCA GGGAGACAGG AATAGCTTGG CAGCTATGGA TGTGAAGGCC
12301 CCTGCCCGGG CCTGGATAAT TCAGGGTGAA CTGGACTCTC TTCCTTTTGC
12351 ACCCCCTCCA AAGCCTAGAG TCTTAACTCA ACTCTCACCA TTCTTTATCT
12401 GGCCATAATA GCACAGGGGT GGAGAAAGAG GGCTCTAGGC TCAGACCACC
12451 TGCATCACTG CCTGTTCGTG TTACCTTAGG CAGATTACTC TATCTTTTTA
12501 AACCTGTTTC CTCGGTAATA TAATAGAGCT AATCAGATCC CTACTTCACA
12551 GAGTTTCTGT AGGTATGAAA TATGGTAATC CATGCCTCTG CCTGACATGT
12601 AGTCAGTGCA TAGTAAGCGA TTGTTATGGC GACTACTGTT ATTAGTAAAC
12651 CCTTATTAAG CCCCTGTTTA CAGAAAGAAC TCTAGAAAGC ACTACCTGGA
12701 AAGGTACCCC CGCCTTCGAA GAGCTTGCAA CTGAAAGATA ACTGATGTAA
12751 TATATGATGT GAGAATCGTG AGAAGTGCAT TGGGAAATCG GGGGGGGGGG
12801 GGTGGAGTAG GAGGGAGAAG TCACAGTCTA CCGAGAGGAG CAGGGAAGAC
12851 TTCATGAAGG AGGTGACTTT TGGCAGGATT TCAGCAAGTA GAAAGAGGGA
12901 AGGACAGTGG GGGAGGGCTG TGAGGCCTCC GTGCTGTGAG TAGCATCCTC
12951 TCTTCCCACG TACTGGAGCT CTGCCTTCCT GTGGAAGGAA TTGACCCACG
13001 CAGCTCACTT GGATCTGGGG ACTTGTGGAT TTCTGGTTAT TCCACCAAAA
13051 CCAAGTAATC CTGGAGTCTG AATTTGAAGA GGTCAAAGCT TACAGCCATG
13101 GTGGCCAAGA GGACTCCGGG GAGAAGCAGG ATTTGTGTCC TGGTTTCTCT
13151 TTCTATAAAA TGGGCATCAT ACTAATGCCA CCTCCTAGAT TGTTATGAGG
13201 ATAAATTAAA AGAGGCAGCT GCCTGGTGTA GAAGTAAGCT CTCAATAAAT
13251 GTTAGCTATT ATTATTTTAA GTCATCATTA TCTTGATCAT CAACCTCTTT
13301 ATTATCAGCA TCATTATGTT TCAGGCTTGC CATCAGGACT ATGTAGAGAA
13351 TATATGCAAA ACCCCTAGCC AGTGCCGAGT ATATATTAGG TGCTCAGTAT
13401 AACTTAGCTA TTATTAGTGT TCCTAACAAG AAAGAGATTC TGGGCCAGGC
13451 GCGGTGGCTC ACGCCTATAA TCCCAGCATT TTGGGAGGCC GAGGCGGGTG
```

FIGURE 3-5

```
13501 GATCACCTGA GGTCAGGAGT TCGAGACCAA CCTGGCCAAC GTGGTGAAAC
13551 CCCGTCTCTA CTAAAAATAC AAAAATTAGC CAGGCGTGGT GGTGTGTGCC
13601 TGTAATCCCA GCTACTCGGG AGGCTGAGGC AGGAGAATTG CTTGAACCCA
13651 GGAGGCGAAG GTTGCAGTGA GCTGAGATCA CACCACTGCA CCCCAGCCTG
13701 GGCAACAGAA CGAGACTCCG TCTCAGAAAG AAAAAAAGAG ATTCTGGACA
13751 CCCTGGACCA CTGAAACCCT GTTGTGGTGG AAAGAGCACC AGAGTTTTAG
13801 TTGAATACCT GGATTCAAAT CCCAGCTCTG CTGCTCACTG GCTCGAAGTG
13851 TGCAAACCCT CAAGTCATTT CCTCATCTGG AAAAGGTGGT CATAACTATC
13901 TATCTGGCCC AGGCCTGGTG GCTGGTGCCT ATAGTTCCAG CTATTCAGGA
13951 GGCTGAGGTG GGAGGATTGC TTGAGCCCAG GAGTTTGAGG CTGCGATCAT
14001 GCCACTGCAC TCCTGCCTGA GGGACAAAGT GAGACCCTAA AATGAAAGGA
14051 AAACAAGTTG TCTCCAGGAT TGCCATGACT TGCTGCATTA CTTCAGCAGA
14101 TCATCACAAA TGCATAGTTA GTACCTGAAC TGAAGGAATA TGAATAACAA
14151 GGTGACCACA AGGAGAATGG ATGGTTGATG GCTTTTGTTT TTTCTCTTCT
14201 GCTTTTAGAT CACCAGAAAC TAGAACGTGA GGCTCGGATA TGTCGACTTC
14251 TGAAACATCC AAACATCGGT GAGTGCCTGG GCATGGAGCA TTTTGTGGGT
14301 ATTTTGTAGA AGCAGGGATA ACAGATATCC ACTGCTTTTG TGTGTGGGAT
14351 CACCTCTGTC TGTGGACCTT CACCTGGTGT CTGTTTTTAC ATGAGCAGGA
14401 TAGCAACTGT GTCTCAGAAT TCTGGGGCAT TCTAGTTTAG AGACCTGAGT
14451 ATCTGCATCA CTGCGGCACC TTCTCAGGGC TGGGGTGTGA GGCATCAGAA
14501 TAGGTTTCAG ATGCTATTTC TTCCCTTTCT CCTTCTGTCT TTGGGCTGAG
14551 GTCCAGGGTC CTCAGCGTGT GAGGTTCCGG GCTCCTAGCC TGCCAGCGTC
14601 CCTCACCAGG GGCCATCCAC AGCCCTCATG CAAGGGTCAG GATTTTGTTT
14651 GTGGACCTGA AAGAGTTTTG TTCCTGCTGC GGTGTCCTGC ACACTCTGGG
14701 GGTTTCCATG GTGCTCCCAT TTGTATTCCC CAGAGCCAGG AAAGCAAGCT
14751 GCCCCCCTGC CTGGCTCCTC TGGCAGAAGG GATGGCAGGA ACCACTCAGT
14801 ATGGGGAAGG AGAAAAAAGA GGATTTCTCC CTGCTCCCAC CCTGACTGGG
14851 GGGACAAGAG CACATTGTTG GTTGTGCTAA AGCCTGAGGA GGTTTGCCTG
14901 CCTCAACCCA CTCTGGCTCA GTTTTACTTT GTTCAGCTGA AATGGTCTTT
14951 GCCAAAAGCG TTGGCCCTGA TTTGGTGCTC CTTGCAGAAG GGACAGAAAC
15001 TGGGCTGGCT GCAGTGTCTG AGCAGAAGCC CCAGTGTTGA CTTGAGGCAG
15051 AGCAAGGAGC ATCTCCTAGG TTTTCCCTGA AAGCCCTGAG TCATCACAAA
15101 AGACAACACG TGTTCTGTGC TCCTCAGGCA TGGCCTAAAT CTCAGGGCTC
15151 CCACCGTGCC CCAGAGGTCG CCTGCTCTGC TCTGTTGGCG GCCAGGGCTG
15201 TGAGGTGACT TGCTGAAGCC TAATGCTTCC TTCAGAGCTA CCCAGCCCCT
15251 GGCTTCCCAG GTCTCGGGCT AGAACAGTCA AAGTGAGCTC TGTCATGGAA
15301 GGGCTGAGGT CCTGCTCTAG CCCTCTGGGA GAGGAGCAGC TCTGAGGTAG
15351 TCAGAACGTC AGCTGTGCAG GGCTTTCTAG ATGGCAATCA GCAGCTTGGA
15401 TTACACCCGA AGCAGATTGG TGTGGCCAGT GGTGATCGGC TTTGCCTGAT
15451 GCAGTGTGTT CTGCAGAGCC AGCACCTCTC AGCTGGTGGG TTCCTGGCCG
15501 CAGAACTACT GGAGCTCCTA GGTGGTTTCT GAGGTTAGGC CTTCACCTGA
15551 AAACAGCGCA GTGGGGACTG ACATGTTGCC TTTGGTAGGA GAGGGCCCAC
15601 AGAGGGAAAC ACCTAGAACA GCAGTCACAG ATTAGGCATG TTTTGCTTGG
15651 CTGACTCAGT GGTCTAAAAA TATTTTTATT ATTTGCCAAT ATTTAAAAAT
15701 GAGATTTCAC ATTTTGAAAA AAGAAAAAAT CTATTCCCCC GCCTTTCCAG
15751 TCAGAAGGCT TGGCTCTGCT GAGCCCCCAC CTTGCATGGC CAGAAGGAGC
15801 TGTGAGGAGC GGTGGCTGCC CCTGCAGCCC GCTGGCCACT GTCCTTGTCA
15851 CCCACTATGA GCTACATTT GCATTACCCA CCTGGGCCCC TGTAGGCCTT
15901 GCAAGCTTGT GACCTCTAAC CTAGAAGTTC CAGAACAGGA AGAAAAAACA
15951 TGTGCGTGAC TAAAGCCACC CATAAGCACA GAAGCATTTT GATGTTCCAG
16001 ACCCGGGTCT CAATATCTGA GGAGGGTAAC TTCCTTTCCT TTATGCTCCT
16051 TGTGACCAAC TGGTACAGCA GTGATAATTT GTCCTCATGT AGGCAGGAGA
16101 ACAGCAGCTA GGGGTCAGTG ATGCAGGAAG CAGAACCATG TCCACATCAC
16151 CCGCGATGCG GGCGGGTTGA CCATGGGCGG GTTGACCACG GATGGGTTGG
```

FIGURE 3-6

```
16201 CCACGGACGG GTCAGGGTAT AATGAAGACA ATTGAGAAAT GAGCAGGAAG
16251 GACAAAAATA GAATTCTAGG TGAAAAAAGC CCTAGGTGTC TTTTTATTTA
16301 TTTCTAGAAT TAAATACATA CTTTTTTACC CCATAGACTT CACTCTGTTT
16351 GGTAGCCCTT TACTTTTACC ATCTGCCCTC GGCTCAGAAT GGAGGCAGGC
16401 GGAGGGACCA TATATCCTGG CCGTCTGCTC AGAGGCCAGG TGGGGCACAG
16451 TCACTCTTTT GGCCTCTGAT TTCCTAGAAC TGTGCTTCCA TTTCATGACT
16501 GCTCCCAGGT CCTAAGGAGG TTGGTCCGAG GACCGATTCT GGGGTTGAGG
16551 GTGGGCAGAG GGAAGGGGGA GTCAAGACTG TGTCCTGGGA GCTCCAGCAT
16601 CCGGTGGGAA CCAGGGCTGT TGGAGATGTG GCGGAGCTGC AGGTCCAGGC
16651 GGCTGTGGTT GCCATGGATC TGGACCTGGC TTGTGGCAGG AGAGGAGGCA
16701 ATTTTGTGCC CCTAATTCAC TATTCCTCTT CTCTCTCCAC TGCGCTGTCC
16751 TTCAGAACTG TGACCCTTTT GGCTCTGGCC TCTTGAACTC CATCCCAAAG
16801 GGAAACAAAC GGGCCAGCCC AAGAACAGTG CACAGTCGAG GAAGCTAGAG
16851 CAAAGAGCAT GTGGTCAGCC CTGCCTGTGG TCAGACTCGG AGGCACTGAA
16901 TTCAGATGGA GCATTTGGTG CTAGGGGCCA GTCATGCCCA GTTTCCCCTT
16951 AATAGCTAGT ATATTCTGTC CCAGGAGTTA AAAGCCTGTT GGAAGAGTGA
17001 ACCCTGATAT AAACTCTGGA CTTTGGGTAA TGATGATGAG TCAATGTGGG
17051 TTCATAGACG GTAACAAATC CACCACTCTA GTGGGAGATG TTGATGGTGG
17101 AGGAGACTGT GCATGTGGGG GACGTGGGGT ATTTGGGAAT GTTCTCGGGT
17151 ATTTGGGAAC ACCCTGTACT TTCCGCTCAA TTTTGGTGTG AACCTAAAAC
17201 TGCTCTGAAA ATAAAGTTTA TTAATTAAAA ACAAACAAAC AAACAACAAA
17251 ATGCCTGTTT GGGTGTAAGG CACACTGCCG AACTCCAAAC AGCGCTGGGA
17301 GTGTGGCCAG TGGTGGGGAG TTGAGAGGAG GAGACGCTGG TGTGAGGTCT
17351 GAGGTCTGAA TGAAGTCCGT TCTACCTGTG ATCTGCCTGC TCCCTGCTCT
17401 CAAGTCCTCT AATGAATAGA CTCTGTCTTC CTTCGTGCTG AGCTGCCCCA
17451 GCAGTTTCGA TCATAGTCTA GCATTGTGGT TTAGAGCAGC ACTTCTCAAA
17501 CTTTTATGTG CTTAAGACTC ACGCAGGGAT CATGTTAAAA TTCAGATTCT
17551 GATTCAGGGG GTCTGGGGTA GGACCTGAGT CTCCAGCTGA TGCTCATGCT
17601 ACTGGTCCGC ATGCCTGTCA ATACTTGGAG AAGCCAAGTT TTGCGGCTTC
17651 GGAGTCGCAT CCAGATTTGG GGTTTGAATC TGGGATTTGC TAATTAGTAA
17701 CTGTGACCTC TGGCAAGTTA TTTAACTCCT CTATGCCTGC CTCTGTTTTG
17751 TTATCTGGGT CCCTTCGTGG AGTTGTTATG AAAGGGTTCA GCCAGGAAAG
17801 GGGGCTAGGA GGGAGATGAT GAAAATGGAG ATTCCAGCCC CTAGAAGTGA
17851 TCTCTTCAAG ACCCCCAGCC TCGACTCAGT TCACAAGTTA TTCAAGCCTG
17901 ACCATTTACC CTTGAGCCCA GTACCCATTC AGCTAACAGT AAGTGTAGCA
17951 AAGAAACGGT TGCAAATAAA AAGAAACATT GAATCATGAC TGAGCAGTTC
18001 CTACATCCCT GCCCCCATGG TGGGGGTGGG GGGAGCCCTG CCACAGTAAG
18051 CTCTTGGGGG GCAGCTCAGT CCCCCACAAG CCCCCATGGC AACAGGACCT
18101 CCTTCCCACT GTGTTATTGC TGCAGATATT TTTAACAGCA ACACTTTTTC
18151 AGTGCTTTTT GGAGAAAGAT TTGTTAGTTA AAATGTGGCA TATTGTTGGG
18201 TGGTTTTTAA AGAATTGGAA ATAGCCACAA CATTTGGGTT GTGGCTATCT
18251 CAGTCCTTGA AGACATGAAA TATCAAGTAA AGGTTTGTAG GTGTTTTGGC
18301 CTGTTCTGTC TTCCACGGTT TTTAAAGAAC AGCAATTAGG TTTGTTGCTG
18351 AAATGCAGTA AATGCTTTAT ACTCCTTTCC CCAGATCTTC CTGTCTATGG
18401 ACATGGCCTG GCCCTTGTTG GCCTTCATGC CCTGTCTTTA CTCTGGAATG
18451 GGCTGGGTGT CAGATTATTT TATTCCACGC ATCCATAGTC CCTCTGCTCC
18501 TGCCTCACAG CATGACACAG TTGTGCTTAG TTAACGCATT TGTGTAATTG
18551 CTGGTTTAAA GCCTGTCTTC CCTCTTCGCC TGGCAGCTCC AGGTGGCAGG
18601 GCCGGCTCCT CTTCTTCACA GCCACATCCA TGGCATGTAC AGCCTCGCCT
18651 GCTCCGGGGT AGCTGCCCAG TGGACATTGT CGAGCCAGTC AGAATGGCCA
18701 CAGGTAGTGG GGACAGATTG GAGCTCCTTT GCCTAAGAAT TTGAGAAGGT
18751 GACTCCCAAG CAACTCTGCA ATATCAGGAA TCTTGATGTT GGTTTGTCTT
18801 GGCTTCAAGT CCCGGTTCTG CCACTTAGTG TGATTTTGGG CAGGTTTCTT
18851 ATGGAGCCTC AGTTTCCTCT CCTGTCAGAT GGGGTTATTT ATATGTAAGT
```

FIGURE 3-7

```
18901 AGCTACCCTG CAGAGCTGGT GTGAGGGTTC AATACAGTAA TGCACGTGGA
18951 GCCCATGGAA CGATGCCGGC ACACGGACAG CTCAACTAAG TGTTAGTTGT
19001 TAGATTTAGA TTGTTATTAT CAGAATCTGA TGGGGTGCGG TGGCTCACAG
19051 CTGTGGTCCC AGCCTCTCAG GAGGCTGAGA CAGGAGATGG CTCAAGACCA
19101 GGATCTCCAG CCCAGCCTGG GCAACATAGT GAGACCCTGT CTCTTAAAAA
19151 AAAAAAGAAA TAATGAATCT GCTGTTGCTA AATAGGCACT TAGAATGGCA
19201 CAGTCATTTC TCCTCTTGTC TTCAGTGTCC TGTTAATTTC TTTACAAATT
19251 AAAAAAATGT CGATAGCAGT CTTATTCAGA TACAGCTTCC TCCATCCCTC
19301 CTTGTCTTGG CAGGTGCCTT GCTCTGGGGC ACACATCAAA GCTGTTCTCT
19351 CTGCTGGGTG GCCTAGAAGG ATTAGTCTTC CTTTGCTGCT CCTTTCTTCT
19401 AATTCCCTTC CCCGGCTTCC TCCCACCTGG GCTCTGTGTG TGGCCTTCCT
19451 GGAGAAGGGC AGACGCCAAT GACTCCATGT CTAGGCAGAG GCCTGGGTGC
19501 CTGCACTTCT TGCCCTGTTC TTGGCCTTGC TGTGCTGGGC GGGGGCAGGG
19551 TGGTGTGGGG CATGGGGTGG TGTTGGGCAT GGGGTGGGGT TCTGGCTGAG
19601 GCAGGGCTCA GTGCCAGGCC CAGGCAGAGC TGAGTGGCTC CACTTCTCTG
19651 AGATGGTTGT CAGCATCATA CCTGCTGCTG TCCCGTTAAT TCCCCATGCT
19701 GCTGCTGTTA GTCACCTCCC TAATGGAGCT GGTCTGTAGC TTCTGGGACA
19751 GCTGATTTCC AGGGGATTAT TTGTATTACA CACTTTAATG CTTTTTAATA
19801 GCAAATTTTT AATTAAATGG AAAGTCCTTT TGGAAGCGAG GGAGCAGCAG
19851 CTGCAGCAAG ACTCAGCGTG AGGCACCGAC TTAGACCAGA GGTGCGCAAG
19901 TGAGTGGGGC GGAGGCAATG GCAGGACTTC GAGAGGACTT GATTGAGTGT
19951 ATATGGAGTG TGCCCAGGCT AATTTTTATG GGAGGAAGGC AGGGGCCTGG
20001 CGCTGGCTCC TTCCTCCTGT CCTAAAAGCC CCCTCTGTCA TCTGCAGGCC
20051 TAGGGAAGCA TCTTCTTTGC CCAGGAGAGA ATGTATATTG GATATATACA
20101 TTATATCCAA TAATGGGAGG GATATTGGAA GTATCACCTG CCTTTGATCC
20151 CGTTCCCAGA AATACTGAGA TTGGGATGGG ATTTTTGGGG TTGAGTCACT
20201 AGATTAGATC AAATAGTGTA GGTAATGGGA TGCGGAAACA GTCTTGAGGC
20251 CCTGGCTCCG GCCCTGGCAG GCTTCGGAGT CCTCAGTCAT CAAGGGAGGA
20301 GAACAAGGGG GCTATAGTGG TGGTTCAGTG CCTCGGGACT GTGCCGGCTG
20351 GGTTGTATAC TTTGCTTTCT GAATGATCTT GCTTCGTGGG GAGGGGACAT
20401 AGGGAAGCAC CTCAGCCCTG AGGAAACGTG TGACACTGGA AATGGAAGCA
20451 GCCAGGGCCC ACCCAGGAAG AGACATGGCC ATTTCTTTGT CTCCTAGCAC
20501 TGAACTGGTT AGTTTGGTGT CAGGCCATTC CTGAAGTGCT CCATGAGGTG
20551 CACCTGTAAC TGCCAAGGCT TGGAGCAAAG GTCAAACCGA GGGAGGCCTT
20601 TGGAACAGAA GTTCCCCATC AAGAGAGTTC ACGTGAGGGG AGGGACAGGA
20651 CAGTCAGCCA AAGCGGAGTC GTTTCTGCAT TAGAATGATG CTCAGGGGTT
20701 GGCATTTAAC CCAGAGGTGG CTTTGTGGGC AGAAACTTGA AGAGGAGACC
20751 TCAGAAGACT TCAGGTTGGT TTTTTACCCA AGAGCTTTGG AGGCGGGGAG
20801 CAGGGAGGGA TTCCGCCTGC CAGCTTTTTC TCGCAGCTGG TGCATCGCCC
20851 GAGTCTTCTT CCAGTGGCAC CCTCCCGGAC CTGTCTGCGA TGCTGCTTTA
20901 GGGACATTTG TAAGTGGTCT TTCTTTTGGA TGCCAGGGCT TTGTTGCCTG
20951 AATATGGGGG CTGCCCCACA TTTCTTAAGG GAAGCAGTGG TGTAGACCAC
21001 AGTCTTTGGA GTCAGGTAGC ACTGGATTCA CATCTTGACC CACCACTTAG
21051 AAGCTCTTTG GCCTTTGTTA AGAGACTTTG TGTCCCTGAG CCTCTGGTGC
21101 CCTCATCTGT AGAATGGGAA TAACATTCAT CTCAGGTGGT CGAAAGGAAT
21151 AATAAACTCC TCAAAGGCAG GCACTCTGTC TGTTCCTCCT GAATCCCGCT
21201 GCCTAGCGTG GGGTCCAGCA CATAGTAGGT GCTTGATAAA TGCTTGCAGA
21251 ATCAGTAATG TATGCAAGAG CCTAGCACAA GGCCTGGCAT AGTAAGCACT
21301 TAATAAGCTG TTATTGTTGT CATTGCCTGA ATGTGTGCGT GGCCTTCCAG
21351 GCTCACCATC CATTATCCTG CACCACGTGC CTTCCTGCTG AGCTCTGCCT
21401 TTCCACCTTC TTCCCCACCC CTTAGTTCTG CTCCCATTTA CTGCTCTGGA
21451 AGAGCTCTCT GGCTTTCCCA TCTGGTCATT GTTGTCCCCT GCCGTCAACA
21501 TTGCTAGGTG CTGCTCACGC TGCATCTCAC CATCGTGCAT CATATCCCAG
21551 GACCACCTTC TCGGAGACCA GCCCTCTGGG AAGGTTCCGG CTTTTCTCCA
```

FIGURE 3-8

```
21601 TCTTGACTTC TTAGCCATGA AGCTTTTCTC TCTTGCCTGA GTCTGAGGTG
21651 GCAACCAGAG CGCCAGGCTC TGGCTCCCAG GCTGCATAGC CTTGCACTGG
21701 GGGGCACTGG GCACGTCGCC ACTTCCCCCC ACTGCTCCTT CTGGAGAGCC
21751 CTGTGAGCCC GACAGGATGG GGCAGGGGTG GGGCTGCTGA GGAGAAGCCT
21801 AGGATTTCCA AGTTTTCTCT CTGTTAATCT CTGTCCCCAT CTCCTCTCTT
21851 GCAGTGCGCC TCCATGACAG TATTTCTGAA GAAGGGTTTC ACTACCTCGT
21901 GTTTGACCTG TAAGTGCCAC TTTCTGAGGG TGTGGGGCC TTTCCCTCTA
21951 GCTGACTCAA AATGAAGGCT CAGGAAGGGG CCTAAACAGG CTCTCCAGCC
22001 TCCGCCCAGG GCCCCCTCCT TTGTCCGAGG GAAAGGATTT GACTGGGGCA
22051 GATTGCTGCC CCCACCAAGG GGGTCTCCAT GTTCCCCCAG CGTCCCCCCA
22101 GGGCTCTGAA CCCCAGGACA GCATTCCTCT CGCACTTCTG TTCAGCAGCA
22151 CGCCTTGCAC AGATGCCTTT GTCTTGTTTC TCAGTGTGCT GTCCTTAGTG
22201 AAGAAATAAA AGACAGCTCT TTGCATGACC TTAAAAATCC TGAGAAATCA
22251 GAGGTAGCTT TCATTAGTCG GAAACCAGGC TCCATTGGAT TGGGTCTCTC
22301 CTCCACGTTG GTTGTGGTTT AATGTCTTAA AAGTGGCTCT TACCTCCTGG
22351 ACACTCCTCT CCAGGATTCT CAGGGTTGGG TCTCTGTGTC ATTGGTCTCA
22401 TTACTCTTCA ACTTCAGTAG TAGCTCTGTC CTTCCTGGGC AGCGATATTT
22451 TAGTGTTTAT GTTGGTCTCA AAGCTGTGAC TTTTGGGGTA GGTTGACTGT
22501 TTTCTCTTAG ATCCCTGTAT CTTCATCTCT GCCTGACTAT TAGTGAATCT
22551 GTGCATTTTG GAAAAAGAAA TGTCCGGAAG GAAGGGACGG CCCATGATAC
22601 CTCAAGGAGA ATCCGGGTGT CACTGAAGGA TCGAGTGTGT TCTGAGCTCT
22651 CAGATGAAAT GCATGGGGAG TTGGGATTTC TCTGAAAGCC ATTCTACAGG
22701 GTGACCCTGT TTCTTCTTGG ACATTGGGGT TGGACAAAGG ACCCTTTCTG
22751 CCTCTGACCC TCTTCTTCCC GTTGGTTGCA GTGTTACCGG CGGGGAGCTG
22801 TTTGAAGACA TTGTGGCCAG AGAGTACTAC AGTGAAGCAG ATGCCAGGTA
22851 GGATGAGGGC CCGAGAGTTC AAATGTAGCT CTGGAGTTTA GGACTGAAGG
22901 AAGTCTTGGC CACCTTCGGG GTCCAGCATT GTACCTGTTT GAATAGTCTT
22951 TGGGGAAGAT CAGAATAGCT CTTGTCTGGA GAAAGATTCT GTTGAGCTGG
23001 GCTAGGGCTT GCATACTGTG GGTGATATTA GAAGTTAAAA ATTCAGCACT
23051 TCCTAACCAG GCGCAGTGGC TCATGCCTGT AATCCCAGCA CTTTGGGAGG
23101 CTGAGGCAGT TGGATCACCT GAGGTCAGAA GTTGGAGCCC AGCCTGGCCA
23151 ACATAGTGAA ACCCTGTCTC TACTAAAAAT ACAAAAAAAT TAGCCGGGTG
23201 TGGTGGTGTG TGCCTGTAAT CCCAGCTACT TAGGCGGCTG AGGCAGGAGA
23251 ATCACTTAAA CCTGTAAGCG AAGGTTGCAG TGAGCCAAGA TCATGCCACT
23301 GCACTCCAGC CTGCGTAACA GAGCGAGACT ATGTCCCCCT CCCCCCCCCC
23351 CACAAAAAAA ATCACTTCCA AATGAATGTT TTACAAAGCT TTTCCAAGTC
23401 TCCTTTACCC TGTGACCCCA GAAATACTTT TTTTTTGCAC TACCATGTAC
23451 TCGCCACCAT GCCCAATGTC CCCCTCTGCC CTTTTCTTTC CTTTGACAAA
23501 TTCTGGTGTG CTCAAGCCAC TGTGCTGAGG CTCTGGCATG ATCCAGAGGT
23551 GCAGAAGACA TGGTTTCTGT CCTGAGGGAG TGGAGAGTTC TGGGCTGATA
23601 ATCCAACCAT AGAGCCCCGG GAGCTTTCAG CCTCTGTCAC CTTGTCCCTA
23651 GACCACCATG ACCAGCCTTG CCGTGGGGCT CCTCCAACTT GAGGACCGTT
23701 CCCCGGCCAC ATGCCTCAGC CTCTGCCCTC CTGGAATCC CTGGTGCCTC
23751 CCTCACCCAC GCTCTCAGGT GCCTGTTCAG CCTGCCTTTC CCGCCTTGGC
23801 TCTTCCCCCA GCCTTGCTTT TCTCGAGGGT GATGTCCCTA CAACCTGGTT
23851 TTGATCATCC TGCCTGCAGC TTATCTGGCT TATGTGGCAG CTCTGGCTGC
23901 TTCTGGAGAG TGGGGGAGTG CAGCTTCCTC ACGAATTTCT CAACCTTGAG
23951 AGGCCAATGT TTGCTGATCA ACTTCAGATG CTTCAGCCTC GGGAAGAATT
24001 CTCAAGTGGG GAGATGAATT CCAGTGCCAG CAGGGGAGGA CGAGGCTCTG
24051 GGACGGAGGA GGCAGTGATG GCTCAGGGAG CCTGCGGGGA GGAGGGAGAG
24101 CTATAGGGAG GGGGCCCTGA GGGGGGGGTGA CTGTACCAGT GGGCTTGGCC
24151 TGGCTCTGCT GGGACACTTC GCACTTTTGC CATTTTTGGC CAGAAGGCGC
24201 TCCCTGCTAG CCCGGCTCTG TTCTAATTAT ACATCTCTGT GGAGACTCGC
24251 CTCTATAGCT CAGTCTTAAA GTTTCTGTGG CCCACTCTTG GGCTGTGTCC
```

FIGURE 3-9

```
24301 TATGGGGAGG CCCGAGTTTC AGCCCCCAGG GACCCAGTAC GACCCCTTGG
24351 TTCTTGTGGC ATCCCCAGCA TCAGATTTTA GGAATAGTAA GTCCAGGCCA
24401 CCCAGCCCCA TACACTGGGA TGCTCTGCAG ATGTGCTTAA TATACCAGAT
24451 AGTGCCTGAT GACGGGGGTC TATATTCTAG GCCAAGTTCC TCAGCCTTGG
24501 TGCTACTAAC GTTTTAGGCC AGGTACTTCC TTGTTGTGAG GCCTCTCCTG
24551 TGCATTGTGG CAGACATTTA GAAGCATCCT TGGCCTCTGC CCACCAAATG
24601 CTGGGAGCAC CCCTCCTCCA GTTGTGACAA CCAGAAATTT CTCTAGGCAT
24651 TGCCAAATGT CCCCTGCGGT GGGGGGGGGC GGGCGGCAAA TTCATTCCCA
24701 GTTGAAAACC ACTGCTCTAG ACTGCCCCG CTCCCTGTCA GGAGTTTGAT
24751 GACAGGGATG GCAGGATGGT TTGCTATGTG GACAGTCTGA TTTACGTGTG
24801 TGACTGTGGC TGGGCGCAGT GGCTCACGCC TGTAATCCCA ACACTGAGAG
24851 GCCAAGGTGG GTGGATCACT TGAGCTCAGG AGTTCAAGAC CAGCCTGGGC
24901 AACATGGTGA GACCTTGTCT CCACAAAAAA ATACAAAAAT TAGCTGGGCA
24951 CGGTGGCTCA TGCTTGTGGT CCCAGCTACT GGGGAGGCTG AAGTGGGAGG
25001 ATTGCTTGAG CCCAGGAGGT CAAGGCTGCG GTGAGCTGTG TTCACGACAT
25051 TGCACTCTAA CCCAGGCAAC AGAGTGAGAC CCTGTCTCAA AAATAAAATA
25101 ATAAAATAAC TTTGGGTTTT TTTCTCTACG CAAAATCATC AGAAGTGCTC
25151 CTTAAATGCC CTGTTTGGAA GCTCTTAAGT ACATTGTTTC TTAAAGGTAT
25201 CTTTGTACTT GTTTTAGCTG CCTTACTGGA TGCCAGACCT CAGGGCAGCT
25251 ATTGGGTCTT GTCCATCTTC ATTATCCTAG GCACTCAATA AACATTTAGG
25301 GAAATGAATG AGTGCACCCA CCGCCAAAGT AGCTTAGGTT GTTTAGTTGG
25351 ACTCTCCTTC CTAAGTTGCC AGCACAAGCT TCTTCTCCAA GAACAAAGTT
25401 ACTGTATGGA GAAAGAGAAA GAAGGAAGGG ATTGGATGCT CTCTTCTTCC
25451 TCAGGATTCT GGGCTGTCTC CTGATCTCTT GGAAATGAGT TGGTTGTGTT
25501 AGACCTTTCC AGTCAAAAGG GGGTGAGAGG AACCCGTTCT AGCGGTGATC
25551 CTAGAAAAAC CATTGCATCT GCCTGGGCCT CGGTTTCCTC TTTCTTTAAA
25601 TAGGTTGAAC AAGATGATGT GCAGAGTCTA AGGTTCCAGT GGCCGTTAAG
25651 TGATTCTCTG TGAATCCGTG GCCCCTTGTC ACATGCCTTA GTCTGCAGCA
25701 TGTGGTTGTG GATGTGGATG AGGTGGTTTA ACCCTGCGCT AACATTTCTT
25751 TTCCTTCTGC TTTTTTAGCC ACTGTATACA TCAGATTCTG GAGAGTGTTA
25801 ACCACATCCA CCAGCATGAC ATCGTCCACA GGGACCTGAA GGTACTACCC
25851 AGGCTCCCCT CCGTGCCTCT GCTCATGAAG TGTTGGCGCC ACCTGGTGCC
25901 AGATAGTGGT ACTGCGTAGG CCCAAACTAG GCTTCCTCTG GGCTGCAGGG
25951 TGGGTGCTCA CAAGGTTCTC TGTGTTTCTT CTGCAGCCTG AGAACCTGCT
26001 GCTGGCGAGT AAATGCAAGG GTGCCGCCGT CAAGCTGGCT GATTTTGGCC
26051 TAGCCATCGA AGTACAGGGA GAGCAGCAGG CTTGGTTTGG TAAGGGTGAT
26101 CCTGTCTTCC CGGAATGCAG CCCCCGCCCT TCCTCCTCTT CCTGATCTGC
26151 CTTCCTCTAT TAGAACTAGA AGCCAGACCC TTAATGGTCC TGGCCTCCGA
26201 GATCTCTCTT GGCCGTACGC GACTCAGTAC AGTAAGTCTA GCTGTTGTCA
26251 GCACTGCTTT CTTGCTGCCT GTGGGAAGGA GCTGGAGTTC CTGGTAGGCA
26301 TACGGCTTTG CCGTCTGGTT CAGATTCCAG GCGCTACAAG AAGCCCAGCC
26351 TGTCAGCTCT TGCTGCCCAT GTGCTGAGAG TTTATGTAGC AAAAGCAGCA
26401 GGAATAAGAT GGGACTTGGG GGAAATGGCT GGTGTGGATT TAACGAGAGA
26451 GAAAGTGGGT TCAGTATGCC TCTGCCCTCT CTTTTGCTAC AGGTTTTGCT
26501 GGCACCCAG GTTACTTGTC CCCTGAGGTC TTGAGGAAAG ATCCCTATGG
26551 AAAACCTGTG GATATCTGGG CCTGCGGTAA GCCCATTCCA CGCTCTCAGC
26601 TTTTCGCTGT TAAGGGCCCT CAACTTCCGA TGATGGCAAG AAAGAGGCAT
26651 CGCTATTCCT TGCAGGTCAC ACACGTGCCT GGTGTATGTG AAATTATGGT
26701 GTTTGCCCCT GGGATGGCTG TTCCCATCAC ACCCTCCTCC CTGCGTACTT
26751 CTGGGATGAC ATTGTATCCT TCTTGGAGAG GGATTTGCCC ACGCCTTAGA
26801 GGATGGGTTG TGCCTAAAGA AATCCCTGGT GTGACTTGGT GACGTGAAGT
26851 GTGAGGCATA GCAGGAGGGG CTGGTAGCAT AGCATTATCG GCTGGCATCC
26901 ACTTCTGACT CTGGTATGGC CCCTGCCTTT CTAGGTGGCT CTGAGCCCTG
26951 CATGGTTTTT CTTGGTTCCT CAGGGAAGTA GGCGACTGAC CCCCATGACC
```

FIGURE 3-10

```
27001 TGTGTGTTCT GTCTCGTAGG GGTCATCCTG TATATCCTCC TGGTGGGCTA
27051 TCCTCCCTTC TGGGATGAGG ATCAGCACAA GCTGTATCAG CAGATCAAGG
27101 CTGGAGCCTA TGATGTAAGG ACCAGAGAGC CGGGCAGCCA GGCCAGGAAG
27151 GGCAGATGTC CTGCTCCTCG GGCTCTGTCC AAGGGAGCAG GCTTGTTTAG
27201 TGTGTCACGT GATACGGGGG TGTCAGGGGA CTTTGAGGAC CCAGGAATGG
27251 GCATCCAGGG CCCAATTCTT GCCACTCTAT GTCCCAGGGA GCAACTTTCT
27301 TTTGCACAGC CTTCTTCATA ACTAAAATTG AGGAGTCCAC TGAAGTCCTT
27351 TGATCTTTAC TTGCAAAGAA TGGAGCGGCC TCATTGGTGT GCTGTGTAAC
27401 ACAGGGACAA AAGGCCTGGA GACTCCCTCC ACTGCAGTGG CACCTTGGAC
27451 ACATTGCTGA GCCTCTGTTC CCTCCTAAGT ATAGAGCTGG GCTTAAACCA
27501 GAGAATGTTG GAGTCCCCTT CCCGCTCTAA TCTGATGTTC TGGCATTCTA
27551 AACATGACTG TTCTGTCTGT CTTTCCAAGT CTTTAAGTTG ACACAGGTTC
27601 TGGAATAGCC GCAGGGCTTC TCCAACTCTG CCAGTCACAG CTTTAGGTAC
27651 CACAGAGTAT CCCAATTACA GGAGTTGAGT TGAAGACAGA ACCAGTGTTG
27701 CAGGGTATGA AGCTCACCAA TACCACATTC TTCTCCCTAT TCCTGCTCCT
27751 TAGTTCCCAT CACCAGAATG GGACACGGTA ACTCCTGAAG CCAAGAACTT
27801 GATCAACCAG ATGCTGACCA TAAACCCAGC AAAGCGCATC ACGGCTGACC
27851 AGGCTCTCAA GCACCCGTGG GTCTGTGTAA GTGTCTTTGC TAGTGGCCAA
27901 GGAGCTCAGG GGTGTCAGCC TTCTGTGTGC CCTCGGCACC ACCCCCTCCT
27951 TCTTACCAGC AGAGATTCAT TCTGGGCCCC AAGCAATAAC TGAGCAGGCG
28001 GGCAGAGGAC TGTTGAGGGC CAGGGTCAAT AAATGTCACC AGGGAGACTC
28051 GGGAGGCTGA TGGGGCTGGT GGGCCACTGC TCCTCTCTCC CCCACTCATG
28101 GCTGTCAGGC TGGGATTGGT TCTGTTCTTG GATGAGGGCT CAGGTTGACC
28151 CTTGTGGACT CCAGGTAGCC GGTGATAGAA AGCAGCTGGC AAAACCCAAA
28201 GTGAATTCCC AAGCTGGGGT TCATACTCAG ATCTCAACTC CACTGGAGTG
28251 GTGACCAAGA TCCAACAAAT CAACAGAAGG GGTTTCTGAG TCATTAAAAG
28301 CATAAAAGCT GAGGCATAAA GCTTCTGCGC TAAAGTCCTA GGAGAGTCCT
28351 CTAGGCTATC AGTGTGGGTT GACGTACTCT GTTTTTATAC ACAATTCTTT
28401 CAAGCTGAAA TATCAACTTT CAGACAAAGA AGAGGATTTG GTAGAGTTAG
28451 GCATCTTGAC AACCACGAGG CATTATTTAT CTGTCCATTC TGTGTTTATT
28501 AAATACCTCT TTGGTGCTGG TTACCGTCTG GGTGCTGGAG ATACAAAGAT
28551 GAATGAGGCA TGGTCCCTGC CCCAAAAGAT CATCTAGGGA GACAGGCACT
28601 CAAACAGGCA GTCATGTTAC AATGTGACAA GTAGGTACAA GAATCTAATG
28651 AGAGTACAGG AGCTCCTACT GTTCCTGGTG GGTGGTGGGG TTACTGAAGG
28701 CTGCACGGAG GAGGTGACAC CCCTGTGCTT GTTCTTGGCA AATAACGAGG
28751 TCCTCAGAAC GTTAACCTGC AGACAGAGTT TAGCACAGTG AGAGGTTATG
28801 GGAAACTATG GTGAGTTGAA GGAATGTTGA GTTGTTTGGT TGTCGATGAG
28851 GCTGCAAATA TCAGAATGCA AGAGAATGGG GCAAAAGATT CCCTGACATA
28901 CAAGTTTCTG CCTCAGGAGT TTGGATTTTA TTCTGAAAAC ATAGGGAATC
28951 ATTTAAGGGT TTTAAAGAAG AATGAAATTT GCATTTAAGA ACACTTTGGA
29001 AGTTGTGAGG AAATGAATTG CCAGGCATGG TGGCATGTGC CTGTAGTCTC
29051 AGCTGCTGGG GATGCTGAGG CAGGAGGATC ATAAGCCCAG GAGTTTGAGG
29101 CTGCAGCGAG CTATGATTGC ACCTGTGAAT AGTCATTGTA CTCCAGCCTG
29151 GGAAAGATGG TCAGACCCCA CCTCTTTAAA AAAAAAAAA AAAAAAGAAG
29201 GGAATTGAAA ATTTTTAAAA GAAAAGGGCT GGAGACAGAG AGCTCAGGAA
29251 GCTTTTTTAA TAGTTGGAAT AGTCTAAGCA AGACCAGGTG AGGTCTCAGC
29301 AGAGGGTAAG GATGGGGGAA TGTGCAGTGT GTTGAAATTC AAGAGATATT
29351 TGAGAGAACC TAAAGGATTT AATTCTCTCC AGTTGGATTT GGGGGGAGCA
29401 AAGAAGAGAG AGGCCAGGTT TCAAGTTGAG CGGAGAGTTG TACCCTCACT
29451 GACCCAGAAG AAAACCAGAG GAGGAGCTTG TTTGTGAGAC AAGACGATGG
29501 TTTTCTCTTT TTTTTTTTTT TTTTGAGATG GAGTCTCGCT CTGTCGCCCA
29551 GGCTGGAGTG CAGTGGCGCG GTCTCACTGC AAGCTCTGCC TCCCGGGTTC
29601 ATGCCATTCT CCTGCCTCAG CCTCCCGAGT AGCTGGGACT ACAGGTGCCC
29651 GCCACCACGC CCGGCTAATT TTTTGTATTT TTAGTAGAGA TGGGGTTTCA
```

FIGURE 3-11

```
29701 CCGTGTTAGT CAGGATGGTT TCGATCTCCT GATCTCATGA TCCACCCGCC
29751 TCGGCTTCCC AAAGTGCTGA GATTACAGGC ATGAGCCACT GCGCCCGGCC
29801 AAGATGATGG TTTTCATTTT GTGCCTGCTG AGTCTGGCAA CCTCCAGCCA
29851 GACACATTCA GTGGGTGGTT AGAAATATGG TCCTAGAGAT TAGAAAAGAA
29901 GCTAAAAATT GGAAATCCAC ATTGTAGTCA TTTCTGTGTA GTTGGTAGTG
29951 AGGCTGTAGA AATAGCCTCT TCCTATGCTG TAGATGGGCC TGTTCCTATG
30001 CTGGTTGAGT TCTTACGGTG AGCTTCTATT GGCTGTAGTA GAGAAGAGAC
30051 GGCCACTACA CACCAGCATT TAATGATAGG GAGAGTTAGG GGGCCCAGCA
30101 AAGAGCACTG AGAGTGAGAC CTTCCAGAAG ACCCAGAAGC TAAGAAACAG
30151 GGGGTCTCAG TAAGGGAGCG TCAGGAATCA GATGCAGAAG AGTCCCTGAT
30201 TAAGTTGGGG AAGAATCCCC TGGCTCTGAC CATTAGATGC CATTGTTTCA
30251 TCATTTCACT GAGACAGTGG AGAGAAAGAT GAAACCCTGT TTTCAGTGAG
30301 ACGAAAAGGG AGTGAGGGTG AGGAGGGGCA TGGGGAGCTA GGCATTGAGG
30351 TGGGAAATAA ATGGTGATAC TTAGATTAAG ATGGGCCAGG GGAGCTTTTA
30401 ATGTAAGGCT CACACCTGTA ATCCCAGCAC TTTGGGAGAC CAAGGCAGGC
30451 GATCACTTGA GGCCACGAGT TCAAGACCAG CCTGGCCAAC ATAGTGAAAC
30501 TCCATCTCTA CTAAAAATAC AAAAAATTAG CTGGGTATGT TGGTACACAC
30551 CTATAATCCC AGCTACTTGG GAGGCTGAGG CATGAGAATC ACTAGAACCC
30601 AGGAGGTGGA GGTTGCAGTG AGCCAAGATA ATGACACTGC ATTCCAGCCT
30651 GGGTGACAGA GGGAGACTCT GCCTCTAAAG AAGAAAAAAT TTCTTTTTAA
30701 AGATTATATT GGTCAGGAGC GGTGGCTCAC ACCTGTAGTC CCAGCACTTT
30751 GGGAGACCAG GGTAGGTAGA TCACTTGAGC CCGGAAGTTT GAGACCAGCC
30801 TGGGCAACAT GGCAAACCC CATCTCTACA AAAAAAAAAA CTTTAAAAAT
30851 TAGCTGGTTG TGGTAACGTG CCTTAGCTAC TTGGGAGGCT GAGATGAGAG
30901 GATCACCTGA GCCTAGAGAG GTGGAGGTTG CAGTAAGCCA TTATTGTGCT
30951 ACTGCACTCC AGCCTGGGCA ACAGAGTGAG ATGCTGTTTC AAAAAAAAAA
31001 AAAAATTTTT TTGTTTAAGG AGAGGCTTAA CTATAATCTA TAGAGAAGAA
31051 TCTAGTCCAG AGGAAAGAGT TGAAGATCCT TGCTAATTGA GGAAGCAAAG
31101 GTTTGGACAG CAGAAAAAGA GAGGGGGCTC CTGAGCCAAG GGCAGGGGT
31151 CCATCCCGGG GATGACCATG ATCCCCCTGA GACTTCTATT AGTGTGGAGG
31201 CAGGTGAAGA TCGGCTTGTG AGTGGAAGTC TGAGCTGAAA GGGGTTCTTG
31251 CTGATGACCT CTCATTTTGC TTTTGGAGAA ATTTACACCG AGGAGGAGGT
31301 AAAATGAGAG ACTTGGGGAA GGTAGAGAAG GTGGGGAGAG TTGCCTCCGG
31351 ACCTGGAAAG AGTGGGCCAA GGGTGAGGGA AGGATGCGA GGAGGCCCCG
31401 TAGTGTTGGT GGGCACCTGG CTGCAGGTGC CAGGATTTGT TTTTCTGACA
31451 GGCTGGTGAA GACAGCAACA GCAAGGGGAG AGGGCAAGCA ACCTGAAACA
31501 GGCACCCAAG AATGGGGGAA ATATTCTGTT CTGGGGTCAT TTTTGCAGGC
31551 CCTACCCTCT GCAGTCCCGT GTGTCTCGAG CCCCTGAGGA CATCACTATA
31601 TTCTGAAATT ACATAATGAT GCTGGTATTG ACAGCTGAGT CATTGAGGAA
31651 GTGTAGACTG TGTCCCATGG ACTCTGTTTA AGGAGGCCAG GAAGTTAGCA
31701 GTAAATACAT TGAAGACAAA TTTCCATCCA AAAAAGGCGG GGCACAGTGG
31751 CTCACACCTG TTATCCCAGG ACTCTGGGAG GCCGAAGTGA GCAGATCACT
31801 TGAGGTCAGG AGTTCGAGAC CACCAGCCTG GCCAACATGG CCAACCCTGT
31851 CTCTACTAAA AATACAAAAA TTAGCTGGGT GTGGTGGGAT GTGCCTGTAG
31901 TCCCAGCTAC TCGGGAGGCC AAGACAGGAG AACCTGAGAG GCGGAGGCTA
31951 CGGTGAGCCG AGATTGCACC ACTGCACTCC AGCCTGACTG ACAAAGCGAG
32001 ACTCCATTGC AAAAAAAAA AAAAATTACA TCCAGAATGA TGAAAAGAAT
32051 TGATGCTTCA AGGTGACGAT CCTTAGCTTC TGGGATCATG GCTTCATTCA
32101 GGACCTTGCT GGGGGTGTGT GGAGAGGGGC TCTTGGAAGG AAGGAATGTC
32151 CTCTGTAGAG AGCAGGAACC CTGCCGTTCT CTCGCTGCTG AGCATCTGGA
32201 ACGCAGTAGG TGCTCAGTAA ACAGCTGCCT AAGGAGTGAC TGAATGAGGA
32251 TCACAGCCCC CAGGGTACTC TCCTGTTCGG TAGCCTCTGT TTCCCAAGGA
32301 AGAATAGGAC GGTCTCTCAG CAGCCCGTCT AGCATCCGTT ATGGTGTTCT
32351 CACGTTCATG TTGTCCTTAT GTAACCTTGA GTTTCGGGTA GTGCTTTTAT
```

FIGURE 3-12

```
32401 TCTAAAAGCG TTTTCACATC TGTGACCTCA TTTCATCTTC AGAGCAACTC
32451 TGGGGTGGCT GAGTGCATGA CCCTGTCCTG GGCATGGTAT CGGTGCCAGG
32501 ACTGTGGGAG GCGCAGAGGA TCTGGGCTGG GGCTCATAGC CTGTCTGTTT
32551 GGTTTCTAGC AACGATCCAC GGTGGCATCC ATGATGCATC GTCAGGAGAC
32601 TGTGGAGTGT TTGCGCAAGT TCAATGCCCG GAGAAAACTG AAGGTGAGTG
32651 TCGTTTCTAG GCTGCCAGCC TCCTTGACAT CATGCCTTGC ACCAGTGTGG
32701 CTCCTGCCCC ATTTCAGAAG GAAGCTCCCC TCCTGGCTGG AGCTGGGCTC
32751 TGAAGGTTGT ACATGTCACA GGGGAGGGGG CCCAGAGGCC TGATGTCTTC
32801 AGGCTCTAGC CAGGACCTGC CTTTGCCTGA GACCAGCCTG CCCTTTTCTA
32851 GGGTCTCAGT GAATTCACAG GACCTTCCTC TTTCCCCAGG GTGCCATCCT
32901 CACGACCATG CTTGTCTCCA GGAACTTCTC AGGTATGTTT TCCCAGCTGT
32951 GTACTTTGAT TATGCCGAGG TGAGTGGATC AGGAATGGGC TGTTGCCATC
33001 CCGGGCACCG CTGGGTTTCC TCGGCGTCCT GGGCCACACC TTGACCAGGG
33051 CGAGTGAGGA TCCTGTTTTG AGGGGCTGCT GCTGCTGCTG AGTCCTGCTC
33101 CTGAGATTCA GGGGGCTGGA CTCACATTTG TGAATTGTTT CCTAGAACTT
33151 CCCAAGGAGT AGCCTGCCCA ACTTGCTATG TACCTTGTTT CTCTGGATTC
33201 TTATTTAACT CTCTGAAGAC TCTCAGCACT TTACAGATTT TAGCCATTCT
33251 AGGATCTTGG AGGATGTGCT GGGGAAGAA AAGAGAGATG AGGTACAGTG
33301 AGTCTTCTCA ATTGCCAAAT TGCCACCATT CATTTGCCTG CTGGGACGAT
33351 CTCTTACTTC ATTTTGTCCA AGTGGAGATG ACTAATAGAA ATTATTCCAG
33401 ATGTTTAAAC CTTTTGTGGC GACTTGTGCT TAAAATAGTC CCTGAGATAC
33451 TAGCTATAAC AGTGAAGAAA TAAAGACCAG CAGGAGAGAG GGAAAGGAAC
33501 TTGCTTAAAT TTGCATAAAG AATTGGGAGA GGTGGGACCA ATAATTTGTA
33551 AATCATACTT GACATTTATT TTTAAGATGC AAGACACTCC ACTCCCTCT
33601 TGCCCCCACC CTCACCCCAA CCCCTATTAT TGTTTGCCTT CAATTGGGAA
33651 GCACAGTGGC TTTTTTGTGA GGAAAAGATT AATGTCGAGA CTGAAGACAG
33701 AGAGGGCTCT GCCCAGCTTG CCATCTCCCC CGGTCCTCCC TCCCTCTAAC
33751 CCCTTGCCTC ACTGTTTTGG TTCAAGACCC CCCCTTCTCC TTCCCATAAT
33801 AAGACTCCCT CCCTTGCTTC CCCTCTGCAC CACCATGGAA AGGGGGTTGT
33851 GTGGGAGCCT AAGCCACCAC TCAGTGGGAG CCACTTCTGA ATACCCGTCC
33901 TGCTGGGCTC GCCTGCGCTG GCTCCAGGTA ACGCCAGGGC CTTGGCTGTG
33951 AGGATGCTGC AGGCAGGGAG CCTAGGGCTT CGTGGTGTAG CCTGAGAGCC
34001 ATGGAGCTCC GGAAGGCCAG GGCTGGATAG TGAGCCCGGG GCTGGTGGTG
34051 CCCTGCCCTA GGCCTTCTCC TTTGACCCTG GTTTGGGGCT TGATCTTGTG
34101 TCATGGGTAC CCACGACGGG CATACTGTGG TGTGGCTCCA CCTCTCGCAG
34151 ATGGAACAG GGAAGCGTGG CTGGCTGCCT CCGGTGGAGT TGCAACTGTA
34201 GTCCCACACT TGCTTCTTGT GCTTTAATGA CGCAGCTTCT ACTTTTTGGG
34251 TCTACGAGCC TTTCCAGAGG ACATTGAAGG GCGTTTCGGT GTTGCCCCTA
34301 GAGCGAAGCT CTGTCCTCTC TCCCCTCTGA GTTAAGAAA TGTGAAGACA
34351 GTCTGCTGCT TCTCTTTTAG CCCAGCCAGT CAATAGCAAG GCCCTGTCT
34401 TGCAGCCCCG GGCCTCCACA TCAGCCTCCC CCTCCATTTC AGGAAACTGG
34451 CATCCTGGTT TCAGGAAATC GGGTGTTAGG ACAAAGCATT TTATTCATCC
34501 CTGTAGAGCC TCCTGTTCTT ATTGGCCAGA CCTAGACTGG CCTTTGAGCT
34551 CACTTTGCCT TGGGTCAGAG GAGACAAACA ATGTTGCAAG CATTCCAGGA
34601 TGGCCTCTTC TGCCCTGACT CTGGGACAGG TGAGGACAGA GTCTGTCCGG
34651 AAGCTTCTGC AGAAAGAGGT GTCTATGGAT GCAATCAAGA AGGAAGGGCA
34701 CCTGTGTGTT TCTCTAGGGC TGTTTTTTGA GTTGACCTCC AATAGGAGAT
34751 GTGGCTTATC CTGGACTCTA GCAGTTTGGC TAACAGCGAA TCGGGCCCTC
34801 CAGAGTGTAT TGCTTCAGCA GCCTTTGTTT TCTTTCTCAG GGTTTATTTC
34851 TTGGGCACCT TTCACCTCAG CACACTGTGA CACACAGACT GAGAATGCTG
34901 CCTCTCTCGG CTACCTCCCT TAAGACAGGG ACCTGTGTCT CTGAGGGGTT
34951 GGGGGGCATG GAGCTGGGC CCACCAGTAA ACTTAGCTGC ACAAGGGCCA
35001 CAGACCCTCC CTGGGACCCC CACGCCAGTC CCTCTAGTGT GTGGGATGTA
35051 GAGAGGGGAG AGGGCTGCTC TGCGCCCCCG GCACTCTCAT CGTGGGCTCA
```

FIGURE 3-13

```
35101 TTTAGCTTCT AGGGAGGGAA GGACTAGAAG GGAGGGCGTT TCATCACAGC
35151 CTTAAGCTAG GGCCGGGCTA CCTCAGAAGG GGCACCTGCC TCTCACCGGC
35201 TCAGGCATTT CGCTGTGGAC CCTCCTCCGG AGGGGGTCAT GAGACAGGCA
35251 CTGCAGCCCT CTCCATCTGG TGGGGACGCA GTGTTCCCTA TGCCCTGGCC
35301 CAGCCCGGTC TTCCCAGGCC CCAGACTGC TGCAGGGCTG GCTGCGCCTA
35351 CCTCCTCAGC CTGCCCCTGG CGCTCCGCTC CCCCAGCTCG GCTGGCTTGG
35401 CCACGCCGCC TGGGCTGCGC CTCGCGCTGG GGCATGCTCG CTGCTGACGG
35451 CCCCGTGGCT TTGCGGGGCT CTGTGCACTG AGAGACTGTA TCCCCTCAGT
35501 TGGCAGGCAG AGCTCCGCCC CCGCCTCGCC TGCCGCGAGC GCCGCCGGCC
35551 TGGCCGGGCA AGGTACGTGG CATGAGTCCT CCCCGACCGC CTGCCTCGGC
35601 CCCCTGCCAC CCCACCAGGA GGGCCAGCAT GCCGGGCCCA CTCACCAGGG
35651 AGGCGAGTCC CATGCTTGCG GGCTGAGATG GCATGCCAG ACAGACTACC
35701 TAACTTGGCA TCTGCAAGCG CATCGTTGTT ATGGAGCCCC CTAACCAGCC
35751 ATGCATGCTG GGCGCTTGCC AACTTTCAGG GGGCAGTAGC CTGGGGGCAT
35801 GGAGCTGGGC AGCGGGAGCC TTGCCAAGAG CCCGATGCCC TGGGAGGGCT
35851 GCAGCCAACA GTGGGCCCTC AGAGACAGTG CTGGGCATTG CCCTGAGCTG
35901 CCCGGTGCTA GGACTAGATT TCCGCAGCAC TGTTTAAGAC CCCACAGAGG
35951 AGCCGCGCTC CTCAAAATTG TGAAGTCTGG CGCTTGCTGG CCTCCAGGTC
36001 TGAAAGGCTC CAGAGTGCAG AAGCCTCAGA GCCAGCTGTT TCTGGGTTCA
36051 CATCCTAGCC CTGCCACACC CTGAGCGAGT CACACCAGCT CTCCCAGCCT
36101 TAATTCCTCA CCTCTCCAAT GGGGATGATA AATAACATGG TGGTGCTTAA
36151 GATCACCCTG TCGAAGGCTC TCAGCCCTGC CTGTGCAGTA CAGCTGTTAC
36201 CTGGGAGCTC GTAAGAAGTC CTAATGCCAG GACCCCACCC CAGACAATAA
36251 AATCAGACCC TTAGGGATAA GATAGGTAGT ACGCTTTTTT TAAGCTCCCA
36301 GGTGATCCTA GTGGGCAACC AGCGTTGAGA GCTGGCTGGT GAATGGAAAG
36351 CACTTAGACA GTAGGCGGTC AGGCACAGGA GTCAGCACAT TTAAAAAACA
36401 ACATTCAAAC CCAGCACGAC AAGATAAGAT CAAAGGTCTT TTTCTGGAGT
36451 CAGAATTCTC GTAATGAAAG GACCCCTGTT CTCACTGGAG AGAGATGGAA
36501 CACAGCTTGG GGAGGAATGG CTACCCAAAG GGCAGGAGGG TGGCAGCAAT
36551 AGTGACAACG ATGGTGGACA CTTACTCAGT ACTTGCTATA TGCCAGGCAC
36601 TCTAAGTGCT TTTCATGCAT AATCCCACTG GATTCCCACC ACTGTTTTGT
36651 GATGTCAGCC CTACTTTATC CCATTTTATA GATAAAGAAA TTGAGGCTCA
36701 GAGAGGTTAA GTAACTCACC AAAGGTCACA CAGCTGGCAA GTGGTGGAAC
36751 CAAGATACAG ACCCAGGGCA GGCAGTCCAG GTGTATCAGA CAGTTGGGCT
36801 GATTCCATCT CCCTGTGCCT CCCAGACTCT CCTCCCCACT GTCTGCTACC
36851 TTCCTGTGGC CTTTTGTGGC CAGCTGGTGT CACCAGCCTT CTGGCACAGA
36901 GCTCATCAGC CTGGAGCGTC ACCCTATGCC TGGCTAGAAT CTGTTTGACA
36951 GCTCATTATT CTGCCGAGTC CTTCCTGCTC ACAGGTCCAG AGAGTGGACA
37001 CTGGGGAAAG GGTGGCAGCT AGGACCCAGT GAACCTGGTG AGGACCTGCT
37051 CAGTGAAGGC TTCAACCCCC TGGCAAAACC CTCCTGTAGG TGGTCCTGGT
37101 TTCTGTGTCT GTGTCTGTCT GTCCTCTGGT CTCCTGTGTG AACTGTGACA
37151 CTCTGCTTCT TGAGAACACT CAGGAGATGT CTTGCATCCT TGCAGTTTGG
37201 CCATCCAGAG AACTTCCATG GCACCTAGGG ATGGAGCCCT CACTCTTTCA
37251 CCCTGGCACT CTGCTTCCAG GCCTGGGTGG AAGCTGTCAA AGGCAGAGTC
37301 CCCAGTGCCC CAGGCGGCTC CAGTACTGAG CATGGTTTCT CCTCTAAGTG
37351 TCGTGCATCC ATGCCCTCCT CCACGCAGAG GAGATCCTGA GGTGCCACCC
37401 TGAGGGCTCT GACGCCACTC AAGATCCCT TCTTGCTGAG AGGCTATAGG
37451 AAGTGCCTCT TTTGGGGGTT TCGGGAGACC CTTGGCCCCC TTGTCAGACA
37501 CAGCACTCTC TTGTGGATCT GGCTGCCGGA CTTCAGGTTG GGGAGAGGGT
37551 ACAATGCAGG AGACTTGATA TTCCTCTTTG TTTTCACAGC TGCCAAAAGC
37601 CTATTGAACA AGAAGTCGGA TGGCGGTGTC AAGGTAAGTG TCTCCAGCCT
37651 CTGAACAGAC TGGCCTCTTT CTCCCCGCAG TCACTATGGG AATTCTTGGC
37701 ACCTGGTTCC CCCTTTCCCA GGGAATCTTC CTATCCTTGC TAGTCTGCTT
37751 TAAACCAGAT GCCTTTGTGC TCAGAACAGA AGGTTCTGCT GGCCTGAGAG
```

FIGURE 3-14

```
37801 GGAAGTAGGG AGGTATTTTT CCTGGCCCTA GCTGGATGGG AATGACTCAG
37851 GGGAAGTGAT CCAAATCATA GTTTATACCA GAGCTGAATC CGGAACCTGA
37901 CTTCTACACG GATGCTTCAT CTCCAGGGCT TGACTCTGGG TTTTTTAGGT
37951 CATTTGGTTA TCTTTCTTTT TTTCCTTTTT AGAGCACAAA TCCTTTTAAT
38001 CAAATGAAAG CCAAATTTGC CTGAGTGATT CAGGCAGGGT ATAGGGCTTG
38051 GAACCTGAAA CCACTCTCCT TTTGGTCTTT TTCCTTCTCT CTACAACACT
38101 TTCAGATCCC ACTGAGTGCA ACAGCCTCGA GCTTTCTTGA CGCATAGGCT
38151 CCTCAGAAAA AGGCAAAGGC CATGGTGGAT CACGGCTTGT TCCCACTGGG
38201 TGAGGGAGCT TTTCCCATGG GACTGGGGCA AGAGGAGGGA CCTGGGACCC
38251 ACCAGGAGCC CTGCTGGGAA TGGCTGCTTG GCCAAGGTAG AGGAGAGGTG
38301 ACTGGGGCTA CCCACAGGGC CAAGACATT CTGTAGATGC TTTGGGGGCA
38351 GAAAGGATCC TGGGGCTAGG GCATTGGGTA GGAGCTCATG CTATCTTGAA
38401 GCCTCCCAGC TTACACTCTA GACTAGATTT TCACTGGGCC TTTTCCCAAG
38451 ATCTTGTGTC AACAGCTGAG ATACACACAC AAGCCCCGTT CCCTCCCCGT
38501 TCCCTCCCCA CTCCCTCCTC TTTCCCTCAT TCTCTGCATG CCTGCTTCTG
38551 TGTTCTTCCG CCCCTCGCAG GGGAGCCTGG GCTCCGCGCA CACCCTCTGA
38601 CATGGAGCTG GGGCATCGT GCGGTCCCCA AGCTCTGCCC CTGAGCTACA
38651 TGGATGGAGC CAGGTGAGGA AAAGGGGCAG GTTTAGTTGG AGAGAGTGTT
38701 TAATAAGTAC CTGTCAGTCA GATGTCCACG CAGCATTCTG TTCTGAGGGG
38751 TACACAACAG AGGTGTAAGA GGGGGTGTGG CTTTCAGTCG CCATAGGAAG
38801 GGGGCCGCAC CTGGAGTCAG CTGAGCGCTG CTAGTGGACC CACGCGAGAT
38851 GGTTTAGTCC AGGAAGCTCA TAGGAGAGAG CGTACTGGAG AAAGCTGCAG
38901 GGACATAGGT GAGACTCACT TTGCAGTTTT ACTTTCTGCT ATATGTTTTC
38951 TTTAAATTGA AAATATGGGT CAGGCTTGGT GGCTCACTCC TGTAATCCCA
39001 GCACTTTGGG AGGCTAAGGC GGGTGGATCA CCTGGGGTCA GGAATTCAAG
39051 ACCAGCCTGG CCAACCTGGT GAAACTCCGT CTCTACAAAA ATACAAAAAT
39101 TAGCCAGTCA TAATGACCGG TGCCTGTAAT CCCAGCCACT CGGGAGTCTG
39151 AGGCAGGAGA ATGGCTTGAA CCTGGGAGGC GGAGGTTGCA GTGAGCCAAG
39201 ATTGCGCCAT TGCACTCCAG CCTGGGCGAC AGAGCAAGAC TCCGTCTGAA
39251 AATAAAGAAA AGAGAAAAGA AAACAACATG ACATTTCTAT AACTTAAAAA
39301 CAACAAATTA TATTTGTATG GGTTCTCTTA TACATATTGA TGTTCTCTGC
39351 CCAGTGAGAA CACAGGGTGT GTGGTAGATT GATGTCAAAA ATATGGTTGG
39401 ATCAGTCTTA TCAGGCAGAA TTGGAAGTTT CTGTGTCAGA CCATGGGAAA
39451 TACCATAGGC CATTGAGCAG GGAAGCTATG GTGAGAGTGC TGATAGAAAT
39501 GATTTGGCAA GCCGGGTGCG GTGGCTTCAC TCCTGTAATC CCAGCATTTT
39551 GGGATGCTGA GGCAAGAAGA TTGCTTGAGT CCAGGAGTTT GAGACCAGCC
39601 TGGGCAAAAC CTTGTCTGTG AAAAAAAAAA AAAAAAATTA ACTGGGCATA
39651 GTGGTGTGCA TCTGTAGTCA CAGCTACTTG GGAGGCTGAG GTAAGAGAAT
39701 TGCCTAAGCC CAGGGAGTTT GAGCCTGAGG TGAGCAAGA TCAAGCCACT
39751 GCACTCTCCA GCCTGGGTGA CAGTGAAACC CTGCCTCAAA AAAAAAAAA
39801 AGATACCTGC TGTGCCCCTA GAAGTTGGGA AGGCAAAACT TAATCTACCT
39851 TTTAAGGTGT TTACAGTGGG AGAGACACAA GGCAGCTACT GTTTCTATGG
39901 AGTCTGCTAA GGTCTCAGGG AGGTGTGCAC CTGGCAGGTG CTGGGGGAGC
39951 AGACAGATAA ACATCCAAAC CAGGACAGGA ATCTTCTGGA AGGAGATGGC
40001 CAGGAATTGA GCTTGAGGGA GTAGCTGGAT TTTGCTGGGT TAAGGAGGAG
40051 ACAGGAGGGG AGGGATATTC CAGGCAGAGG GAAGAGCGCA TGTGAAGATA
40101 CACGAGGTTG AAACAGCATG ATGATTCTGG GAACTTCAGT ATCTTCTTTA
40151 TGGCTGAAGG GAAGAGCAAT TGCATAAAAT GAGACCTGAA ATAAAGCAGT
40201 GACTGTTGAG GTGGAGGGGA GAGGATGGAA AAGGCACCAT TACAGAACAG
40251 GTTTCTAGCC AAACTTTCTA GATACTACTG GTGTCAAAGA TGAAGGTCAT
40301 GTGCAGCCAT GTAAGATTAG CCCAAGGAGC CAGCTCAAAC CATGCACATC
40351 CAGGGCCCAG CTTGAATTC ATGTTCTGGA GGCCTTGGCT GGGAGGCAGA
40401 ATCTGTGAAT TTTAAAAACA CTTTCATGAA TCCAAAGCAC ATGAAGGTTT
40451 AAGAGTCTGG TAAAGGCAAA ATTTTGGGGT TATGTGTTAA GAAAGGGCTG
```

FIGURE 3-15

```
40501 GAACAAGAGT CGGCAAAGGA AACAGAGGAA GGACAGAGAG GTAGGGGGAA
40551 AAGAGAAATG TGCAGCAGCT GCAGCTCTTC CAGGAACCCT GAGGATGAGG
40601 GCTGGGCAGA CACATCATTA GGTAAAGGCT TTAAATGAGG ACGTGCGTGG
40651 GGAACCTAGC CCTGCAATGT GTTGTGTGTC TGACCCTGAT ATGTGCTCAG
40701 TAAATGAGTT TTATGCCACA TTCTTTTGAG AAAAGAGCTT CAATATCATG
40751 GTGGGAACCA GAGGCCAATG ATCACCCAAA ATTAAAAGGC CAACCGCGTA
40801 TTCGCAGCCG TTGTGATGGG AGGGGTTAAT ATTTTTATTG AAAGAGTTTC
40851 TGTGACAAAT AATCCCTCTT AAAACCCAGT AGAAGCTGGG CGTGGTGGCT
40901 CACGCCTGTA ATCCCAGCAC TTTGGGAGGC CGAGGCGGGT GGATCACGAG
40951 GTCAGGAGAT CGAGACCATC CTGGCTAACA CGGTGAAACC CCATCTCTAC
41001 TGAAAATACA AAAAATTAGC CGGGTGTGGT GGCAGGCGCC TGTAGTCCCA
41051 GCTACTTGGG AGGTTGAGGC AGGAGAATGG CGTGAACCCG GGAGGCGGAG
41101 CTTGCAGTGA GCTGAGATTG TGCCACTGCA CTCCATCCTG GGTGACAGAG
41151 CAAGACTCCG TCTCAAAAAA AAAAAAAAAA AAAAAAAAAA ACCCAGTAGA
41201 TAGGCTAGGT GTGGTGGCTC ACATCTGTAA TCCCAGCACT TTGGGATGCT
41251 GAGGTGGGCT GATCACTTGA GGCCAGGAGT TCGAGACCAG CCTGGCCAAC
41301 ATGGTGAAAC CCCCTCTCTA CTAAAAATAC AAAAAGTAGC CAGTAGTGGT
41351 GGTGCACGCC TGTAGTCCCA GCTACTCGGG AGGCTGAGAT AGGAGAATCA
41401 CTTGAACCTT GCGGGGGGCA GAGGTTGCCG TGAGCTGGGA TTACACCACT
41451 GCACTCCAGC CTGGGGACA GAGCAAGACT CTGTCTCAAA AAAAAAAAA
41501 AGGAAGATAG ATGATCAAAG AAAATAAACT GACAACCTGA AAACAAGGAA
41551 GTAGAACTGG ATAACAAATG TGGAAAAATT TCTAGCCTCA CTAGTATCAG
41601 AGAAATGCAA ATTGAAACAA GGTGCCATTT TTGGACTCTA GTTAGTGATG
41651 GTAGTGAAAA CCAGAATGGT CCTTTCTAAA ACAGCCTGTG TGTCAAAACC
41701 ATAAAAATGC TTCTACCTCT TTTTACCCTG TTAATTCTAC TTCTGAGAGT
41751 TTTTCCTAAA GAAATAATTC AAAATAGGAA AAAGCTAAAA GCAGAAAAAT
41801 GTTGAACATG ACATTATTTA TAGCTGTGGA AAGATTGGAG GCTGGGCACA
41851 GTGGCTTATG CTTGTAATCT CAGCACTTTG TGAGGCCAAG TTGGGAGGAT
41901 TGCTTGAACC CAAGAGCTTG AGACCAGCCT GGGAAACGTA GTGAGACCCC
41951 ATCTCTTAAA AAAAAAAAAA AAAATTAGCT GAGTGTGGTG GAACGTGCCT
42001 GTAGTCCCAG CTACTTGGGA GGCTGAGGTG GGAGGATTGC TTGAGCCCAG
42051 GAGGCTGAGG TTACAGCCAG GATCACACCA CTGCGCTCCA GCCTGGGTGA
42101 CAGAGTGAGG CTCTGTTTAA AAAAAAAAAA AAAAGAGAGA GAAGAAAAAA
42151 AAGATTGGAG ACAATTTGAA AAGCCAGTAA GGAGCCAGAC ACAGTGGTGC
42201 GTACCTATAG TCCCAGCTAC TCAGGAGGCT GTCGCAGGAC AGAATTGCTT
42251 GAGCCCAGGA ATTCGAGGCC AGCTGGGCAA CATAGTGAGA CCCCCAACTC
42301 TTAAAAATGT TTTTAAATTT AAAAATAAAA AGATTTTTTA AAAGCCAGTA
42351 AATGACTAAA TAATTATGGG AAATCTACTT AATAAACTAT TCAAAAGTTA
42401 TTAATTTTCA TGACCGTAGG GATATTTTAA GTGAAAAATA AAGTGCAGAA
42451 ATGTTTTATA TTAAGTGAAG GAAGTGGTAT ATAAAGGAGT ACAGACAAGC
42501 CAGGCACGGT GGCTCACGCC TGTAATCCCA GCACTTTGGG AGCCCGAGGC
42551 AGACAGATCA CGAGGTCAGG AGATCGAGAC CAGCCTGGCC AACATGGTGA
42601 AACCCCGTCT TTACTAAAAA TACAAAAATT AGCTGGGCGT GGTGGTGCGT
42651 GCCTGTAATC CCAGCCACTT GGAAGGCTGA GGCAGGAGAA TCGTTTGAAC
42701 TAGGGAGTCG GAGGTTGCGG TGAGCCAAGT GCGCCACTGC ACTCCAGCCT
42751 GGTGACAGAG CAAGATTCTG TCTCAAAAAA TAAAAAAAAA AAGGAGTACA
42801 TACACTATCA TTCTAAATTT GGTTTGAAGA AACGTGTTTG TAGATATTTA
42851 TTCAGTATAT AATATGTGGA TAAAAAGGG ACTGGAAGAA AGCCCACTAA
42901 GTGTCAACAG TAACTTCACC AGGTGATGGG AATTTGAGAA ACTTTTTTGC
42951 TTACACATTT TTCTGTATTC CTATATTTTT CATCTAGATT GTGCACTACT
43001 GTTATCAGAA TTTTTTTTAA ATACTATTTT TTTTTTAAAG TAAAGCATAA
43051 TACCAGGTGT GGCAACTCAT GCCTGGTAAT CCCAGCTACT GGGAGGCTGA
43101 GGTGGGAGGA TTGCTTGAGC CCAGGAGGTT CAGCCTGGGC AACATAAGCA
43151 AGACTCCATC TCAATTAAAA AAAAAGAAA AGAGGTAAGA CATGTGCTTG
```

FIGURE 3-16

```
43201 TATTATTATA TCTTATAATG ATATCTTTTT TTTTGTTTTT TGAGACAGGG
43251 TCTCACTCTG TCCCCCTGGC TGGAGTGTAG TGGTGTGATC TTGGCTCACT
43301 GCAACCTCCG CCTCCCGGGC TCAAGTGATT CTTCCACCTC AGCCTCCTGA
43351 GTAGCTGGGA ATACGGGCAT GTGCCACCAC GCCCGGCTGA TTTTTGTATT
43401 TTTAGTAGAG ACGGGGTTGC CCAGGCTAGT CTTGAACTCC TGAGCTCAGG
43451 TGATCTGCCC GCCTCAACCT CCTGAAGTGC GGGGGTTACA GGCATGAGCC
43501 ACCACGCCTG GCCTATAATG ATATCTTAAA AGATTGCTTT CTTTTTTTTT
43551 TTTTTTTTTT TTTTTTAGAC GGAGTCTCAC TCTCACCCAG GCTGGAGTGC
43601 AATGGCATGG TCTTGGCTCA CTGCAACCTC CGCCTCCCGG GTTCAAACAA
43651 TTCTCCAACC TCAGCCTCCC AAGTAGCTGG GACTACAGGC GCGTGCCACC
43701 ACACCCAGCT AATTTTTATA TTTTTAGTAG AGACGGGGTT TTGCTATGTT
43751 GGCCAGGCTG GTCTCGATCT CCTGACCTTG TGATCCACCC GCCTCAGCCT
43801 CCCAAAGTGC TGGGATTACA GGCATGAACC ACCGTGCCCG GCCAATTGCA
43851 TTTTTTAAAA AGACTGGAAG ATTGCTAGGA GTATTAGTGG TTTTCCCATG
43901 CCCCTTCTCT GTTTTCCAAA TTGCTTGTAT TGTGGCTGCA GTCCTTTTAT
43951 AATATGAAAC AGGTAAATAA CAACTTATGT TGTGGCTGCA TCAAAGGGGT
44001 GAGAAACGAA AAGGAGAGGA CAAAGCAAGA TGTGCAGAGT TCGACCTTTC
44051 CAGGCTCTCT CAAAGTCAAG GTTTTGATCA ATGTTATGAG GGAGGCCTGT
44101 GAAGTAGCTC AGATGGTCTT GAGCTTTCAG CATCATGGAT TCTTCTTTTA
44151 GATCCCATCT TCCCTTCCCA ACTCCCCCTT CCTCAATTCC TACTGCTTAA
44201 GTGTCCATAG GGCGATTTCT TTTTCACTGT TCAGAAGCTT TCTGCAAGAT
44251 GTTCAAAATA CTAGCATTGG TTTGAGCAGC TAGTCTGTCT TGTGTTCTTG
44301 ATTTGGGGGA CTTAGCTTCT ATTTAGATTT CTTTGAAGCT GGATGCCAGT
44351 GACCCAGGGT CTATGGAAGA GTAAGAGCCA CTTGTGAGGA TGACTGAAGA
44401 GGCCACAAAC TCTCAGATCC TGAGAGTGTA GGACAACTTG TGCCTTCTGC
44451 TAGTCCCAGG CCAGAATGGC CATCCTATCT TTAAAAAAGA AAGCAAGCAA
44501 GAAAAACGAA AGGTTATAGT TATTTCCCTA AGTACTATTT GAATTATTTT
44551 GTTAAATTAA GTATGAGAAA GAGGTTTGAA CGCTTTTCCA GCTTAAAATT
44601 TAAAATAAAT ATACAGTTTT TAAGTAAAAG TGAGATATGA TTCTTTAGAA
44651 ATCATCTGGC ATTTAGCCAG GCATGGTGGT GTGCACCTGT AGTCCTAGCT
44701 ACTCAGGTGG CTGAGGCAGG AAGATCCCTT GAGCCCAGGA GGTTGAGGCT
44751 GCAGTGAGCC ATGATCATGC CAGTACTTCA GCCCGGGCAA TAGAGCAAGA
44801 CCTTATCTCT AAAAAAATAA TAAAAAGACC TCACATTTAG ACAATGTGGT
44851 AGTGTGCTGG TTCAGAAGGA GCCCAGCTAT GCATGGCTAA GGGCAAATCC
44901 CTGAATGGAG AAGGAAATTG AAAAATGTTG ACTAACCTGA GAAACAGTCT
44951 TTGAAAAGG GTGATCTCAG GTTCTCATGC AGGACAATTT AGGAAAAAGA
45001 GAGCAAGCCA GGAGAAGGCT GAGAACTTAT TCCCCATTAG TCAAAAATCT
45051 GCTTTAAGTC AAGATCCTGC AATGGCCTTT CACAACAAGC CCCTGAAAAT
45101 CAGCAGAACA AAGACTGGGC CTGGTGAGTG AGTGCCTACG CAGAGTTCTT
45151 GCTGCCGTGA TTCAGTGCAA GTTAGAAACC TGTGCTCTTC TTTAGCCTGG
45201 GGAAAAACCA AAGTCAGCAA ACCCAGCTCA ACTCAGCAAA CTTTCGTCGC
45251 CTGTATGCTA ACTATAAGGC ATGTTGCTAG GTACTGTGGA AATTGTAAAG
45301 ACACATAAGA TAGGAACCTT CCTGAAAGCA GTAACACTTT AGTTGGGTAA
45351 AGGGATAAGG AGATATACAC ACACACACAC ACACACACAC ACACACACAC
45401 CCCACTACTT ATATATATGA ATATAAGGGA ACTCCTTCTT TTTGAGGGAT
45451 GATTTTCGAA GTAAAATATC ATATTTGAGC ATATTTAAAA GGCCACTGTA
45501 AGGCTGTGTG CGGTGGCTCA CGCTTGTAAT CCCAGCACTT TGGGAGGCCG
45551 AGGTAGGTGG ATCACCTGAG GTCAGGAATT CGAGACCAGC CTGGCCAACA
45601 TGGCGAAACC AGTCTCTCTA CTAAAAATAC AAAAAAAAAT CAGTGGGGCG
45651 TGGTGGCGGG CGCCTGTAAT CCCAGCCACT CAGGAGGCTA AGGCAGGAGA
45701 ATTGCTTGAA CCAGGGAGGC GGAGGTTGCA GTGAGCCGAG ATGGTGCCAC
45751 TGCACTCCAG CCTGGGCAAC AGAGTGAGAC TCCCTAAAAA TAAATAAATA
45801 AATAAATAAA TAAATAAATA AATAAATAAA TAAAAGGCCA ATGTAAAAGA
45851 GGCCTAACTA TATTTAGGTT TTTCTTTTCC TTTAAATCTA ATTCTAAATT
```

FIGURE 3-17

```
45901 ATGGACCATT GTCAATATTT GTAGCCTCTT TCGTTGATTA TAATAATAAT
45951 CCCTGAAAAT GCCTTCTAAA GAATGCTGGC CGCTTGAGGG CAGGAGCAGT
46001 TTATCAGCTG TGTTTACCTG AAACAGCCCT CAGTGTTTGC TGGGCATTGT
46051 TAAATGAATG TGCAAAAGTT GAACGACAGA CGGACATATT ACAGGGGGAC
46101 CTTACCCCCA GTGAGCTAAT GATGACATTG ATAATTACCC TTCATTTTTT
46151 AGACACAGTC TTCTGGGATA TATTTTCAGT GTTCCACGTG GTCTTCATCT
46201 TGATGCGTCT GTTTCACATG TGAACGTAAA GTTCGTGAGC ATCTAGTTGA
46251 GGCTGAGGAA TCACTGCTTT CAACATTCCC TGTGGCTTAC ATCCCTGCAT
46301 TTTTATGATC ACTGTAGTTT TAATCACTGG CACTCCTGTG TTTCTATTTT
46351 CCACGAATTG CAAAATGCAA TAAAAAATTC AAATATTGTA AACAAGCATG
46401 GCTATACTGA CAAAGGAAGG CCAACATTTA ACTGCTAGGT GATTTTCAAA
46451 AGCTCAGCAT CTTTATGTAA AAAGCATAGT AGGGATGCAG CGAAGTCAGA
46501 AGTCAAATTT TATTAGAGCT GAGGAGAGCC TGTAGTAGCT TTTGCTTTTT
46551 CCCTGGTGGC TGCTCACTTG AATTTCAGAC AGTTCTAGTA ATGAGAGAAA
46601 ATAAATAACA TTACAGGGTG AGCTAACCCT ATGAACCCAG ACCTGTAAAT
46651 TTGTAGCAAA ATGATACTTA ACCTCACAGA CTTGTGTCTT AATCTCCTTA
46701 AGAGGCTTTT TTTGAGCAAG GCTGAGACAT CTCAGAAGAT ACTAAATCTG
46751 TGTCTATGAA CCTGACCACA AAAGAGTTCT TCCCTCCCAG GGTCTGGAGG
46801 GTGTGAGTGC CTGTCGGTCC GTGTGCTGTT TAACCCTCTG GTGCTGGACT
46851 CCGGGTCTCC CTCCGCTCTT TTCTCCCTGA TGCAGAGCCC ACACTGGTGC
46901 GCTAACCTGC AGCGTCTCTG TGCTTCTCTT CTTACCTCCT CTTTCCCCTT
46951 CTCTTTCCCT CTTGCTGTGG TGTGTCCAGA AAAGGAAGTC GAGTTCCAGC
47001 GTGCACCTAA TGGTGAGCCT TGCCTGCCCA CCCATCGCCC ACTCCATGCT
47051 GCCTGTGCCC GCCTGCCAGC CACGCAAACC TGTTCTGCCA CGTGCGTGTG
47101 CCTCACTCAT CCTCACTGCA TGTCTGTGCT GTGTGGGCAG GTGTGGCCTG
47151 TCCTGCCAGG CGGGGGCCAT TGCCCAAGGT CACCCAGTAG CCTAAAAAGT
47201 GGACATTGGA AGGGGTGGTA CGGCACCCCC TGCTGTGGAG CTTGGACAGA
47251 CCCCAGCGAC CCAGGGTAGG ATGTGAAGCT GGTAGGGACT TGGGGCAAGC
47301 AAGGGAGAGA CCCTCACTCT CTTGTCACCC AGAAGGAGAG GCCCTGCTTC
47351 CCAGGCATGA GGAGCTGCTT CCTACAGACT GGCAGCTGGA GGGCAACTGT
47401 GTGGTGGGCA GAGGAGCTGG TTGCAGGCTC CCACTTGTGA GTCTCGCTCT
47451 CCTGGCTCTG CCCCCGTGCA AATCCCATTC TCTCTAGCTG TGCCCAGTGG
47501 TTTATTCTGC CCACCCAGCC CTCGGGGGAC AGCTAACTCA TCTTTCTCAC
47551 GGGACACTGG GCACCAAGGG CAACACAGCA GCCTGAGTCA TTATGAAACC
47601 ATCCATTAAA ACCAGAGGTG GGGGCCGGGC GCGATGGCTC ACGCCTGTAA
47651 TCCTAGCACT TTGGGAGGCC GAGGCGGGTG GATCACAAGG TCAGGAGATC
47701 AAGACCATAA CACGGTGAAA CCCTGTCTCT ACTAAAAATG CAAAAAATTA
47751 GCCAGGTGTG GTGGTGGGCG CCTGTAGTCC CAGCTACTCA GGAGGCTGAG
47801 GCAGGAGAAT GGCGTGAACC CAGGAGGCGG AGCTTGCAGT GAGCCGAGAT
47851 CGCGCCACTG CGCTCCAGCC TGGGCGACAG AGCTAGACTC CGTCTCAAAA
47901 AATAAATAAA CCAGAGGTGG GGCCACTTGG GTGACATCCC AGCCCTCTGC
47951 AGGTTTTGTG GGCACCCTGG AGTCCTTGCC CCCTGTGAGG GTCTTGGCCT
48001 CAGCTGGGAT TTACAGGTAG GGCAGCCCTC TCTAACCAAC CCCGAACAGG
48051 TCAGCATCAT TCACTGAGCT AGGTGGGCTT TGCTTCTTGG TGGGAATGAG
48101 AGACAGCAGA GCTCCCGTGA GTTAGACCCC ACCGTCTCAC TACTCCTGGG
48151 CCCCCTCTTC TCTAGCCTGT CGCAGTCTGT GGAGTCTTGT TCAGTGGAGT
48201 CACTTGGTGC CTGGCTTGAG GTTCCATGCC TAGCCCTGGG TTTGGGGATG
48251 TCTGAGCCAT TGACAGCAAG CTGGCGGTGG ACGGCTTCAG GTCTGGTCCA
48301 AGAGGCCTCC AGGCAAGAAG TAGGACAGTC AGGATGCTTT CTGTGTATGT
48351 CCTAGGAGAG AAGACACACA TTCTAGCTGT CGATGTATCA TCTGTGCCCT
48401 GTGCAGGGAT GGTAGCCACA CATTTGTCTC ACTGCCTATT GAAGAACTTG
48451 CAGGCATCAG GCTGCTCCTC AGTGGCCCCC AACCCACTG GAACTCAGTG
48501 AGATGGAGTA CGCTGGTTAG GGAACTATCA GAGGCAAAGA ACATCACATG
48551 GATATGGCTC CCTGCCCTGG AGATCAGCCT TCTTCCTTTC TTCCATCTTC
```

FIGURE 3-18

```
48601 CCCTTGCCCC TCCCTTGCTG TGCCCCTCCG TGTAATGTTT TTGTTTGTTC
48651 GTTTGCTTTT GGTTTTTTGA GATGGAGTCT TGCTCTGTTG CCCAGGCTGG
48701 AGTGCAGTGG TGCAATCTTG GCTCACTGCA ATCTCTGCCT CCCAGGTTCA
48751 AGCAATTCTC TTGTCTCAGC CTCCCGAGTA GCTGGGATTA CAGGCATGTG
48801 CCACCATGCC CGGCTAATTT TTGTATTTTT AGTAGAGACG GGGTTTCACC
48851 ATGTTGGCCA GGCTGGTCTT GAACTCCTGA CCTCAGGTGA TCCACCCGCC
48901 TTGGCCTCCC AAAGTGCTGA GATTACAGGT GTGAGCCACC GTGCCCACCC
48951 ACCCACCATG TAGTTTTGAA AGGCAAGGAG ATATCCCTGG TGGTCATGGT
49001 GCTGTTGGGA ATGTTGGCCT GTGTGTGGCC TACTCTGTCC TGGGGGCTGG
49051 ATTCTGGGAC TACAGCTACA GCCCCGCTGG GTTTCACCTG CCCCTCCCCG
49101 GAACACTGCC CTTCTAGCTG ATCAGGCCTA AGATTTGTCA GACAAAAAGG
49151 TGAACAGCAC AGTCCTGACT CTGCTCCCTG AGGTCAGTGA ATGCATTTTG
49201 TGTCTGAAAG GGACTTCCAC CCCCATCCTC TGGACACCAT CTCTTAGGCC
49251 AGGCATACTT TTCTTTTCTC CTTCCTCTTT GTTTCAGGCT TCGAGCTGGT
49301 GTTGTAAGAA GGAAATACAG GTGCTGGGTT GAAAGTGCAG CAGGAGACTG
49351 CCCACAGATA GGGGACCAGA GTTTCTGAAT TTTGTTCTGC TTTCTTATAA
49401 ACTACCCCCC TTTTTCCTGT ACAGTGGGAA GAAGATCTTG AACTTCTTTG
49451 GGTCAGGTGT GGATTTTGCA ATGACCTGGC ACCTGGCATA AGCAGAGATT
49501 TCTGGAGGGA TGCTTTAAAA CAAGGCTTTG GGCTGGTCCC ACCTTGAGGG
49551 TGCCCCCAGA GCTAGGTCTC TGGGCCCCAC AAATACTTCC TCTGATCATC
49601 TCTCTAGCCA TCGCTCCCAT CTACACAGCG TTATGGAGGC CACCTCAGGC
49651 CTACCTCCTC CAGGCCAGAC CAGGGGGCAA GGGAGGTCTG GGAGTTGAAC
49701 CTGAGTGGCC TTGGGGACTC TGGAGGAACT AAACCATCTG TTTTCTTGTC
49751 TCAGCCACAG AGCAACAACA AAAACAGTCT CGTAAGCCCA GCCCAAGAGC
49801 CCGCGCCCTT GCAGACGGCC ATGGTACCTC CTGACTACAG CTTCTCCGCC
49851 TCTGACCCTG GCTGCCTCCT GCCCCTTCCC TCTTCCTCCT CTTGTGCCCC
49901 CTCCCTGGCC TCCTGGCCTG TTCCTTTCTT GGTCCCCATA GAACTGACTG
49951 CTTTGTGTGC CGCCCTGTAT GCCCCTTCCC CTTCATTGTC CCGCCTGGCC
50001 GCGCTCCATC CCGCATGGCA GAAGTGCTGC TCCTGCTCCT GCTCCTTTCG
50051 CTGGTGGGGG GAAGAGTGAT CAGGGCTCTC AGCTGAACCT CCCAGGCCCA
50101 GCCCAGGACC CCTAGTGGGT CTGCTGTGGG GGCTGGGAAG GTGAGTTGCT
50151 TAGGAAAGGA GAGGGTAGGA GCTTTCTTGG GACCTGAACA TCAGTTCTTG
50201 GAGGCCCCCT TGTAAAACCT GCCTCAGCCT CTCCTTTGCA AAGCCAGAAA
50251 CAGGAAAGAG GGCTGGGGTC CCCACCTCTG GATGGTGCTG AGGTCTCCAG
50301 GCTCCTGGAG TGCCTCATGC TGGCTAAGTT CTCTCTGGGC TCCTCCAGGG
50351 GTTCTGTGTG CTCTTGGAGG TCCCTCTGCT AGTGGTGGCT AACTAGAGAG
50401 TCAGCAGGGG GGTGACTGGG AAAGAGGGAG AGGTGATGTT GCCTGCTACT
50451 CCCCTCCTTG CGGACCCTCA TACCACGTGA CGTGGCGGCG TGGGGCCAGG
50501 AACTAGGGAA GGCAGAAGGC GGGCGCAGTG GGCAGCTCTC TGGGCTCAGC
50551 TTGCTGAGGG GGCCTCCTGT CCTGGCTCTT TCTGGGAGAC CTCATTCTTC
50601 TGCCCATGTT CCTGCCTCAC ACATTCCCCG TGATGAACGC TGTGGGCGGG
50651 GCCCGGCCTG TGCCCTCAGT CCCACAGCTC CTCTAGTGTA CCTGCCCCGT
50701 GGGAACCCCA TGTGGAAAGA GCCCTCAGAA CTGACAGGAA TCAGGGACAG
50751 AGGCCCTTGC TGTCAGCCTC CTGGGCACCT GCACCTGCCA GGCCTCTCTT
50801 TCTTACCAGC CCAGTGCTGC TGCCAAAATC CAGGGCTATC CCAGCTGCCC
50851 GGGACCCCAG TTGAGCCGGG ATATTTTGTC TTCTGGAGAT GGCTGGTGGG
50901 CAGGCCTCAG TGGTCATCAT AGGGTCTGCG GGGGTCCTGG GGTGCAGGTG
50951 GGGCTCCTCA GGGAAGAGCC ATAGTCTGTC CCCAAGTCGG AAGGGTAATC
51001 TTCATCTTCT CTCACAGGAG CCACAAACCA CTGTGGTACA CAACGCTACA
51051 GATGGGATCA AGGTGAGTGG CTCCTGAGCC TGCCTCCTGC TTTCCAGGTC
51101 AGCAGGAGAC AGGTGGGCTG GGTCCCAGGG GTCTACAGGC TGCACCCTGA
51151 GGCCAAGGTG TTTGCAGAGG CTCAGCTGAA GGTAGCCTGT GCCCACAGTT
51201 GCTCCATGCT GAGGAAGGGC ATTATACCTT ACAGAGCTCA GGCTTTGCAG
51251 TCAGACAGAC CTGGTCTGAA TCCTGGCCCT GCACCTTAGT ATCCTTTATC
```

FIGURE 3-19

```
51301 TGCAAATTGG GGATGATAAT AATAGAATCT TCCTCCATAT GTCGGAAGTT
51351 TAAATGAGAG TAAACGTTCA CTGAAAAAAT AGGCAAGAGT ATCTCCAGAC
51401 CCTGGAGCGT TCTCCATGGC CTGACCCCTT TGTGCCCTTG ATGTTTTCAC
51451 CAGCATTCCT GAACATCTGT TAAGCCCAGA TACCATCCAT GGCTCTGGCT
51501 TACAGAGGTG ACAAGACAAA TTATCTGTTC AAACGGTGGG TGGGATGGGA
51551 GGCAGATAAA AAACCAATAA GCAAACAGAT AAGATAAGCT GGGCACCGTG
51601 GCTCACACCT GTAATCCTCA CACTTTGGGA GGCCAAGGTG CGCAGATCGC
51651 CTGAGCTCAG GAGTTAGAGA CCACCTTGGG CAACATGGTG AAACCCTGTC
51701 TCTACTAAAA TACAAAAAAG TAGGCAGGTG TGGTGGCGCG TGCCTGTAGT
51751 CCCAGCTACT TGGGAGGCTG AGGCACGATA ATTGCTTGAG CCTGGGAGGT
51801 GGAGGTTGCA GTGAGCTGAG ATCACGCCAC TGCACTCCAG CTTGGGCTAC
51851 GCAGTGAGAC TTAATCTCTC AAAAAAAATA AATAAGATAA AATCTAATGT
51901 CAATAGGTAA TCTGAAGAAA ATGGCAGAAA GTAGAGAGAG GGCCAGGTGC
51951 GGTGGCTCAT GCCTGTAATC CTAGCACTTT GGGAGGCCAA GGCGGGCGGA
52001 TCACTTGAGG TCAGGAGTTC AAAACCAGCC TGGCCAACAT GGCAAAACCC
52051 CATCTCTACT AAAGATACAG AAATTACCTG GGGATGGTGG CACATGCCTG
52101 TAATCCCAGC TACCTGGGAG GCTGAGGCAG GAGAATCGCT TGAACCTGGG
52151 AGGCGGAGGT TGCAGTGAGC TGAAATCGTG CCACTGCACT TCAGCCTGGG
52201 CGACAGAGCA AGACTCCATC TAAAAAATGA AAAACAGAAA AACCTCACCA
52251 AACTAGACAG AGAGAACAGG GCCTTGAATT AAGTAGTCAG GAGAGGGCTT
52301 CTTTCAGGAG GTGATATCTG AGCTAGAAAC TGAATGGTGG GTGGGAAGGA
52351 GGCAGCCAGG CCAGCTCTGA GGCTGAGTGC CCTAAGCAGA AGGAACTGAA
52401 GCTCAGATGT GGCCTTTGTA ATCAAGCAGA GGGAAGAGCA AAGTGAGACG
52451 GGGAGAACCA TAGGAGAGTG ATGAGGTTGG AGAAGCAGCA GGGCCTGCTA
52501 CAGAGGCCCT TGTAGGAGTT TGCATTTTCT TCCAGCAGCA AGGAGAAGCT
52551 ATTGGGAGTT CTTAGCAGGA GTAACAGAAT CTAGTTGACA CTTTAAAACA
52601 CCACTCTGGC CTCATGATCA AGAACTCTAG GGAGGCCCGG GCGTGGTGGC
52651 TCACGCCCGT AATCCCTGCA CTTTGGAAGG CCGAGGCGAG TGGATCAGCA
52701 AAGGTCAGGA GCTCGAGACC AGCCTGGCCA ACATGATGAA ACCCCATCTC
52751 TAATAAAAAT ACAAAAATTA GCCAGGCATG GTGGCAGGCA CCTGTAATCC
52801 CAGCTACTCA GGAGGCTGAG ACAGGAGAAT CACTTGAACC CGGGAGGCAG
52851 AGGTTGCAGT GAGCCGAGAT CATGCCATTG CACTCCAGCC TGTGCAACAA
52901 GAGCAAAACT CTGTTTCAAA AAAGAAAAAC TCTAGGGAGG AGGTAAGTGT
52951 GGAAGTTAGG GAGACCATGA AGCTGTTATC ATGGTTCAGG TGTGAGATGC
53001 TGGTGGCCTG GAGTCAGGTT GTAGCTGTGC ATTGGAAGTG AAGAGGTAAG
53051 ACATGGGGTT TACTTTGGAG GCAGAACCAG AAGATTTTAT TTTAGATTGG
53101 GCGATCTGAA TATAAGGGAA AAAGAGAAAG AGAAGGATTG AGGATGACTC
53151 CAGGTTTTAG CCTGAGTAAC TGGGTAGATG GTGGCATTTA CCAACTGGGG
53201 GAAGACTAGG GAGGGGATTT GGGAAGAGTC AGACAGCCAG GGTGGAAGCA
53251 GAACCTTCCA CAATTCCTCC TTGCACCTCT TGTAGGAGCA GAAACTCTGC
53301 TTTTGTTCTG CTTTGCTCCT CTGGCTTCCA AGGGATGGAG CATATAGAAA
53351 CATGTTCTTT TTGGCCTACA GGGCTCCACA GAGAGCTGCA ACACCACCAC
53401 AGAAGATGAG GACCTCAAAG GTAGGTGCTG GCCCTTGGAG GGGGAAGGAC
53451 TCCAGCAGTG ACCCAGGTAC CTGGGCTCCA ATGGGCACC TGCCTTTTCT
53501 GTCCCCAGAA CTGGGAATGC TGGCTCCTAT GCCCCTAGGA GAGGGCTTGG
53551 TATAAAAGCT ACTTTCCACG AGCCAAGATA TGAGGCCCCT GTCTGGTGTT
53601 GCTGAGTTGG GCAAGAGGCT TCTCTTCTTT GACCCCAAGT CTAAAATAGC
53651 TAAGCTAGAG ATTCTCCAGG GGCCAGGGCT CAGAGAACTG TTCCTGTTGC
53701 TGATAATGAT GTGCCATCCA AGAACAGGGG TACCCAAGT CCCTGCCGAA
53751 GTAGCCTGTA AGTGCTATGA GTCATAAATA GAGTGACCAA TCACTCCTGG
53801 TTTTCCTCGG ACACAGAACT TTTGGTTTTA AGACTGTGAT GGGCCAGGAG
53851 TGCTGGCTCA CACCTGTAAT ACCCAGAACT TTGGGAGGGC CAGGGCAGAA
53901 GGATTGCTTG AGACCAGGAG TTTGAGACAA GCTTGGGCAA CATAGCAAGA
53951 CCTTGTCTCT ATTAAAAAAA AAAAATTAGG AACAAATAAA TAGGCCAGGT
```

FIGURE 3-20

```
54001 GCGGTGACTC ACACCTGTAA TCCCCACACT TTGGGAGGCC GAGGCAAGTG
54051 GATCACTTGA GGTCAGGAGT TCAAACCAG CCTGGCCAAC ATGATGAAAC
54101 CCCGTCTCTA CTAAAAATAC AAAAAAAGGC CGGGCGTAGT GGCTCACGCC
54151 TGTAATCCCA ACACTTTGGG AGGCCAAGGT GGGTGGATCA CCTGAAGGTC
54201 AGAAGTTCAA GACCAGCCTG GCCAACATGG TGAAACTCCA TCTCTACTAA
54251 AAATATAAAA AATTAGCCAG GTGTGGGGCA GGTGCCTGTA ATCGTAGCTA
54301 CTCGGGAGGC GGAGGTGGGA GAATCGCTTG AACCTGGGAG GTGGAGGTTG
54351 CAGTGAGCCG AGATCACCCC ATTGCACTCC AGCCTGGGCA ACAAGAGCGA
54401 AACTTCTTCT CAAAAAAAAA AAAAAAAAA AAAAAATTAG CCGGGTGTGG
54451 TGGCGGGGTC CTGTAATCCC AGCTACTCGG GAGACTGAGG CATGAAAATG
54501 GCTTGAACCC GGGAGGTGGA GGTTGCAGTG AGCTGAGATT GCACCACTGC
54551 ACTCCAGCCT GGGTGACAGA GCGAGACTCT GTCTCAAGAA AAAAAAAAA
54601 AAAAATATAT ATATATATAT ATATATATAT ATATATATAA ATATAAAACC
54651 CAGATAGTCC TGGGAACACT GGGATGAGTT GGTCACTCTA GTCTTAAGAT
54701 TTTGGCCTGA ATGATGGAGT TGGAACTAAT CTGACAACCG TGAGGCCACA
54751 TTTGGTCATG TCCTGGTGGG CCCGTAAGGA CCACTAGCCT AAGCTTGGGC
54801 CTGGCTAGAG TGCCAGGGCG GTGGGAGGGC ATGGCAGGCT GGACCCCCGG
54851 GAATCTCTGT CCTGCTCTTT GATTGGGCCT CCTGGAATTG CTCCCTTTGC
54901 CTGAATTCAG TAAGTGACCT TGGGCCAGGA CATCAGAAAA GACAGAGGAA
54951 CACTCTAGGA CAGAGCTGGG AGAGCATGCC CTGGGTGGCA AGGGGGCACC
55001 AAACCTTTTG GAACCAAAAA AAATAGCAGA AAGCTGCGAG GAAGTGAATC
55051 ATAGTAGCTC CAGGCCCCTG TGAGTGAGGT CAGATCAGTT TTGATTCCGG
55101 CACTGCTGGC AACATAGGAG GCGCTGTCAC TGCTGGGCTC TGGACCCTGT
55151 GGCCTGGCCC CCTGGAACAT CTTCCCCGGG ATCAGGGGTC CTTGGACAGG
55201 CTGTTGTAAG GCTCGTCTGG AAGCCACAGC CCAGGTCTGG GCACCTGCCT
55251 GGTGCCCTCA GCTGGGAGGC CTCTCTGGCA GAGGCGGCGG CGTGGGATGT
55301 CGTCCAGTGT CCACAGCAGC CTGAGGCGAG GCGTCCCTT GCCCCGGCTC
55351 TACAGCGCCA TGGGCTCGGG GCCTGTCTGG CTTGCTCGCT CACCTGCCTT
55401 GTTCTGTTTG TTTTGGCTGC TCTGCCTTGC CCTGCCCTGC CCTGCCCTGG
55451 CTGGCTAGCT GCCCCGCTCC GCACTGGGAA TGGCAGCTCG GTGCCTGAAG
55501 GACGGAGCTC CCGGGACAGA ACAGCCCCCT CTGCAGGCAT GCAGCCCCAG
55551 CCTTCTCTCT GCTCCTCAGC CAGTAAGTGT GAGGGAGGCA CATTCTGGCT
55601 TCCGTCTCCC TGGCTCGTCC TGAAGCCCCT CAGGGACCCC CACCACAGCT
55651 GTCAGTCCCA CCCACCTGCC CGTGGTAGTA AGCTCTGGGA GCATGGCCTC
55701 TGCTGGGGGT GGGGGGTAGA CTGGAGGTGC TGTTGAGACC AGGCAGGGGC
55751 CCCTGAGTCT GGGGCCCAAA GAAATATGAG AAGTGTGGGT GGAAAAACAT
55801 GGCCTGGGAT GAGGGGAGTA GAAAGCCCCC AGGATGTGCA GTGGGCCTTG
55851 CCTCAGCGCT GAGCCAGGAA GAAGGGCAGA GTCGGAAGTC AGGTCTGTGG
55901 GGGTGGGAGT GGGATGATGG GGAAATCGTG ACAGCGAGGA ACTGTGTTGG
55951 GGATGTAGTG CTTCCTGAGT CTCAGCATAA CAGTATTAAG AGCATGGGGT
56001 CAGAGGCAAG ATAGATCTGA GTTTAAATCC CAGCTACACT GCCTTCAAGA
56051 GTGTGAAGTT TAACCTCCCA GAGCTGCAGG TTCCTTATCT GTAATGTGGA
56101 AATAAAATGG CACGCACCTC AGAGCCTTGT TAGATAAAAG ACAAGGCAGT
56151 AGGAAGTCTT GATACGGTGC CTCGATGGGT TATCAGTAGC TCATCCTCAT
56201 ATTTCTAGTT ACGTCTGTGC TGGAGGATGC CTTTGTCTGC TGCTTTTCCT
56251 CCCACCATCT ATCCTTGCAG AGTTTCTAAG CACAACCCTC TTCGCCCGTG
56301 GGGCCCCAGT CAGGTCATCC AGATGGGTCT GGTGGGGTTG GAGAGGGTGT
56351 GTGTGTTGTG GGTGCACACC TGCCTGCTGC TTTTGGAAGC CGATCGAACT
56401 CCTTGCTTCC CTTAACCTGC TGCTTGCTCA CCTGGAGCTG TGGCCTAGCG
56451 GGGCTGACGG CTGTGGGGCC CCCTCCTGGA TGTGCCTTTG GCTGCGCTGC
56501 CCTGTCCCAA CTGTGCTGCT TGGCTGTGCT GGCCCGGCTG GGCCGTGGTG
56551 GTGCTGTTCT AACGCTTGCA GTTGTCTTGC AGCCTTTTGC TCCTGTGAGG
56601 AAAGGGTTGT GGCCTGGCCC CGCCCAGGGC TCGGGTTAGG ATGAGCCCAA
56651 GCTCAACCCA AGCTCTCCCT TACCCTGGTG GCAGCCCCTG CTGGTAGTGG
```

FIGURE 3-21

```
56701 CATTCCCTAT AAGAGAAGCC CATGCCGGCA GGACATCACC AGCTGTCCCT
56751 TGGCTTTGGA TGGGTTGGGG AGGAGGCCTC TGGAGGGCAC CACCTCTGCC
56801 TGCCTGTCAG TCTGAGCCCT GTCTGGTTTT CCTGAGGAAC ACGTCCTGGC
56851 AATGAGAGCT GGTGTGAAAT GTGCAGCTTT CCCAAGCCTC GAGAGGTAAA
56901 TGGAGCAGCC TCTCTGGTAC AGGCTGTCCC AAGTTTTTAC AGTTCTGGGA
56951 TCATTTCTCC CAGAAAAGCC CTGTGGAGTT GAGCAGTGGG AAGCATCCAT
57001 CCTAGGGTTC TGATGGTCTT TTGGCACCCC AGCCCTAGCT GGATTCTGCT
57051 GTCAGGCTAC CTGTCACCCA GGGCTGGGTC CTGGCCACTG AATGAGGGCT
57101 ACGAGTGGGG GTGGTGATTG AGACCTGACT GAGCCCCTTC AGGTGAGAGA
57151 AGTAAATTGG GGGTGGAAGC GGCCTTATTG GGAGATGCTT GTGAGAGAGG
57201 CTGCTCATAC AGGGGAGGGG CTCACAGCAT TCACGATGTA CCAGGCTCCT
57251 CACCTGTTAA AGGCAAGCGT GTTTTCTGCA ACCTGGTTGT TGATGGAAAG
57301 GGAGGCAAAG GCCAAAGAAC CATAACTAAT GGCTGGGCTT CAGGAGAAAG
57351 TGGTCATTGT CTCTGCAGAC TGCAGAGAGG GAGACGGGAG GGAAGGTGTG
57401 TTCGCTCTTC CTGCCAAGGG CCCTAGAGAC AGAGAAGAGG GATGTCTTTG
57451 TCATAAGCGA TCACAGGGGA CTCCTGAGGA CTGGGGAGGG CTCTCTGTAA
57501 CTTGGGAGGT TCCCCAGTAG GTAAATTGAT GGATTTTTCT CCCCCACAGT
57551 GCGAAAACAG GAGATCATTA AGATTACAGA ACAGCTGATT GAAGCCATCA
57601 ACAATGGGGA CTTTGAGGCC TACACGTAAG TAGAGACCCA TTTTTTTTTG
57651 TGACCTAAGT CATCTCCCAA GGCCTTCCCT GCTTCCAGAC AACAATTAGG
57701 ACCCTGGGGA AAGGGAGGTT GGACCTTGGG CAAAGTATCT GAGTTAAGCC
57751 CTCTCCTAAA CTGGGAGCCC TTCCAGGTAG ATTCCCTGAG CTCACCCATG
57801 GTATCCTGGC AGTGGGCCGA AAGCACAGGG CTGAGTGGCT CAGCAGGCAG
57851 GCCTGGAAGA TCTTTGCTGT CTTGTCTGGC ATGGCCACAG GTAGCCTGCT
57901 GCTACTGGAT AGACACCGCT GATAAGGAAG GAAGACAAGT CACTCCATAG
57951 AAGCCTGATA GGCTGCTTTT TTTTTTCTCC CTGTAGGAAG ATTTGTGATC
58001 CAGGCCTCAC TTCCTTTGAG CCTGAGGCCC TTGGTAACCT CGTGGAGGGG
58051 ATGGATTTCC ATAAGTTTTA CTTTGAGAAT CGTGAGTGGG TTCGTGCTGC
58101 TGATATACTC CTGCCTGCCC CTTTACCCCT TTGTCTCTGT CTCCTGCTCA
58151 CCTTCTCATC CCAGTTGCCC ACTTTTCCCT TATTTGACCT TCGTGCTGCA
58201 CTCCTACTCT GTATGCTTGT CCCCTTGTGC CCCGATGGTT GTAGACAGGC
58251 ACCTTTGAAG GCCCTGCTCC TGAGCTCCAA GTGCCATTCA TTCTGCAGCT
58301 GCTTTGTGGC AGTGCCAGTC ACCACAATCA AGCTCACTTA TTTCTTGCCG
58351 GGCGCGGTGG CTTACGCCTG TAATCCCAAC ACTTTGGGAG GCTGAGGCTG
58401 GCGGATCACG AGGTCAGGAG ATCGAGGCCA TCCTGGCTAA CACGGTGAAA
58451 CCCCATCTCT ACTAAAAATA CAAAAAATTA GCCGGGCTTG GTGGCAGTGC
58501 CTGTAGTCCC AGCTACTCGG GTGGCTGAGG CAGGAGAATG ATGTGAACCT
58551 GGGAGGCAGA GCTTGCAGTG AGCCAAGATC AGGCCACTGC ACTCCAGCCT
58601 GGGCAACAGA GCAAGACTCC ATCTCAAAAA AAAAGAAAAA ATTATTTAAG
58651 CCTCACCTCT TTCCAAGACG GATTGGAAGG AAACCCTTTG AGATTAGGTT
58701 GAGATGATCT CAGCACATAA GAACTAAGCT CTGTGTCTGC AGGTTTCACA
58751 ATAGAGGAAA TTAAAACCAG GATAAGAATG TGCAAACCAG GGCACTGTTG
58801 GTGATTTGCG AGATCGGAAG TTGTGGCTAG AATCTTCCTG ACTATGGAGG
58851 AAGGCAGACG TCTTGTATAG GGGGTGGGGT GTACATTCTG GACAGTTCGT
58901 GGAAAATAAG GGGATAAGAA GCTGAATCAT CACCCCCTCC CATCTTTCTC
58951 TCTGCTCTAT GAGACCCTCC CCTTCCTTAT TTTTATCTCT TCCCACTTTA
59001 TGCTGGGCCT TCCCTATCCT GCCCTGAGTT ATAGTTAGTC ACTAACTTCT
59051 CCGCTGGCTC CCACCCTTAT CACATCTCAG CTACATATAT AAACTCTCTG
59101 TTATCTAAGT AATTCTATTA GCCAGAAGCA ATTCCAGAGT TTATATTAGT
59151 ACTAGGAAGG TGTCATGTAG CCCCTGTCTA ACATTTGAAT TGAACTAAAA
59201 TGTGAATCTC AATAAAAGCA ACACAGTTTT CACAGCATAT GCTGATAATG
59251 GCAATCCAAC TTCTTTTGCC TTTTCCCCAG AGAATCCTGG GAATATCCTG
59301 AGCTTGGTGC TTTGATGATT CTATTTCAGC TTTGGTGCCT TAAAAAAAAT
59351 TACAAATCAA TTTTGAATGG TTTAAGTTCA TGATTTTGTT CTGCAGCCCT
```

FIGURE 3-22

```
59401 AGCTAGGGGT GAGCCAAGCC TTATGAAATC TAAACTCAGC CTAACAGAAT
59451 AGAAAATCTA TAGGCTTTAG TTAAGAGTCA CATGGTCCTG AGTTCAGGTG
59501 TGTGATTTGA GCAAATTATT CCTTGAGCCT ATTTCCTCAT CTTATAATGA
59551 AGAAAATATT ATCCACCAAG AAATACAGCT CGGGCATGTA AAACCCCAGC
59601 ACAATGCCTG ATTAAAAGCG CAGCAGGTAC TGTCACTGTT ACCCATCTTT
59651 CTGTTCCTTT TGGATAAAGG AGACTAATGT AATGTGGCAT CCTGGCCTCT
59701 GGAGGGCGTT CAGGGGTTCG GGGGTGGGGG GGGGCGGTAC TTGGAGATTC
59751 TGGGAGTGGT TGCTTGGGAG ATGGTAAGAC TTGGAAGTGC AGGCTGGGAG
59801 GAAAATGCAG GTGCCCAGGC CTGATGTCCT CTTACCTACC CCACCCTGCC
59851 CTGCAGTCCT GTCCAAGAAC AGCAAGCCTA TCCATACCAC CATCCTAAAC
59901 CCACACGTCC ACGTGATTGG GGAGGACGCA GCGTGCATCG CCTACATCCG
59951 CCTCACCCAG TACATCGACG GGCAGGGTCG GCCTCGCACC AGCCAGTCAG
60001 AAGAGACCCG GGTCTGGCAC CGTCGGGATG GCAAGTGGCT CAATGTCCAC
60051 TATCACTGCT CAGGGGCCCC TGCCGCACCG CTGCAGTGAG CTCAGCCACA
60101 GGTGCACCTG GTTGACGGGG GAGAGGGGCT GGAAGGGCCT GGGATAGGTG
60151 GGGTCAGAGG AAGAAGAGAA GGCTGGGAGG TGGTCCTGGG AGAGGAGGTG
60201 TGGGCCGTCC CAGAGGACTG GCAAAGCCTG GCAGAATGG TGCAATAAGT
60251 TATGCTTGGA AATCAGACAG ACTAGGGTCT GGCTCCGTGA CTCCAAATTG
60301 GATGACCTCA GACAGGTTAC TTCCCCTCCC TAAACTGTTT CCTTAGCTGT
60351 CAAAGAAAGG CAGAGAGTGG TGCCTACCTC ATTTAATCAT TGTGAGGATT
60401 AAGTAAGATA CTATAAGTAA AGCACTTAGT TAGTGCTTAG CAAATGGGAG
60451 GCAGTTTTGT ATTTAAGCAT TAGCTTCACC CACTTTCCCC ACCTTCTCAG
60501 GCCGACTTGG CCATGTGTTT AGCGTGCTAA AGTCGCTGGA ACTCATCTGT
60551 GTGCTCATTG TCCTCTGTTC TGTTACCACA TTCTGTCCTG TTTGACAGGG
60601 GCTTTAGGAG ATTCCAGCCG GAGGTCCAAC CTTCGCAGCC AGTGGCTCTG
60651 GAGGGCCTGA GTGACAGCGG CAGTCCTGTT TGTTTGAGGT TTAAAACAAT
60701 TCAATTACAA AAGCGGCAGC AGCCAATGCA CGCCCCTGCA TGCAGCCCTC
60751 CCGCCCGCCC TTCGTGTCTG TCTCTGCTGT ACCGAGGTGT TTTTTACATT
60801 TAAGAAAAAA AAAAAAGAAA AAAAGATTGT TTAAAAAAAA AAGGAATCCA
60851 TACCATGATG CGTTTTAAAA CCACCGACAG CCCTTGGGTT GGCAAGAAGG
60901 CAGGAGTATG TATGAGGTCC ATCCTGGCAT GAGCAGTGGC TCACCCACCG
60951 GCCTTGAAGA GGTGAGCTTG GCCTCTCTGG TCCCCATGGA CTTAGGGGA
61001 CCAGGCAAGA ACTCTGACAG AGCTTTGGGG GCCGTGATGT GATTGCAGCT
61051 CCTGAGGTGG CCTGCTTACC CCAGGTCTAG GAATGAACTT CTTTGGAACT
61101 TGCATAGGCG CCTAGAATGG GGCTGATGAG AACATCGTGA CCATCAGACC
61151 TACTTGGGAG AGAACGCAGA GCTCCCAGCC TGCTGTGGAG GCAGCTGAGA
61201 AGTGGTGGCC TCAGGACTGA GAGCCCGGAC GTTGCTGTAC TGTCTTGTTT
61251 AGTGTAGAAG GGAAGAGAAT TGGTGCTGCA GAAGTGTACC CGCCATGAAG
61301 CCGATGAGAA ACCTCGTGTT AGTCTGACAT GCACTCACTC ATCCATTTCT
61351 ATAGGATGCA CAATGCATGT GGGCCCTAAT ATTGAGGCCT TATCCCTGCA
61401 GCTAGGAGGG GGAGGGGTTG TTGCTGCTTT GCTTCGTGTT TTCTTCTAAC
61451 CTGGCAAGGA GAGAGCCAGG CCCTGGTCAG GGCTCCCGTG CCGCCTTTGG
61501 CGGTTCTGTT TCTGTGCTGA TCTGGACCAT CTTTGTCTTG CCTTTTCACG
61551 GTAGTGGTCC CCATGCTGAC CCTCATCTGG GCCTGGGCCC TCTGCCAAGT
61601 GCCCCTGTGG GATGGGAGGA GTGAGGCAGT GGGAGAAGAG GTGGTGGTCG
61651 TTTCTATGCA TTCAGGCTGC CTTTGGGGCT GCCTCCCTTC TTATTCTTCC
61701 TTGCTGCACG TCCATCTCTT TTCCTGTCTT TGAGATTGAC CTGACTGCTC
61751 TGGCAAGAAG AAGAGGTGTC CTTACAGAGG CCTCTTTACT GACCAACTGA
61801 AGTATAGACT TACTGCTGGA CAATCTGCAT GGGCATCACC CCTCCCCGCA
61851 TGTAACCCAA AAGAGGTGTC CAGAGCCAAG GCTTCTACCT TCATTGTCCC
61901 TCTCTGTGCT CAAGGAGTTC CATTCCAGGA GGAAGAGATC TATACCCTAA
61951 GCAGATAGCA AAGAAGATAA TGGAGGAGCA ATTGGTCATG GCCTTGGTTT
62001 CCCTCAAAAC AACGCTGCAG ATTTATCTGC ACAAACATCT CCACTTTTGG
62051 GGGAAAGGTG GGTAGATTCC AGTTCCCTGG ACTACCTTCA GGAGGCACGA
```

FIGURE 3-23

```
62101 GAGCTGGGAG AAGAGGCAAA GCTACAGGTT TACTTGGGAG CCAGCTGAGA
62151 AGAGAGCAGA CTCACAGGTG CTGGTGCTTG GATTTAGCCA GGCTCCTCCG
62201 AGCACCTCAT GCATGTCCCA GCCCCTGGGC CCTAGCCCTT TCCTGCCCTG
62251 CAGTCTGCAG TGCCAGCACG CAAATCCCTT CACCACAGGG TTTCGTTTTG
62301 CTGGCTTGAA GACAAATGGT CTTAGAATTC ATTGAGACCC ATAGCTTCAT
62351 ATGGCTGCTC CAGCCCCACT TCTTAGCATT CTTACTCCTC TTCTGGGGCT
62401 AATGTCAGCA TCTATAGACA ATAGACTATT AAAAAATCAC CTTTTAAACA
62451 AGAAACGGAA GGCATTTGAT GCAGAATTTT TGCATGACAA CATAGAAATA
62501 ATTTAAAAAT AGTGTTTGTT CTGAATGTTG GTAGACCCTT CATAGCTTTG
62551 TTACAATGAA ACCTTGAACT GAAAATATTT AATAAAATAA CCTTTAAACA
62601 GTCCATTGTG TTACTGCTGT TGGAGGTTTA CGGCCAGAGG CGTAGATTTT
62651 AGCAGCCTGG GTTACCAGGT TGGAGAGAGT ACCTCCTCCT ACTCCCTTTG
62701 GGTACTTTTG AGAATAAAAC TTCCTCATGC CTGTAATCCC AGTACTTTGG
62751 GAGGCCGAGG CGGGCGAATC ACGAGGTCAG GAGTTCGAGA CCAGCCTGGC
62801 TAAT  (SEQ ID NO:3)
```

FEATURES:
Exon:     1690-1694
Intron:   1695-2000
Exon:     2001-2095
Intron:   2096-14208
Exon:     14209-14268
Intron:   14269-21854
Exon:     21855-21909
Intron:   21910-22781
Exon:     22782-22847
Intron:   22848-25768
Exon:     25769-25841
Intron:   25842-25986
Exon:     25987-26089
Intron:   26090-26492
Exon:     26493-26576
Intron:   26577-27019
Exon:     27020-27114
Intron:   27115-27753
Exon:     27754-27876
Intron:   27877-32559
Exon:     32560-32643
Intron:   32644-32889
Exon:     32890-32932
Intron:   32933-35499
Exon:     35500-35562
Intron:   35563-37589
Exon:     37590-37633
Intron:   37634-46979
Exon:     46980-47012
Intron:   47013-51017
Exon:     51018-51062
Intron:   51063-53371
Exon:     53372-53420
Intron:   53421-55458
Exon:     55459-55572

FIGURE 3-24

```
Intron:  55573-57549
Exon:    57550-57625
Intron:  57626-57986
Exon:    57987-58081
Intron:  58082-59856
Exon:    59857-60086
```

CHROMOSOME MAP POSITION:
Chromosome 10

ALLELIC VARIANTS (SNPs):
DNA

| Position | Major | Minor | Domain |
|---|---|---|---|
| 1603 | G | A | Beyond ORF(5') |
| 8632 | T | - | Intron |
| 19366 | G | A | Intron |
| 23770 | T | C | Intron |
| 31013 | A | T G | Intron |
| 33206 | T | A | Intron |
| 33263 | G | A | Intron |
| 33859 | C | A | Intron |
| 37254 | T | C | Intron |
| 40809 | C | A | Intron |
| 41025 | T | C | Intron |
| 42232 | T | C | Intron |
| 50477 | G | A | Intron |
| 55352 | A | G | Intron |
| 55914 | A | G | Intron |
| 56633 | G | A | Intron |

Context:

DNA
Position

1603     ACCCCCACCCGCGGCGCCGAGCCCGGCCACTGCAGCCCCCGCCCCGCCCGCCCCCCCAGA
         CGTTTCCAGAGCTCAGAGTGCGAGCTCCCGTTTGACGGGACGTCAAGGAAAATAGCATG
         GGAAGGGGAGTTCTTGATGTCTGACTGTGTCCTCTCTTCCCTTGCTGTCAGTTGAGCCGG
         GATGCAGTGAGATGAAACCGGCTGTGGGGGGGTTTGAGCCTCACTTTGCCCCATGGTTGA
         GGGAGATTTCTCTTTCAGGGGATGATACCCTCTTTTTTAATCTTTCCTTCCCCGACCTTCA
         [G,A]
         CTGTTCCTGCTGAGAGAAGGGCAGGGTCTCTCTGCTCCCTTCTGCCCTGGTTCTCTTGGC
         CGGGACCGCAGGGCTGTCTGAGATGCAGCAGGTGTGTGTTTTCAGCATCGCCCACCCGCT
         CCTGATGTGCAGCCTGAGGTGGAGGCTGTTGCCTTGCCCAGGGACTGGATGAGGGGGTGG
         GAGCGCGGCACGCCACCCACATCTGTTCAGTGTCCTGCGGTGGCCGCGTCCTTTTGCCTC
         ATGTTGGATGGTGGTGGTCACAGCGCCGGTGTGTGTGCATGTACGTGAGTGTGACTAGAG

8632     GACGGCGGCCTCTGCTGCTTGGGAAGAAGATGAAAGGCACTCAGGAGGGCAGCAAGTGAG
         GCCGCCTCCCATGGAGCCCTGAAATCAGTGGGGTTGCAGGAAGTTTCTCACATCCATGTT
         TAGGGTCATAGGCACAGACCTGCAAAATACCCTTTGCAAAGTTAAGAATGTCTTTGAGAT
         TGGAACTTGGGAGAGTCCTCAGTCAGAGTAGGAATGTGCATCCTTTCCCACGTACAGAGG
         ATTGTATGTTTACGTGGCAGCAGGATCTTATTTGAAGCTAGTGCTGGCATTTGTGTTTTT
         [T,-]

FIGURE 3-25

```
        TTTTAGGAAAATGTCACTAAGTCAAGCAGGCCCATCCCTGAGAGGGCCATGGAGAATCTG
        TGGCCAGCCCTCCCTGGCCCCCTGACCTGGCAGAGGAAGGAAAGGGCATTGGAGTAGGCT
        TCTGTCTTCAGGCCAGAGGGGGAGGTGGTTCAGGGGCAGGCTTGGTGCACCCCTTGGCTG
        CAAGCTATCACCTCCCTATCTGCTTCCTCTTTTCTGCCTCCCCTGGTGCATCTGGTCACT
        TCTTGCTGCCCTTCCTGTGAAATCGTGGCACCTTGGACCAAGTCCTGAAGCACTTGGGCA

19366   CTCAGGAGGCTGAGACAGGAGATGGCTCAAGACCAGGATCTCCAGCCCAGCCTGGGCAAC
        ATAGTGAGACCCTGTCTCTTAAAAAAAAAAAGAAATAATGAATCTGCTGTTGCTAAATAG
        GCACTTAGAATGGCACAGTCATTTCTCCTCTTGTCTTCAGTGTCCTGTTAATTTCTTTAC
        AAATTAAAAAAATGTCGATAGCAGTCTTATTCAGATACAGCTTCCTCCATCCCTCCTTGT
        CTTGGCAGGTGCCTTGCTCTGGGGCACACATCAAAGCTGTTCTCTCTGCTGGGTGGCCTA
        [G,A]
        AAGGATTAGTCTTCCTTTGCTGCTCCTTTCTTCTAATTCCCTTCCCCGGCTTCCTCCCAC
        CTGGGCTCTGTGTGTGGCCTTCCTGGAGAAGGGCAGACGCCAATGACTCCATGTCTAGGC
        AGAGGCCTGGGTGCCTGCACTTCTTGCCCTGTTCTTGGCCTTGCTGTGCTGGGCGGGGGC
        AGGGTGGTGTGGGGCATGGGGTGGTGTTGGGCATGGGGTGGGGTTCTGGCTGAGGCAGGG
        CTCAGTGCCAGGCCCAGGCAGAGCTGAGTGGCTCCACTTCTCTGAGATGGTTGTCAGCAT

23770   CCCCCTCTGCCCTTTTCTTTCCTTTGACAAATTCTGGTGTGCTCAAGCCACTGTGCTGAG
        GCTCTGGCATGATCCAGAGGTGCAGAAGACATGGTTTCTGTCCTGAGGGAGTGGAGAGTT
        CTGGGCTGATAATCCAACCATAGAGCCCCGGGAGCTTTCAGCCTCTGTCACCTTGTCCCT
        AGACCACCATGACCAGCCTTGCCGTGGGGCTCCTCCAACTTGAGGACCGTTCCCCGGCCA
        CATGCCTCAGCCTCTGCCCTCCCTGGAATCCCTGGTGCCTCCCTCACCCACGCTCTCAGG
        [T,C]
        GCCTGTTCAGCCTGCCTTTCCCGCCTTGGCTCTTCCCCCAGCCTTGCTTTTCTCGAGGGT
        GATGTCCCTACAACCTGGTTTTGATCATCCTGCCTGCAGCTTATCTGGCTTATGTGGCAG
        CTCTGGCTGCTTCTGGAGAGTGGGGGAGTGCAGCTTCCTCACGAATTTCTCAACCTTGAG
        AGGCCAATGTTTGCTGATCAACTTCAGATGCTTCAGCCTCGGGAAGAATTCTCAAGTGGG
        GAGATGAATTCCAGTGCCAGCAGGGGAGGACGAGGCTCTGGGACGGAGGAGGCAGTGATG

31013   TCAGGAGCGGTGGCTCACACCTGTAGTCCCAGCACTTTGGGAGACCAGGGTAGGTAGATC
        ACTTGAGCCCGGAAGTTTGAGACCAGCCTGGGCAACATGGCAAAACCCCATCTCTACAAA
        AAAAAAAAACTTTAAAAATTAGCTGGTTGTGGTAACGTGCCTTAGCTACTTGGGAGGCTGA
        GATGAGAGGATCACCTGAGCCTAGAGAGGTGGAGGTTGCAGTAAGCCATTATTGTGCTAC
        TGCACTCCAGCCTGGGCAACAGAGTGAGATGCTGTTTCAAAAAAAAAAAAAAATTTTTTT
        [A,T,G]
        TTTAAGGAGAGGCTTAACTATAATCTATAGAGAAGAATCTAGTCCAGAGGAAAGAGTTGA
        AGATCCTTGCTAATTGAGGAAGCAAAGGTTTGGACAGCAGAAAAAGAGAGGGGGCTCCTG
        AGCCAAGGGCAGGGGGTCCATCCCGGGGATGACCATGATCCCCCTGAGACTTCTATTAGT
        GTGGAGGCAGGTGAAGATCGGCTTGTGAGTGGAAGTCTGAGCTGAAAGGGGTTCTTGCTG
        ATGACCTCTCATTTTGCTTTTGGAGAAATTTACACCGAGGAGGAGGTAAAATGAGAGACT

33206   CCATGCTTGTCTCCAGGAACTTCTCAGGTATGTTTTCCCAGCTGTGTACTTTGATTATGC
        CGAGGTGAGTGGATCAGGAATGGGCTGTTGCCATCCCGGGCACCGCTGGGTTTCCTCGGC
        GTCCTGGGCCACACCTTGACCAGGGCGAGTGAGGATCCTGTTTTGAGGGGCTGCTGCTGC
        TGCTGAGTCCTGCTCCTGAGATTCAGGGGCTGGACTCACATTTGTGAATTGTTTCCTAG
        AACTTCCCAAGGAGTAGCCTGCCCAACTTGCTATGTACCTTGTTTCTCTGGATTCTTATT
        [T,A]
        AACTCTCTGAAGACTCTCAGCACTTTACAGATTTTAGCCATTCTAGGATCTTGGAGGATG
        TGCTGGGGGAAGAAAAGAGAGATGAGGTACAGTGAGTCTTCTCAATTGCCAAATTGCCAC
        CATTCATTTGCCTGCTGGGACGATCTCTTACTTCATTTTGTCCAAGTGGAGATGACTAAT
        AGAAATTATTCCAGATGTTTAAACCTTTTGTGGCGACTTGTGCTTAAAATAGTCCCTGAG
        ATACTAGCTATAACAGTGAAGAAATAAAGACCAGCAGGAGAGAGGGAAAGGAACTTGCTT
```

FIGURE 3-26

33263  TGCCGAGGTGAGTGGATCAGGAATGGGCTGTTGCCATCCCGGGCACCGCTGGGTTTCCTC
GGCGTCCTGGGCCACACCTTGACCAGGGCGAGTGAGGATCCTGTTTTGAGGGGCTGCTGC
TGCTGCTGAGTCCTGCTCCTGAGATTCAGGGGGCTGGACTCACATTTGTGAATTGTTTCC
TAGAACTTCCCAAGGAGTAGCCTGCCCAACTTGCTATGTACCTTGTTTCTCTGGATTCTT
ATTTAACTCTCTGAAGACTCTCAGCACTTTACAGATTTTAGCCATTCTAGGATCTTGGAG
[G,A]
ATGTGCTGGGGGAAGAAAAGAGAGATGAGGTACAGTGAGTCTTCTCAATTGCCAAATTGC
CACCATTCATTTGCCTGCTGGGACGATCTCTTACTTCATTTTGTCCAAGTGGAGATGACT
AATAGAAATTATTCCAGATGTTTAAACCTTTTGTGGCGACTTGTGCTTAAAATAGTCCCT
GAGATACTAGCTATAACAGTGAAGAAATAAAGACCAGCAGGAGAGAGGGAAAGGAACTTG
CTTAAATTTGCATAAAGAATTGGGAGAGGTGGGACCAATAATTTGTAAATCATACTTGAC

33859  TTGACATTTATTTTTAAGATGCAAGACACTCCACTCCCCTCTTGCCCCCACCCTCACCCC
AACCCCTATTATTGTTTGCCTTCAATTGGGAAGCACAGTGGCTTTTTTGTGAGGAAAAGA
TTAATGTCGAGACTGAAGACAGAGAGGGCTCTGCCCAGCTTGCCATCTCCCCCGGTCCTC
CCTCCCTCTAACCCCTTGCCTCACTGTTTTGGTTCAAGACCCCCCCTTCTCCTTCCCATA
ATAAGACTCCCTCCCTTGCTTCCCCTCTGCACCACCATGGAAAGGGGGTTGTGTGGGAGC
[C,A]
TAAGCCACCACTCAGTGGGAGCCACTTCTGAATACCCGTCCTGCTGGGCTCGCCTGCGCT
GGCTCCAGGTAACGCCAGGGCCTTGGCTGTGAGGATGCTGCAGGCAGGGAGCCTAGGGCT
TCGTGGTGTAGCCTGAGAGCCATGGAGCTCCGGAAGGCCAGGGCTGGATAGTGAGCCCGG
GGCTGGTGGTGCCCTGCCCTAGGCCTTCTCCTTTGACCCTGGTTTGGGGCTTGATCTTGT
GTCATGGGTACCCACGACGGGCATACTGTGGTGTGGCTCCACCTCTCGCAGATGGGAACA

37254  CATTATTCTGCCGAGTCCTTCCTGCTCACAGGTCCAGAGAGTGGACACTGGGGAAAGGGT
GGCAGCTAGGACCCAGTGAACCTGGTGAGGACCTGCTCAGTGAAGGCTTCAACCCCCTGG
CAAAACCCTCCTGTAGGTGGTCCTGGTTTCTGTGTCTGTGTCTGTCTGTCCTCTGGTCTC
CTGTGTGAACTGTGACACTCTGCTTCTTGAGAACACTCAGGAGATGTCTTGCATCCTTGC
AGTTTGGCCATCCAGAGAACTTCCATGGCACCTAGGGATGGAGCCCTCACTCTTTCACCC
[T,C]
GGCACTCTGCTTCCAGGCCTGGGTGGAAGCTGTCAAAGGCAGAGTCCCCAGTGCCCCAGG
CGGCTCCAGTACTGAGCATGGTTTCTCCTCTAAGTGTCGTGCATCCATGCCCTCCTCCAC
GCAGAGGAGATCCTGAGGTGCCACCCTGAGGGCTCTGACGCCACTCAAGATCCCCTTCTT
GCTGAGAGGCTATAGGAAGTGCCTCTTTTGGGGGTTTCGGGAGACCCTTGGCCCCCTTGT
CAGACACAGCACTCTCTTGTGGATCTGGCTGCCGGACTTCAGGTTGGGGAGAGGGTACAA

40809  GTCGGCAAAGGAAACAGAGGAAGGACAGAGAGGTAGGGGAAAAGAGAAATGTGCAGCAG
CTGCAGCTCTTCCAGGAACCCTGAGGATGAGGGCTGGGCAGACACATCATTAGGTAAAGG
CTTTAAATGAGGACGTGCGTGGGGAACCTAGCCCTGCAATGTGTTGTGTGTCTGACCCTG
ATATGTGCTCAGTAAATGAGTTTTATGCCACATTCTTTTGAGAAAAGAGCTTCAATATCA
TGGTGGGAACCAGAGGCCAATGATCACCCAAAATTAAAAGGCCAACCGCGTATTCGCAGC
[C,A]
GTTGTGATGGGAGGGGTTAATATTTTTATTGAAAGAGTTTCTGTGACAAATAATCCCTCT
TAAAACCCAGTAGAAGCTGGGCGTGGTGGCTCACGCCTGTAATCCCAGCACTTTGGGAGG
CCGAGGCGGGTGGATCACGAGGTCAGGAGATCGAGACCATCCTGGCTAACACGGTGAAAC
CCCATCTCTACTGAAAATACAAAAAATTAGCCGGGTGTGGTGGCAGGCGCCTGTAGTCCC
AGCTACTTGGGAGGTTGAGGCAGGAGAATGGCGTGAACCCGGGAGGCGGAGCTTGCAGTG

41025  TTTGAGAAAAGAGCTTCAATATCATGGTGGGAACCAGAGGCCAATGATCACCCAAAATTA
AAAGGCCAACCGCGTATTCGCAGCCGTTGTGATGGGAGGGGTTAATATTTTTATTGAAAG
AGTTTCTGTGACAAATAATCCCTCTTAAAACCCAGTAGAAGCTGGGCGTGGTGGCTCACG
CCTGTAATCCCAGCACTTTGGGAGGCCGAGGCGGGTGGATCACGAGGTCAGGAGATCGAG
ACCATCCTGGCTAACACGGTGAAACCCCATCTCTACTGAAAATACAAAAAATTAGCCGGG
[T,C]

FIGURE 3-27

```
        GTGGTGGCAGGCGCCTGTAGTCCCAGCTACTTGGGAGGTTGAGGCAGGAGAATGGCGTGA
        ACCCGGGAGGCGGAGCTTGCAGTGAGCTGAGATTGTGCCACTGCACTCCATCCTGGGTGA
        CAGAGCAAGACTCCGTCTCAAAAAAAAAAAAAAAAAAAAAAAAAAAACCCAGTAGATAGGC
        TAGGTGTGGTGGCTCACATCTGTAATCCCAGCACTTTGGGATGCTGAGGTGGGCTGATCA
        CTTGAGGCCAGGAGTTCGAGACCAGCCTGGCCAACATGGTGAAACCCCCTCTCTACTAAA

42232   GGAAACGTAGTGAGACCCCATCTCTTAAAAAAAAAAAAAAAAAATTAGCTGAGTGTGGTGG
        AACGTGCCTGTAGTCCCAGCTACTTGGGAGGCTGAGGTGGGAGGATTGCTTGAGCCCAGG
        AGGCTGAGGTTACAGCCAGGATCACACCACTGCGCTCCAGCCTGGGTGACAGAGTGAGGC
        TCTGTTTAAAAAAAAAAAAAAAAAGAGAGAGAAGAAAAAAAAAGATTGGAGACAATTTGAAA
        AGCCAGTAAGGAGCCAGACACAGTGGTGCGTACCTATAGTCCCAGCTACTCAGGAGGCTG
        [T,C]
        CGCAGGACAGAATTGCTTGAGCCCAGGAATTCGAGGCCAGCTGGGCAACATAGTGAGACC
        CCCAACTCTTAAAAATGTTTTTTAAATTTAAAAATAAAAAGATTTTTTAAAAGCCAGTAAA
        TGACTAAATAATTATGGGAAATCTACTTAATAAACTATTCAAAAGTTATTAATTTTCATG
        ACCGTAGGGATATTTTAAGTGAAAAATAAAGTGCAGAAATGTTTTATATTAAGTGAAGGA
        AGTGGTATATAAAGGAGTACAGACAAGCCAGGCACGGTGGCTCACGCCTGTAATCCCAGC

50477   TTGGGACCTGAACATCAGTTCTTGGAGGCCCCCTTGTAAAACCTGCCTCAGCCTCTCCTT
        TGCAAAGCCAGAAACAGGAAAGAGGGCTGGGGTCCCCACCTCTGGATGGTGCTGAGGTCT
        CCAGGCTCCTGGAGTGCCTCATGCTGGCTAAGTTCTCTCTGGGCTCCTCCAGGGGTTCTG
        TGTGCTCTTGGAGGTCCCTCTGCTAGTGGTGGCTAACTAGAGAGTCAGCAGGGGGGTGAC
        TGGGAAAGAGGGAGAGGTGATGTTGCCTGCTACTCCCCTCCTTGCGGACCCTCATACCAC
        [G,A]
        TGACGTGGCGGCGTGGGGCCAGGAACTAGGGAAGGCAGAAGGCGGGCGCAGTGGGCAGCT
        CTCTGGGCTCAGCTTGCTGAGGGGGCCTCCTGTCCTGGCTCTTTCTGGGAGACCTCATTC
        TTCTGCCCATGTTCCTGCCTCACACATTCCCCGTGATGAACGCTGTGGGCGGGGCCCGGC
        CTGTGCCCTCAGTCCCACAGCTCCTCTAGTGTACCTGCCCCGTGGGAACCCCATGTGGAA
        AGAGCCCTCAGAACTGACAGGAATCAGGGACAGAGGCCCTTGCTGTCAGCCTCCTGGGCA

55352   TAGTAGCTCCAGGCCCCTGTGAGTGAGGTCAGATCAGTTTTTGATTCCGGCACTGCTGGCA
        ACATAGGAGGCGCTGTCACTGCTGGGCTCTGGACCCTGTGGCCTGGCCCCCTGGAACATC
        TTCCCCGGGATCAGGGGTCCTTGGACAGGCTGTTGTAAGGCTCGTCTGGAAGCCACAGCC
        CAGGTCTGGGCACCTGCCTGGTGCCCTCAGCTGGGAGGCCTCTCTGGCAGAGGCGGCGGC
        GTGGGATGTCGTCCAGTGTCCACAGCAGCCTGAGGCGAGGCGTCCCCTTGCCCCGGCTCT
        [A,G]
        CAGCGCCATGGGCTCGGGGCCTGTCTGGCTTGCTCGCTCACCTGCCTTGTTCTGTTTGTT
        TTGGCTGCTCTGCCTTGCCCTGCCCTGCCCTGCCCTGGCTGGCTAGCTGCCCCGCTCCGC
        ACTGGGAATGGCAGCTCGGTGCCTGAAGGACGGAGCTCCCGGGACAGAACAGCCCCCTCT
        GCAGGCATGCAGCCCCAGCCTTCTCTCTGCTCCTCAGCCAGTAAGTGTGAGGGAGGCACA
        TTCTGGCTTCCGTCTCCCTGGCTCGTCCTGAAGCCCCTCAGGGACCCCCACCACAGCTGT

55914   CTCGTCCTGAAGCCCCTCAGGGACCCCCACCACAGCTGTCAGTCCCACCCACCTGCCCGT
        GGTAGTAAGCTCTGGGAGCATGGCCTCTGCTGGGGGTGGGGGGTAGACTGGAGGTGCTGT
        TGAGACCAGGCAGGGGCCCCTGAGTCTGGGGCCCAAAGAAATATGAGAAGTGTGGGTGGA
        AAAACATGGCCTGGGATGAGGGGAGTAGAAAGCCCCCAGGATGTGCAGTGGGCCTTGCCT
        CAGCGCTGAGCCAGGAAGAAGGGCAGAGTCGGAAGTCAGGTCTGTGGGGGTGGGAGTGGG
        [A,G]
        TGATGGGGAAATCGTGACAGCGAGGAACTGTGTTGGGGATGTAGTGCTTCCTGAGTCTCA
        GCATAACAGTATTAAGAGCATGGGGTCAGAGGCAAGATAGATCTGAGTTTAAATCCCAGC
        TACACTGCCTTCAAGAGTGTGAAGTTTAACCTCCCAGAGCTGCAGGTTCCTTATCTGTAA
        TGTGGAAATAAAATGGCACGCACCTCAGAGCCTTGTTAGATAAAAGACAAGGCAGTAGGA
        AGTCTTGATACGGTGCCTCGATGGGTTATCAGTAGCTCATCCTCATATTTCTAGTTACGT
```

FIGURE 3-28

56633  TGGGGTTGGAGAGGGTGTGTGTGTTGTGGGTGCACACCTGCCTGCTGCTTTTGGAAGCCG
ATCGAACTCCTTGCTTCCCTTAACCTGCTGCTTGCTCACCTGGAGCTGTGGCCTAGCGGG
GCTGACGGCTGTGGGGCCCCCTCCTGGATGTGCCTTTGGCTGCGCTGCCCTGTCCCAACT
GTGCTGCTTGGCTGTGCTGGCCCGGCTGGGCCGTGGTGGTGCTGTTCTAACGCTTGCAGT
TGTCTTGCAGCCTTTTGCTCCTGTGAGGAAAGGGTTGTGGCCTGGCCCCGCCCAGGGCTC
[G,A]
GGTTAGGATGAGCCCAAGCTCAACCCAAGCTCTCCCTTACCCTGGTGGCAGCCCCTGCTG
GTAGTGGCATTCCCTATAAGAGAAGCCCATGCCGGCAGGACATCACCAGCTGTCCCTTGG
CTTTGGATGGGTTGGGGAGGAGGCCTCTGGAGGGCACCACCTCTGCCTGCCTGTCAGTCT
GAGCCCTGTCTGGTTTTCCTGAGGAACACGTCCTGGCAATGAGAGCTGGTGTGAAATGTG
CAGCTTTCCCAAGCCTCGAGAGGTAAATGGAGCAGCCTCTCTGGTACAGGCTGTCCCAAG

FIGURE 3-29

SEQUENCE LISTING

<160> NUMBER OF SEQ ID NOS: 4

<210> SEQ ID NO 1
<211> LENGTH: 2061
<212> TYPE: DNA
<213> ORGANISM: Human

<400> SEQUENCE: 1

| | | | | | |
|---|---|---|---|---|---|
| cggtgctgcc | gggctcagcc | ccgtctcctc | ctcttgctcc | ctcggccggg | cggcggtgac | 60 |
| tgtgcaccga | cgtcggcgcg | ggctgcaccg | ccgcgtccgc | ccgcccgcca | gcatggccac | 120 |
| caccgccacc | tgcacccgtt | tcaccgacga | ctaccagctc | ttcgaggagc | ttggcaaggg | 180 |
| tgctttctct | gtggtccgca | ggtgtgtgaa | gaaaacctcc | acgcaggagt | acgcagcaaa | 240 |
| aatcatcaat | accaagaaat | tgtctgcccg | ggatcaccag | aaactagaac | gtgaggctcg | 300 |
| gatatgtcga | cttctgaaac | atccaaacat | cgtgcgcctc | catgacagta | tttctgaaga | 360 |
| agggtttcac | tacctcgtgt | ttgaccttgt | taccggcggg | gagctgtttg | aagacattgt | 420 |
| ggccagagag | tactacagtg | aagcagatgc | cagccactgt | atacatcaga | ttctggagag | 480 |
| tgttaaccac | atccaccagc | atgacatcgt | ccacagggac | ctgaagcctg | agaacctgct | 540 |
| gctggcgagt | aaatgcaagg | gtgccgccgt | caagctggct | gattttggcc | tagccatcga | 600 |
| agtacaggga | gagcagcagg | cttggttttg | ttttgctggc | accccaggtt | acttgtcccc | 660 |
| tgaggtcttg | aggaaagatc | cctatggaaa | acctgtggaa | atctgggcct | gcggggtcat | 720 |
| cctgtatatc | ctcctggtgg | gctatcctcc | cttctgggat | gaggatcagc | acaagctgta | 780 |
| tcagcagatc | aaggctggag | cctatgattt | cccatcacca | gaatgggaca | cggtaactcc | 840 |
| tgaagccaag | aacttgatca | accagatgct | gaccataaac | ccagcaaagc | gcatcacggc | 900 |
| tgaccaggct | ctcaagcacc | cgtgggtctg | tcaacgatcc | acgtggcat | ccatgatgca | 960 |
| tcgtcaggag | actgtggagt | gtttgcgcaa | gttcaatgcc | cggagaaaac | tgaagggtgc | 1020 |
| catcctcacg | accatgcttg | tctccaggaa | cttctcagtt | ggcaggcaga | gctccgcccc | 1080 |
| cgcctcgcct | gccgcgagcg | ccgccggcct | ggccgggcaa | gctgccaaaa | gcctattgaa | 1140 |
| caagaagtcg | gatggcggtg | tcaagaaaag | gaagtcgagt | tccagcgtgc | acctaatgga | 1200 |
| gccacaaacc | actgtggtac | acaacgctac | agatgggatc | aagggctcca | cagagagctg | 1260 |
| caacaccacc | acagaagatg | aggacctcaa | agctgccccg | ctccgcactg | ggaatggcag | 1320 |
| ctcggtgcct | gaaggacgga | gctcccggga | cagaacagcc | ccctctgcag | gcatgcagcc | 1380 |
| ccagccttct | ctctgctcct | cagccatgcg | aaaacaggag | atcattaaga | ttacagaaca | 1440 |
| gctgattgaa | gccatcaaca | atggggactt | tgaggcctac | acgaagattt | gtgatccagg | 1500 |
| cctcacttcc | tttgagcctg | aggcccttgg | taacctcgtg | gagggatgg | atttccataa | 1560 |
| gttttacttt | gagaatctcc | tgtccaagaa | cagcaagcct | atccatacca | ccatcctaaa | 1620 |
| cccacacgtc | cacgtgattg | gggaggacgc | agcgtgcatc | gcctacatcc | gcctcaccca | 1680 |
| gtacatcgac | gggcagggtc | ggcctcgcac | cagccagtca | gaagagaccc | gggtctggca | 1740 |
| ccgtcgggat | ggcaagtggc | tcaatgtcca | ctatcactgc | tcaggggccc | ctgccgcacc | 1800 |
| gctgcagtga | gctcagccac | agggctttta | ggagattcca | gccggaggtc | caaccttcgc | 1860 |
| agccagtggc | tctggagggc | ctgagtgaca | gcggcagtcc | tgtttgtttg | aggtttaaaa | 1920 |
| caattcaatt | acaaaagcgg | cagcagccaa | tgcacgcccc | tgcatgcagc | cctcccgccc | 1980 |
| gcccttcgtg | tctgtctctg | ctgtaccgag | gtgttttta | catttaagaa | aaaaaaaaa | 2040 | aaaaaaaaaa aaaaaaaaa a                                                                    2061

<210> SEQ ID NO 2
<211> LENGTH: 565
<212> TYPE: PRT
<213> ORGANISM: Human

<400> SEQUENCE: 2

```
Met Ala Thr Thr Ala Thr Cys Thr Arg Phe Thr Asp Asp Tyr Gln Leu
  1               5                  10                  15

Phe Glu Glu Leu Gly Lys Gly Ala Phe Ser Val Val Arg Arg Cys Val
             20                  25                  30

Lys Lys Thr Ser Thr Gln Glu Tyr Ala Ala Lys Ile Ile Asn Thr Lys
         35                  40                  45

Lys Leu Ser Ala Arg Asp His Gln Lys Leu Glu Arg Glu Ala Arg Ile
     50                  55                  60

Cys Arg Leu Leu Lys His Pro Asn Ile Val Arg Leu His Asp Ser Ile
 65                  70                  75                  80

Ser Glu Glu Gly Phe His Tyr Leu Val Phe Asp Leu Val Thr Gly Gly
                 85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
    290                 295                 300

Leu Thr Thr Met Leu Val Ser Arg Asn Phe Ser Val Gly Arg Gln Ser
305                 310                 315                 320

Ser Ala Pro Ala Ser Pro Ala Ser Ala Ala Gly Leu Ala Gly Gln
                325                 330                 335

Ala Ala Lys Ser Leu Leu Asn Lys Lys Ser Asp Gly Gly Val Lys Lys
            340                 345                 350

Arg Lys Ser Ser Ser Ser Val His Leu Met Glu Pro Gln Thr Thr Val
        355                 360                 365
```

-continued

```
Val His Asn Ala Thr Asp Gly Ile Lys Gly Ser Thr Glu Ser Cys Asn
    370                 375                 380

Thr Thr Thr Glu Asp Glu Asp Leu Lys Ala Ala Pro Leu Arg Thr Gly
385                 390                 395                 400

Asn Gly Ser Ser Val Pro Glu Gly Arg Ser Arg Asp Arg Thr Ala
                405                 410                 415

Pro Ser Ala Gly Met Gln Pro Gln Pro Ser Leu Cys Ser Ser Ala Met
                420                 425                 430

Arg Lys Gln Glu Ile Ile Lys Ile Thr Glu Gln Leu Ile Glu Ala Ile
                435                 440                 445

Asn Asn Gly Asp Phe Glu Ala Tyr Thr Lys Ile Cys Asp Pro Gly Leu
            450                 455                 460

Thr Ser Phe Glu Pro Glu Ala Leu Gly Asn Leu Val Glu Gly Met Asp
465                 470                 475                 480

Phe His Lys Phe Tyr Phe Glu Asn Leu Leu Ser Lys Asn Ser Lys Pro
                485                 490                 495

Ile His Thr Thr Ile Leu Asn Pro His Val His Val Ile Gly Glu Asp
                500                 505                 510

Ala Ala Cys Ile Ala Tyr Ile Arg Leu Thr Gln Tyr Ile Asp Gly Gln
                515                 520                 525

Gly Arg Pro Arg Thr Ser Gln Ser Glu Glu Thr Arg Val Trp His Arg
530                 535                 540

Arg Asp Gly Lys Trp Leu Asn Val His Tyr His Cys Ser Gly Ala Pro
545                 550                 555                 560

Ala Ala Pro Leu Gln
                565

<210> SEQ ID NO 3
<211> LENGTH: 62804
<212> TYPE: DNA
<213> ORGANISM: Human
<220> FEATURE:
<221> NAME/KEY: misc_feature
<222> LOCATION: (1)...(62804)
<223> OTHER INFORMATION: n = A,T,C or G

<400> SEQUENCE: 3 ttgccctgg cctggtctcc ctgatcaacc cgcgcctgaa gggtttcttt ctaataatgg      60
ccctggtgct tgcgcaagtc tagactgtca gctcccagag ggaaggcggc tgcagctgg    120 ctctgcgcag gctgggggcg cctcccgggc gtgcagcctg cacaggctc cttgaccttg    180 gctctctccc cacgtgctag gagcccggtt ggggctcgg gacccgcgtg taggaccgt    240 ccagagaggt cagtggtcca gactcctaca ctcctaacac atgcaccctc gcatgcacgt    300
tcccgagccc gcgcggggtc cgccccggga caagcccata agtcgcgaac cttccagnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
```

```
nnnnnnnnnn nnnnnnnnnn nnnnnnnnnn nnnnnnnnnn nnnnnnnnnn nnnnnnnnnn    900
nnnnnnnnnn nnnnnnnnnn nnnnntgtaa gccaccggcg ccgggcggtc tcgacattaa    960
atttcaaaat gttttctccg gtttgtcact tgtggtttta ctatgttcaa tgggtctcac   1020
caagcaattt tgcaaaatag ttaacttatt ctcttttcct tacatgactt cttgactttg   1080
agccatagtt aggaaaggtt tgctcactct cacattagag taaaatttat ccacattttc   1140
atctaggatt agtgctcatt tttttattat tatgaatatc ttcttcattt ggggtttgtt   1200
catgtatatt ccatgaacaa tggacgcggg tgcagcattt tagcatcagc tatcccttc    1260
ccatccgcaa tgagctggcc gctgcagcag ccccggcccc ccaccccac ccgcggcgcc    1320
gagcccggcc actgcagccc ccgccccgcc cgcccccca gacgtttcca gagctcagag    1380
tgcgagctcc cgtttgacgg ggacgtcaag gaaaatagca tgggaagggg agttcttgat   1440
gtctgactgt gtcctctctt cccttgctgt cagttgagcc gggatgcagt gagatgaaac   1500
cggctgtggg ggggtttgag cctcactttg ccccatggtt gagggagatt tctctttcag   1560
gggatgatac cctcttttta atctttcctt ccccgacctt cagctgttcc tgctgagaga   1620
agggcagggt ctctctgctc ccttctgccc tggttctctt ggccgggacc gcagggctgt   1680
ctgagatgca gcaggtgtgt gttttcagca tcgcccaccc gctcctgatg tgcagcctga   1740
ggtggaggct gttgccttgc ccagggactg gatgagggg tgggagcgcg gcacgccacc    1800
cacatctgtt cagtgtcctg cggtggccgc gtccttttgc ctcatgttgg atggtggtgg   1860
tcacagcgcc ggtgtgtgtg catgtacgtg agtgtgacta gaggtctggt ggtgggagca   1920
tcatcgtccc cagacttgaa gtgtgtctgt gtcactctgc cctgctccgt gtcccagttc   1980
ttttccccttt ctccctccag gggtgctttc tctgtggtcc gcaggtgtgt gaagaaaacc   2040
tccacgcagg agtacgcagc aaaaatcatc aataccaaga aattgtctgc ccggggtgag   2100
tgttccctgt cttgacctct tcctgagggt gcctccaggg gccatggttt cttttgagga   2160
agccccagga attgggggtt gtgcgttta gcacttggag aggagttgga atttcagact   2220
ggttggactt tgtgtcaggc tgaagccaga aaaggagttg catggggac tggaagcgcc    2280
caggtacaaa agaatgaagg aagagatgca agtagctgca gtggccccca aaggctcaag   2340
ggagttcggt cttcagggag gtggaggata tgggggtagt gggtggtaca gaatggggag   2400
ctcttaattt ggggcatttg gagcctctcc ctttggggca gtggtggcta ctgcaggcct   2460
ttcctggtcc cttcttcacc acgggctgag ttaggatgga aatgcagtaa gtgagcagct   2520
ctgacaaagc cagcctcccc tgcccaccag gcggcagaac agactcccaa gggaagggaa   2580
tctgtaaaca tcaggggagg ctgctactgg cgagggcttc tcaggaacaa attctgccag   2640
atgaacttga ttgcttttttt gatcaaatta caaagttggt ggtgcagcag cagatgtagt   2700
ctgtcctggg tggagggtga tgcctcatgg tctagaaatc ccaaaggccc ggtttgggca   2760
ggaactgcac tgcctccgaa ctgcactgcc tccgagtctg aggagcataa aggccaaggc   2820
cttggggcct cacttgcgag atcctcccaa gtacctgagg cttggagggt cagggcctgt   2880
ctttcacacc ttgaacctac actctctgaa cttcctattg ggtacttgcc aaactcacct   2940
catctgatag gtgtagaccc agcaatgtgt gaagtgctct gggaacaggt ctggtgagta   3000
cagaggtcag atctcggagg gctgcagggt gcagctgggg gacaaaggtt gtgaaactca   3060
gagaaaggaa ttagggctgg gcagtaggat gccataaata tatttggagc caggacacat   3120
gccctgggga agacatgggc tttggccaat aatgacacgg gtttctctgg gataagagac   3180
```

-continued

```
ataatagatg tcccaaatgc ttagagaagc tctacaattc cacgggcttc tgtcgtgttg    3240
gcagttgttc tgggacctgt ttagcagggc cgtgtccact ccctgactgg ggactctctc    3300
tccatccctc tggtagggca ctaattgctg actcccatcc agctccatct cttgctgttc    3360
gtgtacattg cctataaagt tggacttgtt tgttttcttt ctctctgggt accttgagtc    3420
tgaggatggt tgccatagag atatgtgggc agtcagatac cctggagtgg gggtggggggg    3480 gacaacaggg gctgggctct ctggcagaca tcctctggcc aaggatggaa ggtgcaggca    3540
ggaacaatgg cttgaggctg gatacctctc ttgcccacac agcagagccc tggtgcatca    3600
gaaacagggc tggcatctgg tgtctccagt tgatgatgca atgctttgct ctcttcatct    3660
caccagtgtc ctctgaccca tgggtaagag aaggagagat ggctgggagc cgaattctgg    3720
gatgtgagga taggtgatgt ggtgacttcc tgcagctgcc tgactggggc tttcatttcc    3780
tactccttcc ctacctgcgt aaatttccat gacctgtgtg atagcctccc tttcccttcc    3840
tcacctcctt ttaaccttgt cccatctttc ccaatggata tctttccctg gccaaactgg    3900
atgagacttg atttctcgtt gattttttt tttttcccct caagaagagg attcttgtgt    3960
aaaagtatat gcttcagaca gcaactcccc ctctcccaag atggatatgc caagactggg    4020
ctctgttgtg tggcctcatg tgccaggttg actttgggac agaggcacag atgataggca    4080
cagatgccag ccagagggt cagaatgtgt aagtgccagc cagtactgtg tggaggtggg    4140
aaagtggaaa gggctgtctc tggagatgga gggaacaagg tggggctgga ctataggtgt    4200
gggcatggga gatgtgaact cctggagaga tctgggccag ggtagccatg ggctggttcc    4260
catggggtta gggagtgagg gccatggctt ccctgcagac tctcagttta cactatatat    4320
tttataaagg tgcagccact ggagctgggt ttcactcatc gctgtctgcc taggtctccg    4380
caggtgttgg atttctgtgt ctgggaatgt cgtgggccca ccagggtcat ctgtgaaggt    4440
ctgaaggggc ttgctgtgtt cactgggtct tcctgcctcc tgtctttctt gtttgtgatt    4500
ctctgggcta caaactgaaa agataaaaag agggtataga gctgtttctc cttggcatcc    4560
ctggtgaggt ggctaggagt cagggagagg gatcacctgt tcttctgggg gggtccaatc    4620
gagacaggaa gccttctttt gggctgttgt gtcttgtcac tgtggcctca gaggcccaca    4680
ttggcggcta ggttgcaagg tggggagttc atgcggatat gcgttgagca ctgtctttgt    4740
ctgcgggcct gtctacataa agtcactgaa agtcacataa cgtcactccg tttgcttcag    4800
aaccgtgata ggagtggagc tgggctctta agggagccca tggttccaag cttagctcca    4860
ctaggccgaa ggaggcattt aaaataggct tggatgcagg agctagtggg ccaggtgatg    4920
gcaatgataa gtcgttattt taagatttaa gagcaccccc ctcaaggagc ctgagcccctt    4980 atgtcttttt ttatttttaa atcttcatat tcccttctta tctttattca tatgcataca    5040
gattttcacc tcgtggagca taacatttta tatcctgctc tctttgctta tatccaaagc    5100 atttcccca tattactaca gttgaagggc aaatggtcct ttcttctacg tcgtttagga    5160
tttatcccta aaacaatcag catcacaaga aacttctgta tatgtaccat ttatctggat    5220
tccagttgct tttaccaaga tagatactgg ggtaatgccc ttggccttac taagagatgc    5280
taccggaaac agtgttttga aatctgttat aatactttaa catatttatt taatctgtac    5340
attccgtgtg aagaaatttc ttttgaagct aaatgtaagc aaaagctttc ctctttgtga    5400
ggacctgaga ggtgagggaa gggtccttat gtgtttctat acttctgcat gggcaggccc    5460
tagcgaagtg cctgacgtat gccagccaca tacacattaa atgaatgggt caagaggact    5520
atgtaaccaa tcatggttgc cttttggctt tggctcctag gaaactcaga gtcaagttgc    5580
```

```
cagagccctt gtaccctgct acagacttgg gtcctccctt tctgatccag ggagccaagc    5640
tgcagacctg atacggctgc tggaagagag gacagatgag gataaagacc tgtgcttggg    5700
gcataaggca gagtgggaga tgtaggcaga catttagctg atgattcctc cttccctgtc    5760
actaaatggc actataggc cactgttggg atctcttcca ggtagtgatt ttcaatttta    5820
gtgtgcgtaa ggatcaccct gagtactagt ttaaaaaata cagacttctg ggctttagcc    5880
acagagattc tgctttagga ggtctagggt ggagctgcag aatctgcatt tttaacacat    5940
gctccagtga atttcatgca ggtgaggcat gagccactct ttaagagatg ccacctaaaa    6000
tctgcaacaa cagttgctct tgccatgccc tctggaattc aacagacaca ccttggccca    6060
tccttctcca gattgtgtgt ctgccactat gtggccatct gtgcacatgg gctgttctgt    6120 gattagggc ctcgttctgg gcctcgggat tgggtgtct gtgtctgagg ctgcggcaag    6180
ctgggtggct cggttgtgg catgttggcc accagaaggg taaaggctgt cccttctgg    6240 gtccagctgg ccctggggac tgaaatggga tcccctggat ggtgccagct gagagtcccc    6300
gcccccttag tgttggcctg agtagcccc atgacatttg tgtccctgt ggtatctcca    6360 agtgagactt tcctgttaag gatctgggtg aagtgaggga aagagaaggg aggggaagc    6420 agtaatgcag ggagtgggag aaggaagaga atccacaca gcactggaac acaggcctcg    6480
aggaagcatt taaggaggct gtgtgcgaaa ccatgctttc ctcctgagga taaaacaggc    6540
caatttctgt aaacagagaa atgggcatcc tgcatatcag tgatggagcg cctctacttt    6600
ctctcctgaa gggatggaag ccgactgcag gtccctctgt gcaaaggctt ctgccaggcg    6660
gcttttgtca cgcggtcacg ttgagctgtg ggccttagca cacacaacac tggcctgtcc    6720
ccctcccctc ccacctgtct tcctagagtg acttggggtg ctgcatcatg gtgtggggat    6780
ggaggtggga aggttccct gtcctgtcag ggaggcccct gccttcttcc tgctgcttcc    6840
tctggtccct tgtcaccata cccttgttcg aagctgtgct gaaaccctag aggtgagtgg    6900
ctgaccccat tctctgctga gactggagat agggaagggg aggctgggtg tgaccattcc    6960
tgctcccatc tgtatgcttg ctgctctctg aacagctttg gcagaccaac aagggcctga    7020
tcccatgggt gccaaaaggg tggtgacagg aggagatggg cactttgcac ctcttgaatg    7080
cctctctgca gagccccttt gtcacctacc catggccaga cagatctgcc gcaggaccgc    7140
tgggaaaatc aaagcacaaa agctttgtct ggggtctttt ttttcttttt tggttttgtg    7200
ctgcaggtgc ccatgacttt gccagggctc agacccagcg tcctcaggcc gtgtggcctc    7260
cacccactcc ttggcgcctt tctttaaaac acaggttctg gatactttgt tcctgtgatg    7320
aatcttggca tatcacctca cacctctcca tctaggcccc aagctccaag cctggtggag    7380
caaatccctc ctcgttgctg gctgaggccc cattcccgtc tgtacccacc tctctgggct    7440
gtgcggtggg gagatttcca gccactcctc cccaacacca tctccgcttc ctgggcccta    7500
tcagcagcag ccgcagcttc ccatctgctc ccctcttttc tcctccttt ctttcccttc    7560 cccctgctt gctgctgccc tgggaggagc tattttagg ggctgcttcc tgggatgttt    7620
tacttggggc tggttaccat gaaggaaatg tcaccaaaac agtgggcaaa ggctgcaggc    7680
accgggagcc ctgccggggg gcatggagaa cagacggctg acccttttct ggcccttgag    7740
agcagccaga gtgcccccag gcagagcctt gccttcttgg ggcttgctag tgacccctg    7800 gggattttct ctgtcaaagc tgattgaggg ccttttcgct ataggcatt tcttggagcc    7860 tctcgcttcc cttgccttga gatccagagg ccaaagtggg gctcaggtct ttgtgtcacc    7920
```

```
aagttaaaac tgcttgagtg agggttgaag ataaggggag gatgctgggt acatgcacag    7980
agccttgggg gttcacatgg gaccatttca ggccccgtcc ctctgtatca cagcccccag    8040
ctagtcacca ggtgtacatg tgtgagggca ttagaaacca tggtcctgct cttgtgtgtc    8100
ggatggactt tgcttttaat tggagactct ttgcatcttt agagtgagat tcaaagagga    8160
agggatgtgg catcacagtg tcaggtgagt gtcgtgggga tcgtggcttg ggattcccac    8220
tggtcagtgt cccaggccca gggctgtgca taagcagctg gggaaggtgg attatgacat    8280
caaatccctg cgatgtcctt gtttctgctc ctcagagtgc caaggggacc agacggcggc    8340
ctctgctgct tgggaagaag atgaaaggca ctcaggaggg cagcaagtga ggccgcctcc    8400
catggagccc tgaaatcagt ggggttgcag gaagtttctc acatccatgt ttagggtcat    8460
aggcacagac ctgcaaaata ccctttgcaa agttaagaat gtctttgaga ttggaacttg    8520
ggagagtcct cagtcagagt aggaatgtgc atcctttccc acgtacagag gattgtatgt    8580
ttacgtggca gcaggatctt atttgaagct agtgctggca tttgtgtttt ttttttagga    8640
aaatgtcact aagtcaagca ggcccatccc tgagagggcc atggagaatc tgtgccagc     8700 cctccctggc cccctgacct ggcagaggaa ggaaaggggca ttggagtagg cttctgtctt    8760
caggccagag ggggaggtgg ttcagggggca ggcttggtgc accccttggc tgcaagctat    8820
cacctcccta tctgcttcct cttttctgcc tcccctggtg catctggtca cttcttgctg    8880
cccttcctgt gaaatcgtgg caccttggac caagtcctga agcacttggg cagaaggcgg    8940
gagaggttgg gtttctagga tccttgtttc ccagggcctg gctctggcct gggctcagac    9000
cactctggtc taggcaggct gctggggaaa ggctggagct gcttctgctt tctgctcctg    9060
ttgccacctc tgctaatgat ggggaaaacc tgcagagggc tgtggttgga gctgggctga    9120
aggccggcag gggtgggtct ctccatggca gtagcacaca ggcaggcagg aagtggccct    9180
gtgcaaaagc gggaagtggc agttgtcaaa caggaagggg ggggctgggc tgtgggaggg    9240
gcggggatga gcctggtaga aaggtgcgtg gaggagggtc caccttggaa ggtctgagcc    9300
tctccctagt ggttactgga aggaggggtg tctcaagggg agacaccttt gcagcacctt    9360
gagatgccga gccagggccc tcccactgtg gaccaagccc attcagtggc ctcgcccttt    9420 ttgggggttgg agatgctgcg tccagctggg atgcccttgc ttttgggaaa gatgctctag    9480
aaaccactac tccatcctgg aaccctctg ctgccactgc tgctgggatg gaccctctgc     9540 tttttttgcag ccgtgggcca gccctggatg tgactacagg acaggaagtg tcaggggaag   9600
agacaggaga caacagctgg agaggctggg tggtggccgg gcagtatgtg gcagcaggaa    9660
cggggagagc ggggcaggta gaaactgctc tgttcattga ggagagcttg tggatggcag    9720
ggtgccacgg ctgcgaggaa gaggagggaa gcggacagtg gcacttcctg cggcgttccc    9780
ctctctctga ggagcccctg ttgctgccca tcacctgcag actgtagaca caggtgggcc    9840
ccgccaaaac agggagggac actccacctc caggactgca atggaggacc atgtggggag    9900
cccagaagcc aggcaggagg gcttagttgc tgtgttgcag accctgcatc tgcctgggct    9960 gagggggacag tgggtcccat tcacagtgtc tctggtgata gctgtggcca caagcccagc    10020
ccaggagacc ctgtcaagct ctcactgggg cccttggaaa ggagctatat gccagacctt    10080
atgcaaaact cttgacctgt accacctcag ttaaacctca gatcttgctg tctctatttt    10140
agaagtgagg aacctcttgg ccgggtgccg tggctcacgc ctgtaatccc agcactttgg    10200
gaggccgagg caggaggatc ataaggtcag gagatcgaga ccatcctggc taacacagtg    10260 aaacccccgtc tctactgaaa aatacaaaaa aattagccgg gcatggtgat gggcgcctgc    10320
```

```
agtcccagct actcgggagg ctgaggcagg agaagggcgt gaacctggga ggcggagctt   10380
gcagtgagcc gagatcatgc cactgcactc cagcctgggc aacagagtaa gactccatct   10440
caaaaaaaag caaaaaaaac aaacaaaaga agtgaggaac ctctttccca agataatgtg   10500
cctggctcac tgtctcacct actttgggtc ctaatcaaat gtcacctcct tactgaggct   10560
ttcttggact gccctactca aatctgcact ccccactttc tctgcttttt ctacgcagca   10620
cttgccgtga catctaacgt gctgttgagt tttcttactg tccatccctc ccccatacac   10680
aacccactag agtgtcagct ccatgagggc agggattttt gtctgttttg ttcgccactg   10740
tcttcctagc atcttgaata ctgtctgtca catagtaggc ctcagtaaat atttcttttt   10800
ttttttttgac ttgctctgtc accccaagct ggagtgtagt ggcccaatct ggctcactg   10860
cagcctccac ctcctgggtt ctagtgagca catttggcta aattttgtat tttagtaga   10920
gatggggttt tgccatgttg gccaggctgg tcttgaactc ctgacctcaa gtgatccacc   10980
caccttggcc tcccaaagta ctggactggg attacaggcg tgacccaccg cgcccagcca   11040
cgataaatat ttcttgaagg aatgaatgaa gctcgggtgg gtttaatagc ttgctggatg   11100
tggcagtgtt gggctcaatc cagggctgtc tgacttcaaa accgatgtgt tgttaattgc   11160
catactccac agcttagaat cagaatgagg atcaaggtat agtcctgggg ttcagagaag   11220
acctgggcct tgccgggaac acagggctca gctccttgga gttaaggctg aactaagagg   11280
ctaacaagga ccctctggat gctgggcagc tcctttgagg agctgggagc ctgagtctgt   11340
gtatcttctc tccactcaaa gtcactggta aagcagagtg cccttatttt tagtgctgtt   11400
gctgttgtgg gactgtaacc attagctagt aagagactta aggaaggaga taaacattaa   11460
tcttctgggc cttccctcag ctgccacctc cgcattgcaa gatgctgttc tcctgcacct   11520
gcccaggcaa ccaagcctga gagttatggg ctggagggtg gtgaggtttg tgcccagaga   11580
gagggccgtg ggtctgtagc tttggggctg gctggcttgg tacctccatc tcaagtccag   11640
ggatggaagg aagtggggt catgtcaaca tcctgccaga tctggaagaa gcaagccccc   11700
cagccaccag gcaaggctgt tacagcctcc ttgagtgcct cgcttctgga ggtcactggc   11760
cacatccctg tgcctgggac caagggatgc caggtgatct gggagttggg agttacttgg   11820
ggttctcctg gctgcatcct ggtcggtggt catgctgaac ccaggcacag gaaggaaggc   11880
ctgacccaga tctttgggca gctgggacgg attagctggg cagcaggaac taatctctgt   11940
ctgtccccac ctctttccac aaagtagagc tgttgctaga gggaaagttt aggacaaagc   12000
tgggtttggt tagtgaaaca ataaatgtga atttcttcta gtccataatc cctacattat   12060
ctcacactga cagtcctgag tttgaatccc cttttatcc ctttcctgct gtgggatctt   12120
gggcaagtta cttaacttcc ctgggcctcc gtttcttcca tcatctggaa atgtggacaa   12180
tcatagcatt tacctaatgg gatcattgtg agggctgtgg gaagatttac agaagctttt   12240
tgctgtttag ggtagaggca gggagacagg aatagcttgg cagctatgga tgtgaaggcc   12300
cctgcccggg cctggataat tcagggtgaa ctggactctc ttccttttgc accccctcca   12360
aagcctagag tcttaactca actctcacca ttctttatct ggccataata gcacagggt   12420
ggagaaagag ggctctaggc tcagaccacc tgcatcactg cctgttcgtg ttaccttagg   12480
cagattactc tatctttta aacctgtttc ctcggtaata taatagagct aatcagatcc   12540
ctacttcaca gagtttctgt aggtatgaaa tatggtaatc catgcctctg cctgacatgt   12600
agtcagtgca tagtaagcga ttgttatggc gactactgtt attagtaaac ccttattaag   12660
```

-continued

```
cccctgttta cagaaagaac tctagaaagc actacctgga aagtaccccc cgccttcgaa    12720
gagcttgcaa ctgaaagata actgatgtaa tatatgatgt gagaatcgtg agaagtgcat    12780
tgggaaatcg ggggggggg gtggagtag agggagaag tcacagtcta ccgagaggag       12840
cagggaagac ttcatgaagg aggtgacttt tggcaggatt tcagcaagta gaaagaggga    12900
aggacagtgg gggagggctg tgaggcctcc gtgctgtgag tagcatcctc tcttcccacg    12960
tactggagct ctgccttcct gtggaaggaa ttgacccacg cagctcactt ggatctgggg    13020
acttgtggat ttctggttat tccaccaaaa ccaagtaatc ctggagtctg aatttgaaga    13080
ggtcaaagct tacagccatg gtggccaaga ggactccggg gagaagcagg atttgtgtcc    13140
tggtttctct ttctataaaa tgggcatcat actaatgcca cctcctagat tgttatgagg    13200
ataaattaaa agaggcagct gcctggtgta gaagtaagct ctcaataaat gttagctatt    13260
attattttaa gtcatcatta tcttgatcat caacctcttt attatcagca tcattatgtt    13320
tcaggcttgc catcaggact atgtagagaa tatatgcaaa accctagcc agtgccgagt     13380
atatattagg tgctcagtat aacttagcta ttattagtgt tcctaacaag aaagagattc    13440
tgggccaggc gcggtggctc acgcctataa tcccagcatt ttgggaggcc gaggcgggtg    13500
gatcacctga ggtcaggagt tcgagaccaa cctggccaac gtggtgaaac cccgtctcta    13560
ctaaaaatac aaaaattagc caggcgtggt ggtgtgtgcc tgtaatccca gctactcggg    13620
aggctgaggc aggagaattg cttgaaccca ggaggcgaag gttgcagtga gctgagatca    13680
caccactgca ccccagcctg gcaacagaa cgagactccg tctcagaaag aaaaaaagag     13740
attctggaca ccctggacca ctgaaaccct gttgtggtgg aaagagcacc agagttttag    13800
ttgaataccet ggattcaaat cccagctctg ctgctcactg gctcgaagtg tgcaaaccct   13860
caagtcattt cctcatctgg aaaaggtggt cataactatc tatctggccc aggcctggtg    13920
gctggtgcct atagttccag ctattcagga ggctgaggtg ggaggattgc ttgagcccag    13980
gagtttgagg ctgcgatcat gccactgcac tcctgcctga gggacaaagt gagaccctaa    14040
aatgaaagga aaacaagttg tctccaggat tgccatgact tgctgcatta cttcagcaga    14100
tcatcacaaa tgcatagtta gtacctgaac tgaaggaata tgaataacaa ggtgaccaca    14160
aggagaatgg atggttgatg gcttttgttt tttctcttct gcttttagat caccagaaac    14220
tagaacgtga ggctcggata tgtcgacttc tgaaacatcc aaacatcggt gagtgcctgg    14280
gcatggagca ttttgtgggt attttgtaga agcagggata acagatatcc actgcttttg    14340
tgtgtgggat cacctctgtc tgtggacctt cacctggtgt ctgttttac atgagcagga    14400
tagcaactgt gtctcagaat tctggggcat tctagtttag agacctgagt atctgcatca    14460
ctgcggcacc ttctcagggc tggggtgtga ggcatcagaa taggtttcag atgctatttc    14520
ttcccttttct ccttctgtct ttgggctgag gtccagggtc ctcagcgtgt gaggttccgg   14580
gctcctagcc tgccagcgtc cctcaccagg ggccatccac agccctcatg caagggtcag    14640
gattttgttt gtggacctga aagagttttg ttcctgctgc ggtgtcctgc acactctggg    14700
ggtttccatg gtgctcccat ttgtattccc cagagccagg aaagcaagct gccccctgc    14760
ctggctcctc tggcagaagg gatggcagga accactcagt atgggaagg agaaaaaaga   14820
ggatttctcc ctgctcccac cctgactggg gggacaagag cacattgttg gttgtgctaa    14880
agcctgagga ggtttgcctg cctcaaccca ctctggctca gttttacttt gttcagctga    14940
aatggtcttt gccaaaagcg ttggccctga tttggtgctc cttgcagaag ggacagaaac    15000
tgggctggct gcagtgtctg agcagaagcc ccagtgttga cttgaggcag agcaaggagc    15060
```

-continued

```
atctcctagg ttttccctga aagccctgag tcatcacaaa agacaacacg tgttctgtgc    15120
tcctcaggca tggcctaaat ctcagggctc ccaccgtgcc ccagaggtcg cctgctctgc    15180
tctgttggcg gccagggctg tgaggtgact tgctgaagcc taatgcttcc ttcagagcta    15240
cccagcccct ggcttccag gtctcgggct agaacagtca aagtgagctc tgtcatggaa     15300
gggctgaggt cctgctctag ccctctggga gaggagcagc tctgaggtag tcagaacgtc    15360
agctgtgcag ggctttctag atggcaatca gcagcttgga ttacacccga agcagattgg    15420
tgtggccagt ggtgatcggc tttgcctgat gcagtgtgtt ctgcagagcc agcacctctc    15480
agctggtggg ttcctggccg cagaactact ggagctccta ggtggtttct gaggttaggc    15540
cttcacctga aaacagcgca gtggggactg acatgttgcc tttggtagga gagggcccac    15600
agagggaaac acctagaaca gcagtcacag attaggcatg ttttgcttgg ctgactcagt    15660
ggtctaaaaa tattttatt atttgccaat atttaaaaat gagatttcac attttgaaaa      15720
aagaaaaaat ctattccccc gcctttccag tcagaaggct tggctctgct gagccccac     15780 cttgcatggc cagaaggagc tgtgaggagc ggtggctgcc cctgcagccc gctggccact    15840
gtccttgtca cccactatga gctcacattt gcattaccca cctgggcccc tgtaggcctt    15900
gcaagcttgt gacctctaac ctagaagttc cagaacagga agaaaaaaca tgtgcgtgac    15960
taaagccacc cataagcaca gaagcatttt gatgttccag acccgggtct caatatctga    16020
ggagggtaac ttccttttcct ttatgctcct tgtgaccaac tggtacagca gtgataattt   16080
gtcctcatgt aggcaggaga acagcagcta gggtcagtg atgcaggaag cagaaccatg     16140
tccacatcac ccgcgatgcg ggcgggttga ccatgggcgg gttgaccacg gatggggttgg   16200 ccacggacgg gtcagggtat aatgaagaca attgagaaat gagcaggaag gacaaaaata   16260
gaattctagg tgaaaaaagc cctaggtgtc tttttattta tttctagaat taaatacata    16320
cttttttacc ccatagactt cactctgttt ggtagcccctt tacttttacc atctgccctc   16380
ggctcagaat ggaggcaggc ggagggacca tatatcctgg ccgtctgctc agaggccagg    16440
tggggcacag tcactctttt ggcctctgat ttcctagaac tgtgcttcca tttcatgact    16500
gctcccaggt cctaaggagg ttggtccgag gaccgattct ggggttgagg gtgggcagag    16560
ggaaggggga gtcaagactg tgtcctggga gctccagcat ccggtgggaa ccagggctgt    16620
tggagatgtg gcggagctgc aggtccaggc ggctgtggtt gccatggatc tggacctggc    16680
ttgtggcagg agaggaggca attttgtgcc cctaattcac tattcctctt ctctctccac    16740
tgcgctgtcc ttcagaactg tgacccttttt ggctctggcc tcttgaactc catcccaaag   16800
ggaaacaaac gggccagccc aagaacagtg cacagtcgag gaagctagag caaagagcat    16860
gtggtcagcc ctgcctgtgg tcagactcgg aggcactgaa ttcagatgga gcatttggtg    16920
ctaggggcca gtcatgccca gtttccccctt aatagctagt atattctgtc ccaggagtta   16980
aaagcctgtt ggaagagtga accctgatat aaactctgga ctttgggtaa tgatgatgag    17040
tcaatgtggg ttcatagacg gtaacaaatc caccactcta gtgggagatg ttgatggtgg    17100
aggagactgt gcatgtgggg gacgtgggt atttgggaat gttctcgggt atttgggaac     17160
accctgtact ttccgctcaa ttttggtgtg aacctaaaac tgctctgaaa ataaagttta    17220
ttaattaaaa acaaacaaac aaacaacaaa atgcctgttt gggtgtaagg cacactgccg    17280
aactccaaac agcgctggga gtgtggccag tggtggggag ttgagaggag gagacgctgg    17340
tgtgaggtct gaggtctgaa tgaagtccgt tctacctgtg atctgcctgc tccctgctct    17400
```

```
caagtcctct aatgaataga ctctgtcttc cttcgtgctg agctgcccca gcagtttcga   17460
tcatagtcta gcattgtggt ttagagcagc acttctcaaa cttttatgtg cttaagactc   17520
acgcagggat catgttaaaa ttcagattct gattcagggg gtctggggta ggacctgagt   17580
ctccagctga tgctcatgct actggtccgc atgcctgtca atacttggag aagccaagtt   17640
ttgcggcttc ggagtcgcat ccagatttgg ggtttgaatc tgggatttgc taattagtaa   17700
ctgtgacctc tggcaagtta tttaactcct ctatgcctgc ctctgttttg ttatctgggt   17760
cccttcgtgg agttgttatg aaagggttca gccaggaaag ggggctagga gggagatgat   17820
gaaaatggag attccagccc ctagaagtga tctcttcaag acccccagcc tcgactcagt   17880
tcacaagtta ttcaagcctg accatttacc cttgagccca gtaccattc agctaacagt    17940 aagtgtagca aagaaacggt tgcaaataaa agaaacatt gaatcatgac tgagcagttc     18000
ctacatccct gcccccatgg tgggggtggg gggagccctg ccacagtaag ctcttggggg   18060
gcagctcagt cccccacaag cccccatggc aacaggacct ccttcccact gtgttattgc   18120
tgcagatatt tttaacagca acacttttttc agtgcttttt ggagaaagat ttgttagtta  18180
aaatgtggca tattgttggg tggtttttaa agaattggaa atagccacaa catttgggtt   18240
gtggctatct cagtccttga agacatgaaa tatcaagtaa aggtttgtag gtgttttggc   18300
ctgttctgtc ttccacggtt tttaaagaac agcaattagg tttgttgctg aaatgcagta   18360
aatgctttat actcctttcc ccagatcttc ctgtctatgg acatggcctg gcccttgttg   18420
gccttcatgc cctgtcttta ctctggaatg ggctgggtgt cagattattt tattccacgc   18480
atccatagtc cctctgctcc tgcctcacag catgacacag ttgtgcttag ttaacgcatt   18540
tgtgtaattg ctggttttaaa gcctgtcttc cctcttcgcc tggcagctcc aggtggcagg  18600
gccggctcct cttcttcaca gccacatcca tggcatgtac agcctcgcct gctccggggt   18660
agctgcccag tggacattgt cgagccagtc agaatggcca caggtagtgg ggacagattg   18720
gagctccttt gcctaagaat ttgagaaggt gactcccaag caactctgca atatcaggaa   18780
tcttgatgtt ggtttgtctt ggcttcaagt cccggttctg ccacttagtg tgattttggg   18840
caggtttctt atggagcctc agtttcctct cctgtcagat ggggttattt atatgtaagt   18900
agctaccctg cagagctggt gtgagggttc aatacagtaa tgcacgtgga gcccatggaa   18960
cgatgccggc acacggacag ctcaactaag tgttagttgt tagatttaga ttgttattat   19020
cagaatctga tgggtgcgg tggctcacag ctgtggtccc agcctctcag gaggctgaga    19080
caggagatgg ctcaagacca ggatctccag cccagcctgg gcaacatagt gagaccctgt   19140
ctcttaaaaa aaaaagaaa taatgaatct gctgttgcta aataggcact tagaatggca    19200
cagtcatttc tcctcttgtc ttcagtgtcc tgttaatttc tttacaaatt aaaaaaatgt   19260
cgatagcagt cttattcaga tacagcttcc tccatccctc cttgtcttgg caggtgcctt   19320
gctctggggc acacatcaaa gctgttctct ctgctgggtg gcctagaagg attagtcttc   19380 cttttgctgct ccttttcttct aattcccttc cccggcttcc tcccacctgg gctctgtgtg  19440
tggccttcct ggagaagggc agacgccaat gactccatgt ctaggcagag gcctgggtgc   19500
ctgcacttct tgcctgttc ttggccttgc tgtgctgggc gggggcaggg tggtgtgggg    19560
catggggtgg tgttgggcat ggggtgggt tctggctgag gcagggctca gtgccaggcc    19620
caggcagagc tgagtggctc cacttctctg agatggttgt cagcatcata cctgctgctg   19680
tcccgttaat tccccatgct gctgctgtta gtcacctccc taatgagct ggtctgtagc    19740 ttctgggaca gctgatttcc agggattat ttgtattaca cactttaatg cttttaata     19800
```

-continued

```
gcaaattttt aattaaatgg aaagtccttt tggaagcgag ggagcagcag ctgcagcaag   19860
actcagcgtg aggcaccgac ttagaccaga ggtgcgcaag tgagtgggc  ggaggcaatg   19920 gcaggacttc gagaggactt gattgagtgt atatggagtg tgcccaggct aatttttatg   19980
ggaggaaggc aggggcctgg cgctggctcc ttcctcctgt cctaaaagcc ccctctgtca   20040
tctgcaggcc tagggaagca tcttctttgc ccaggagaga atgtatattg gatatataca   20100
ttatatccaa taatgggagg gatattggaa gtatcacctg cctttgatcc cgttcccaga   20160
aatactgaga ttgggatggg attttgggg  ttgagtcact agattagatc aaatagtgta   20220
ggtaatggga tgcggaaaca gtcttgaggc cctggctccg gccctggcag gcttcggagt   20280
cctcagtcat caagggagga gaacaagggg gctatagtgg tggttcagtg cctcgggact   20340
gtgccggctg ggttgtatac tttgctttct gaatgatctt gcttcgtggg gagggacat    20400 agggaagcac ctcagccctg aggaaacgtg tgacactgga aatggaagca gccagggccc   20460
acccaggaag agacatggcc atttctttgt ctcctagcac tgaactggtt agtttggtgt   20520
caggccattc ctgaagtgct ccatgaggtg cacctgtaac tgccaaggct tggagcaaag   20580
gtcaaaccga gggaggcctt tggaacagaa gttccccatc aagagagttc acgtgagggg   20640
agggacagga cagtcagcca aagcggagtc gtttctgcat tagaatgatg ctcagggtt    20700 ggcatttaac ccagaggtgg ctttgtgggc agaaacttga agaggagacc tcagaagact   20760
tcaggttggt ttttcccca  agagctttgg aggcggggag cagggaggga ttccgcctgc   20820 cagcttttc  tcgcagctgg tgcatcgccc gagtcttctt ccagtggcac cctcccggac   20880
ctgtctgcga tgctgcttta gggacatttg taagtggtct ttcttttgga tgccagggct   20940
ttgttgcctg aatatggggg ctgccccaca tttcttaagg gaagcagtgg tgtagaccac   21000
agtctttgga gtcaggtagc actggattca catcttgacc caccacttag aagctctttg   21060 gccttttgtta agagactttg tgtccctgag cctctggtgc cctcatctgt agaatgggaa   21120
taacattcat ctcaggtggt cgaaaggaat aataaactcc tcaaaggcag gcactctgtc   21180
tgttcctcct gaatcccgct gcctagcgtg gggtccagca catagtaggt gcttgataaa   21240
tgcttgcaga atcagtaatg tatgcaagag cctagcacaa ggcctggcat agtaagcact   21300
taataagctg ttattgttgt cattgcctga atgtgtgcgt ggccttccag gctcaccatc   21360
cattatcctg caccacgtgc cttcctgctg agctctgcct ttccaccttc ttccccaccc   21420
cttagttctg ctcccattta ctgctctgga agagctctct ggctttccca tctggtcatt   21480 gttgtccct  gccgtcaaca ttgctaggtg ctgctcacgc tgcatctcac catcgtgcat   21540
catatcccag gaccaccttc tcggagacca gccctctggg aaggttccgg cttttctcca   21600
tcttgacttc ttagccatga agcttttctc tcttgcctga gtctgaggtg caaccagag    21660 cgccaggctc tggctcccag gctgcatagc cttgcactgg ggggcactgg gcacgtcgcc   21720
acttcccccc actgctcctt ctggagagcc ctgtgagccc gacaggatgg ggcagggtg    21780 gggctgctga ggagaagcct aggatttcca agttttctct ctgttaatct ctgtccccat   21840
ctcctctctt gcagtgcgcc tccatgacag tatttctgaa gaagggtttc actacctcgt   21900
gtttgacctg taagtgccac tttctgaggg tgtgggggcc tttccctcta gctgactcaa   21960
aatgaaggct caggaagggg cctaaacagg ctctccagcc tccgcccagg gcccctcct    22020 ttgtccgagg gaaaggattt gactgggca  gattgctgcc cccaccaagg gggtctccat   22080
gttcccccag cgtccccca  gggctctgaa ccccaggaca gcattcctct cgcacttctg   22140
```

```
ttcagcagca cgccttgcac agatgccttt gtcttgtttc tcagtgtgct gtccttagtg    22200
aagaaataaa agacagctct ttgcatgacc ttaaaaatcc tgagaaatca gaggtagctt    22260
tcattagtcg gaaaccaggc tccattggat tgggtctctc ctccacgttg gttgtggttt    22320
aatgtcttaa aagtggctct tacctcctgg acactcctct ccaggattct cagggttggg    22380
tctctgtgtc attggtctca ttactcttca acttcagtag tagctctgtc cttcctgggc    22440
agcgatattt tagtgtttat gttggtctca aagctgtgac ttttggggta ggttgactgt    22500
tttctcttag atccctgtat cttcatctct gcctgactat tagtgaatct gtgcattttg    22560 gaaaagaaa tgtccggaag aagggacgg cccatgatac ctcaaggaga atccgggtgt      22620
cactgaagga tcgagtgtgt tctgagctct cagatgaaat gcatgggag ttgggatttc     22680 tctgaaagcc attctacagg gtgaccctgt ttcttcttgg acattggggt tggacaaagg    22740 acctttctg cctctgaccc tcttcttccc gttggttgca gtgttaccgg cggggagctg     22800
tttgaagaca ttgtggccag agagtactac agtgaagcag atgccaggta ggatgagggc    22860
ccgagagttc aaatgtagct ctggagttta ggactgaagg aagtcttggc caccttcggg    22920
gtccagcatt gtacctgttt gaatagtctt tggggaagat cagaatagct cttgtctgga    22980
gaaagattct gttgagctgg gctagggctt gcatactgtg ggtgatatta gaagttaaaa    23040
attcagcact tcctaaccag cgcagtggc tcatgcctgt aatcccagca ctttgggagg     23100
ctgaggcagt tggatcacct gaggtcagaa gttgagccc agcctggcca acatagtgaa     23160
accctgtctc tactaaaaat acaaaaaat tagccgggtg tggtggtgtg tgcctgtaat     23220
cccagctact taggcggctg aggcaggaga atcacttaaa cctgtaagcg aaggttgcag    23280
tgagccaaga tcatgccact gcactccagc ctgcgtaaca gagcgagact atgtccccct    23340 ccccccccc cacaaaaaaa atcacttcca aatgaatgtt ttacaaagct tttccaagtc     23400
tcctttaccc tgtgacccca gaaatacttt tttttttgcac taccatgtac tcgccaccat    23460
gcccaatgtc cccctctgcc cttttctttc ctttgacaaa ttctggtgtg ctcaagccac    23520
tgtgctgagc ctctggcatg atccagaggt gcagaagaca tggtttctgt cctgaggag     23580 tggagagttc tgggctgata atccaaccat agagccccgg gagctttcag cctctgtcac    23640
cttgtcccta gaccaccatg accagccttg ccgtgggggct cctccaactt gaggaccgtt    23700
ccccggccac atgcctcagc ctctgccctc cctggaatcc ctggtgcctc cctcacccac    23760
gctctcaggt gcctgttcag cctgcctttc ccgccttggc tcttccccca gccttgcttt    23820
tctcgagggt gatgtcccta caacctggtt ttgatcatcc tgcctgcagc ttatctggct    23880
tatgtggcag ctctggctgc ttctggagag tggggagtg cagcttcctc acgaatttct     23940
caaccttgag aggccaatgt ttgctgatca acttcagatg cttcagcctc gggaagaatt    24000
ctcaagtggg gagatgaatt ccagtgccag caggggagga cgaggctctg ggacggagga    24060
ggcagtgatg gctcagggag cctgcgggga ggagggagag ctatagggag ggggccctga    24120
gggggggtga ctgtaccagt gggcttggcc tggctctgct gggacacttc gcacttttgc    24180 cattttggc cagaaggcgc tccctgctag cccggctctg ttctaattat acatctctgt     24240
ggagactcgc ctctatagct cagtcttaaa gtttctgtgg cccactcttg ggctgtgtcc    24300
tatggggagg cccgagtttc agcccccagg gacccagtac gacccctggg ttcttgtggc    24360
atccccagca tcagattta ggaatagtaa gtccaggcca cccagcccca tacactggga     24420
tgctctgcag atgtgcttaa tataccagat agtgcctgat gacgggggtc tatattctag    24480
gccaagttcc tcagccttgg tgctactaac gttttaggcc aggtacttcc ttgttgtgag    24540
```

```
gcctctcctg tgcattgtgg cagacattta gaagcatcct tggcctctgc ccaccaaatg    24600
ctgggagcac ccctcctcca gttgtgacaa ccagaaattt ctctaggcat tgccaaatgt    24660
cccctgcggt ggggggggc gggcggcaaa ttcattccca gttgaaaacc actgctctag     24720 actgccccg ctccctgtca ggagtttgat gacagggatg gcaggatggt ttgctatgtg     24780
gacagtctga tttacgtgtg tgactgtggc tgggcgcagt ggctcacgcc tgtaatccca    24840
acactgagag gccaaggtgg gtggatcact tgagctcagg agttcaagac cagcctgggc    24900
aacatggtga gaccttgtct ccacaaaaaa atacaaaaat tagctgggca cggtggctca    24960
tgcttgtggt cccagctact ggggaggctg aagtgggagg attgcttgag cccaggaggt    25020
caaggctgcg gtgagctgtg ttcacgacat tgcactctaa cccaggcaac agagtgagac    25080
cctgtctcaa aaataaaata ataaaataac tttgggtttt tttctctacg caaaatcatc    25140
agaagtgctc cttaaatgcc ctgtttggaa gctcttaagt acattgtttc ttaaaggtat    25200
ctttgtactt gttttagctg ccttactgga tgccagacct cagggcagct attgggtctt    25260
gtccatcttc attatcctag gcactcaata aacatttagg gaaatgaatg agtgcaccca    25320
ccgccaaagt agcttaggtt gtttagttgg actctccttc ctaagttgcc agcacaagct    25380
tcttctccaa gaacaaagtt actgtatgga gaaagagaaa gaaggaaggg attggatgct    25440
ctcttcttcc tcaggattct gggctgtctc ctgatctctt ggaaatgagt tggttgtgtt    25500
agacctttcc agtcaaaagg gggtgagagg aacccgttct agcggtgatc ctagaaaaac    25560
cattgcatct gcctgggcct cggtttcctc tttctttaaa taggttgaac aagatgatgt    25620
gcagagtcta aggttccagt ggccgttaag tgattctctg tgaatccgtg gccccttgtc    25680
acatgcctta gtctgcagca tgtggttgtg gatgtggatg aggtggttta accctgcgct    25740
aacatttctt ttccttctgc ttttttagcc actgtataca tcagattctg gagagtgtta    25800
accacatcca ccagcatgac atcgtccaca gggacctgaa ggtactaccc aggctcccct    25860
ccgtgcctct gctcatgaag tgttggcgcc acctggtgcc agatagtggt actgcgtagg    25920
cccaaactag gcttcctctg ggctgcaggg tgggtgctca caaggttctc tgtgtttctt    25980
ctgcagcctg agaacctgct gctggcgagt aaatgcaagg gtgccgccgt caagctggct    26040
gattttggcc tagccatcga agtacaggga gagcagcagg cttggtttgg taagggtgat    26100
cctgtcttcc cggaatgcag cccccgccct tcctcctctt cctgatctgc cttcctctat    26160
tagaactaga agccagaccc ttaatggtcc tggcctccga gatctctctt ggccgtacgc    26220
gactcagtac agtaagtcta gctgttgtca gcactgcttt cttgctgcct gtgggaagga    26280
gctggagttc ctggtaggca tacggctttg ccgtctggtt cagattccag cgctacaag    26340 aagcccagcc tgtcagctct tgctgcccat gtgctgagag tttatgtagc aaaagcagca    26400
ggaataagat gggacttggg ggaaatggct ggtgtggatt taacgagaga gaagtgggt    26460 tcagtatgcc tctgccctct cttttgctac aggttttgct ggcaccccag gttacttgtc    26520
ccctgaggtc ttgaggaaag atccctatgg aaaacctgtg gatatctggg cctgcggtaa    26580
gcccattcca cgctctcagc ttttcgctgt taagggccct caacttccga tgatggcaag    26640
aaagaggcat cgctattcct tgcaggtcac acacgtgcct ggtgtatgtg aaattatggt    26700
gtttgcccct gggatggctg ttcccatcac accctcctcc ctgcgtactt ctgggatgac    26760
attgtatcct tcttggagag ggatttgccc acgccttaga ggatggttg tgcctaaaga    26820 aatccctggt gtgacttggt gacgtgaagt gtgaggcata gcaggagggg ctggtagcat    26880
```

```
agcattatcg gctggcatcc acttctgact ctggtatggc ccctgccttt ctaggtggct    26940
ctgagccctg catggttttt cttggttcct cagggaagta ggcgactgac ccccatgacc    27000
tgtgtgttct gtctcgtagg ggtcatcctg tatatcctcc tggtgggcta tcctcccttc    27060
tgggatgagg atcagcacaa gctgtatcag cagatcaagg ctggagccta tgatgtaagg    27120
accagagagc cggcagcca ggccaggaag ggcagatgtc ctgctcctcg ggctctgtcc     27180
aagggagcag gcttgtttag tgtgtcacgt gatacggggg tgtcagggga ctttgaggac    27240
ccaggaatgg gcatccaggg cccaattctt gccactctat gtcccaggga gcaactttct    27300
tttgcacagc cttcttcata actaaaattg aggagtccac tgaagtcctt tgatctttac    27360
ttgcaaagaa tggagcggcc tcattggtgt gctgtgtaac acaggacaa aaggcctgga    27420 gactccctcc actgcagtgg caccttggac acattgctga gcctctgttc cctcctaagt    27480
atagagctgg gcttaaacca gagaatgttg gagtcccctt cccgctctaa tctgatgttc    27540
tggcattcta aacatgactg ttctgtctgt ctttccaagt ctttaagttg acacaggttc    27600
tggaatagcc gcagggcttc tccaactctg ccagtcacag cttaggtac cacagagtat     27660 cccaattaca ggagttgagt tgaagacaga accagtgttg cagggtatga agctcaccaa    27720
taccacattc ttctccctat tcctgctcct tagttcccat caccagaatg ggacacggta    27780
actcctgaag ccaagaactt gatcaaccag atgctgacca taaacccagc aaagcgcatc    27840
acggctgacc aggctctcaa gcacccgtgg gtctgtgtaa gtgtctttgc tagtggccaa    27900
ggagctcagg ggtgtcagcc ttctgtgtgc cctcggcacc accccctcct tcttaccagc    27960
agagattcat tctgggcccc aagcaataac tgagcaggcg ggcagaggac tgttgagggc    28020
cagggtcaat aaatgtcacc agggagactc gggaggctga tggggctggt gggccactgc    28080
tcctctctcc cccactcatg gctgtcaggc tgggattggt tctgttcttg gatgagggct    28140
caggttgacc cttgtggact ccaggtagcc ggtgatagaa agcagctggc aaaacccaaa    28200
gtgaattccc aagctggggt tcatactcag atctcaactc cactggagtg gtgaccaaga    28260
tccaacaaat caacagaagg ggtttctgag tcattaaaag cataaaagct gaggcataaa    28320
gcttctgcgc taaagtccta ggagagtcct ctaggctatc agtgtgggtt gacgtactct    28380
gtttttatac acaattcttt caagctgaaa tatcaacttt cagacaaaga agaggatttg    28440
gtagagttag gcatcttgac aaccacgagg cattatttat ctgtccattc tgtgtttatt    28500
aaatacctct ttggtgctgg ttaccgtctg ggtgctggag atacaaagat gaatgaggca    28560
tggtccctgc cccaaaagat catctaggga gacaggcact caaacaggca gtcatgttac    28620
aatgtgacaa gtaggtacaa gaatctaatg agagtacagg agctcctact gttcctggtg    28680
ggtggtgggg ttactgaagg ctgcacggag gaggtgacac ccctgtgctt gttcttggca    28740
aataacgagg tcctcagaac gttaacctgc agacagagtt tagcacagtg agaggttatg    28800
ggaaactatg gtgagttgaa ggaatgttga gttgtttggt tgtcgatgag gctgcaaata    28860
tcagaatgca agagaatggg gcaaaagatt ccctgacata caagtttctg cctcaggagt    28920
ttggatttta ttctgaaaac atagggaatc atttaagggt tttaaagaag aatgaaattt    28980
gcatttaaga acactttgga agttgtgagg aaatgaattg ccaggcatgg tggcatgtgc    29040
ctgtagtctc agctgctggg gatgctgagg caggaggatc ataagcccag gagtttgagg    29100
ctgcagcgag ctatgattgc acctgtgaat agtcattgta ctccagcctg ggaaagatgg    29160
tcagacccca cctctttaaa aaaaaaaaa aaaaagaag ggaattgaaa atttttaaaa    29220
gaaaagggct ggagacagag agctcaggaa gcttttttaa tagttggaat agtctaagca    29280
```

```
agaccaggtg aggtctcagc agagggtaag gatgggggaa tgtgcagtgt gttgaaattc    29340
aagagatatt tgagagaacc taaaggattt aattctctcc agttggattt gggggggagca   29400 aagaagagag aggccaggtt tcaagttgag cggagagttg taccctcact gacccagaag    29460
aaaaccagag gaggagcttg tttgtgagac aagacgatgg ttttctcttt ttttttttttt   29520 ttttgagatg gagtctcgct ctgtcgccca ggctggagtg cagtggcgcg gtctcactgc    29580
aagctctgcc tcccgggttc atgccattct cctgcctcag cctcccgagt agctgggact    29640
acaggtgccc gccaccacgc ccggctaatt ttttgtattt ttagtagaga tggggtttca    29700
ccgtgttagt caggatggtt tcgatctcct gatctcatga tccacccgcc tcggcttccc    29760
aaagtgctga gattacaggc atgagccact gcgcccggcc aagatgatgg ttttcattt    29820 gtgcctgctg agtctggcaa cctccagcca gacacattca gtgggtggtt agaaatatgg    29880
tcctagagat tagaaaagaa gctaaaaatt ggaaatccac attgtagtca tttctgtgta    29940
gttggtagtg aggctgtaga aatagcctct tcctatgctg tagatgggcc tgttcctatg    30000
ctggttgagt tcttacggtg agcttctatt ggctgtagta gagaagagac ggccactaca    30060
caccagcatt taatgatagg gagagttagg gggcccagca aagagcactg agagtgagac    30120
cttccagaag acccagaagc taagaaacag ggggtctcag taagggagcg tcaggaatca    30180
gatgcagaag agtccctgat taagttgggg aagaatcccc tggctctgac cattagatgc    30240
cattgtttca tcatttcact gagacagtgg agagaaagat gaaaccctgt tttcagtgag   30300
acgaaaaggg agtgagggtg aggaggggca tggggagcta ggcattgagg tgggaaataa    30360
atggtgatac ttagattaag atgggccagg ggagctttta atgtaaggct cacacctgta    30420
atcccagcac tttgggagac caaggcaggc gatcacttga ggccacgagt tcaagaccag    30480
cctggccaac atagtgaaac tccatctcta ctaaaaatac aaaaaattag ctgggtatgt    30540
tggtacacac ctataatccc agctacttgg gaggctgagg catgagaatc actagaaccc    30600
aggaggtgga ggttgcagtg agccaagata atgacactgc attccagcct gggtgacaga    30660
gggagactct gcctctaaag aagaaaaaat ttctttttaa agattatatt ggtcaggagc    30720
ggtggctcac acctgtagtc ccagcacttt gggagaccag ggtaggtaga tcacttgagc    30780
ccggaagttt gagaccagcc tgggcaacat ggcaaaaccc catctctaca aaaaaaaaa    30840 ctttaaaaat tagctggttg tggtaacgtg ccttagctac ttgggaggct gagatgagag    30900
gatcacctga gcctagagag gtggaggttg cagtaagcca ttattgtgct actgcactcc    30960
agcctgggca acagagtgag atgctgtttc aaaaaaaaaa aaaatttttt ttgtttaagg    31020
agaggcttaa ctataatcta tagagaagaa tctagtccag aggaaagagt tgaagatcct    31080
tgctaattga ggaagcaaag gtttggacag cagaaaaaga gaggggctc ctgagccaag     31140 ggcaggggt ccatcccggg gatgaccatg atcccctga gacttctatt agtgtggagg       31200
caggtgaaga tcggcttgtg agtggaagtc tgagctgaaa ggggttcttg ctgatgacct    31260
ctcattttgc ttttggagaa atttacaccg aggaggaggt aaaatgagag acttggggaa    31320
ggtagagaag gtggggagag ttgcctccgg acctggaaag agtgggccaa gggtgaggga    31380
aaggatgcga ggaggccccg tagtgttggt ggcacctggg ctgcaggtgc caggatttgt    31440
ttttctgaca ggctggtgaa gacagcaaca gcaaggggag agggcaagca acctgaaaca    31500
ggcacccaag aatgggggaa atattctgtt ctggggtcat ttttgcaggc cctaccctct   31560
gcagtcccgt gtgtctcgag cccctgagga catcactata ttctgaaatt acataatgat    31620
```

```
gctggtattg acagctgagt cattgaggaa gtgtagactg tgtcccatgg actctgttta     31680
aggaggccag gaagttagca gtaaatacat tgaagacaaa tttccatcca aaaaaggcgg     31740
ggcacagtgg ctcacacctg ttatcccagg actctgggag gccgaagtga gcagatcact     31800
tgaggtcagg agttcgagac caccagcctg gccaacatgg ccaaccctgt ctctactaaa     31860
aatacaaaaa ttagctgggt gtggtgggat gtgcctgtag tcccagctac tcgggaggcc     31920
aagacaggag aacctgagag gcggaggcta cggtgagccg agattgcacc actgcactcc     31980
agcctgactg acaaagcgag actccattgc aaaaaaaaaa aaaaattaca tccagaatga     32040
tgaaaagaat tgatgcttca aggtgacgat ccttagcttc tgggatcatg gcttcattca     32100
ggaccttgct gggggtgtgt ggagagggggc tcttggaagg aaggaatgtc ctctgtagag     32160
agcaggaacc ctgccgttct ctcgctgctg agcatctgga acgcagtagg tgctcagtaa     32220
acagctgcct aaggagtgac tgaatgagga tcacagcccc cagggtactc tcctgttcgg     32280
tagcctctgt ttcccaagga agaataggac ggtctctcag cagcccgtct agcatccgtt     32340
atggtgttct cacgttcatg ttgtccttat gtaaccttga gtttcgggta gtgcttttat     32400
tctaaaagcg ttttcacatc tgtgacctca tttcatcttc agagcaactc tggggtggct     32460
gagtgcatga ccctgtcctg ggcatggtat cggtgccagg actgtgggag gcgcagagga     32520
tctgggctgg ggctcatagc ctgtctgttt ggtttctagc aacgatccac ggtggcatcc     32580
atgatgcatc gtcaggagac tgtggagtgt ttgcgcaagt tcaatgcccg gagaaaactg     32640
aaggtgagtg tcgtttctag gctgccagcc tccttgacat catgccttgc accagtgtgg     32700
ctcctgcccc atttcagaag gaagctcccc tcctggctgg agctgggctc tgaaggttgt     32760
acatgtcaca ggggaggggg cccagaggcc tgatgtcttc aggctctagc caggacctgc     32820
ctttgcctga gaccagcctg ccctttttcta gggtctcagt gaattcacag gaccttcctc     32880
tttccccagg gtgccatcct cacgaccatg cttgtctcca ggaacttctc aggtatgttt     32940
tcccagctgt gtactttgat tatgccgagg tgagtggatc aggaatgggc tgttgccatc     33000
ccgggcaccg ctgggtttcc tcggcgtcct gggccacacc ttgaccaggg cgagtgagga     33060
tcctgttttg aggggctgct gctgctgctg agtcctgctc ctgagattca gggggctgga     33120
ctcacatttg tgaattgttt cctagaactt cccaaggagt agcctgccca acttgctatg     33180
taccttgttt ctctggattc ttatttaact ctctgaagac tctcagcact ttacagattt     33240
tagccattct aggatcttgg aggatgtgct gggggaagaa aagagagatg aggtacagtg     33300
agtcttctca attgccaaat tgccaccatt catttgcctg ctgggacgat ctcttacttc     33360
attttgtcca agtggagatg actaatagaa attattccag atgtttaaac cttttgtggc     33420
gacttgtgct taaaatagtc cctgagatac tagctataac agtgaagaaa taagaccag     33480 caggagagag ggaaaggaac ttgcttaaat ttgcataaag aattgggaga ggtgggacca     33540
ataatttgta aatcatactt gacatttatt tttaagatgc aagacactcc actcccctct     33600 tgccccacc ctcacccaa cccctattat tgtttgcctt caattgggaa gcacagtggc     33660
ttttttgtga ggaaaagatt aatgtcgaga ctgaagacag agagggctct gcccagcttg     33720
ccatctcccc cggtcctccc tccctctaac cccttgcctc actgttttgg ttcaagaccc     33780
ccccttctcc ttcccataat aagactccct cccttgcttc ccctctgcac caccatggaa     33840
agggggttgt gtgggagcct aagccaccac tcagtgggag ccacttctga atacccgtcc     33900
tgctgggctc gcctgcgctg gctccaggta acgccagggc cttggctgtg aggatgctgc     33960
aggcagggag cctagggctt cgtggtgtag cctgagagcc atggagctcc ggaaggccag     34020
```

```
ggctggatag tgagcccggg gctggtggtg ccctgcccta ggccttctcc tttgaccctg   34080
gtttggggct tgatcttgtg tcatgggtac ccacgacggg catactgtgg tgtggctcca   34140
cctctcgcag atgggaacag ggaagcgtgg ctggctgcct ccggtggagt tgcaactgta   34200
gtcccacact tgcttcttgt gctttaatga cgcagcttct acttttgggg tctacgagcc   34260
tttccagagg acattgaagg gcgtttcggt gttgccccta gagcgaagct ctgtcctctc   34320
tcccctctga gttgaagaaa tgtgaagaca gtctgctgct tctcttttag cccagccagt   34380
caatagcaag ggccctgtct tgcagccccg ggcctccaca tcagcctccc cctccatttc   34440
aggaaactgg catcctggtt tcaggaaatc gggtgttagg acaaagcatt ttattcatcc   34500
ctgtagagcc tcctgttctt attggccaga cctagactgg cctttgagct cactttgcct   34560
tgggtcagag gagacaaaca atgttgcaag cattccagga tggcctcttc tgccctgact   34620
ctgggacagg tgaggacaga gtctgtccgg aagcttctgc agaaagaggt gtctatggat   34680
gcaatcaaga aggaagggca cctgtgtgtt tctctagggc tgttttttga gttgacctcc   34740
aataggagat gtggcttatc ctggactcta gcagtttggc taacagcgaa tcggggcctc   34800
cagagtgtat tgcttcagca gcctttgttt tctttctcag ggtttatttc ttgggcacct   34860
ttcacctcag cacactgtga cacacagact gagaatgctg cctctctcgg ctacctccct   34920
taagacaggg acctgtgtct ctgaggggtt gggggggcatg gagctggggc ccaccagtaa   34980
acttagctgc acaagggcca cagaccctcc ctgggacccc cacgccagtc cctctagtgt   35040
gtgggatgta gagaggggag agggctgctc tgcgcccccg gcactctcat cgtgggctca   35100
tttagcttct agggagggaa ggactagaag ggagggcgtt tcatcacagc cttaagctag   35160
ggccgggcta cctcagaagg ggcacctgcc tctcaccggc tcaggcattt cgctgtggac   35220
cctcctccgg aggggtcat gagacaggca ctgcagccct ctccatctgg tggggacgca   35280
gtgttcccta tgccctggcc cagcccggtc ttcccaggcc cccagactgc tgcagggctg   35340
gctgcgccta cctcctcagc ctgccctgg cgctccgctc cccagctcg gctggcttgg   35400 ccacgccgcc tgggctgcgc ctcgcgctgg ggcatgctcg ctgctgacgg cccgtggct   35460 ttgcggggct ctgtgcactg agagactgta tcccctcagt tggcaggcag agctccgccc   35520
ccgcctcgcc tgccgcgagc gccgccggcc tggccgggca aggtacgtgg catgagtcct   35580
ccccgaccgc ctgcctcggc ccctgccac cccaccagga gggccagcat gccgggccca   35640
ctcaccaggg aggcgagtcc catgcttgcg ggctgagatg ggcatgccag acagactacc   35700
taacttggca tctgcaagcg catcgttgtt atggagcccc ctaaccagcc atgcatgctg   35760
ggcgcttgcc aactttcagg gggcagtagc ctggggcat ggagctgggc agcgggagcc   35820
ttgccaagag cccgatgccc tggagggct gcagccaaca gtgggccctc agagacagtg   35880
ctgggcattg ccctgagctg cccggtgcta ggactagatt tccgcagcac tgtttaagac   35940
cccacagagg agccgcgctc ctcaaaattg tgaagtctgg cgcttgctgg cctccaggtc   36000 tgaaggctc cagagtgcag aagcctcaga gccagctgtt tctgggttca catcctagcc   36060
ctgccacacc ctgagcgagt cacaccagct ctcccagcct taattcctca cctctccaat   36120
ggggatgata aataacatgg tggtgcttaa gatcaccctg tcgaaggctc tcagccctgc   36180
ctgtgcagta cagctgttac ctgggagctc gtaagaagtc ctaatgccag gaccccaccc   36240
cagacaataa aatcagaccc ttagggataa gataggtagt acgctttttt taagctccca   36300
ggtgatccta gtgggcaacc agcgttgaga gctggctggt gaatggaaag cacttagaca   36360
```

-continued

```
gtaggcggtc aggcacagga gtcagcacat ttaaaaaaca acattcaaac ccagcacgac   36420
aagataagat caaaggtctt tttctggagt cagaattctc gtaatggaag gacccctgtt   36480
ctcactggag agagatggaa cacagcttgg ggaggaatgg ctacccaaag ggcaggaggg   36540
tggcagcaat agtgacaacg atggtggaca cttactcagt acttgctata tgccaggcac   36600
tctaagtgct tttcatgcat aatcccactg gattcccacc actgttttgt gatgtcagcc   36660
ctactttatc ccattttata gataaagaaa ttgaggctca gagaggttaa gtaactcacc   36720
aaaggtcaca cagctggcaa gtggtggaac caagatacag acccagggca ggcagtccag   36780
gtgtatcaga cagttgggct gattccatct ccctgtgcct cccagactct cctccccact   36840
gtctgctacc ttcctgtggc cttttgtggc cagctggtgt caccagcctt ctggcacaga   36900
gctcatcagc ctggagcgtc accctatgcc tggctagaat ctgtttgaca gctcattatt   36960
ctgccgagtc cttcctgctc acaggtccag agagtggaca ctggggaaag ggtggcagct   37020
aggacccagt gaacctggtg aggacctgct cagtgaaggc ttcaaccccc tggcaaaacc   37080
ctcctgtagg tggtcctggt ttctgtgtct gtgtctgtct gtcctctggt ctcctgtgtg   37140
aactgtgaca ctctgcttct tgagaacact caggagatgt cttgcatcct tgcagtttgg   37200
ccatccagag aacttccatg gcacctaggg atggagccct cactctttca ccctggcact   37260
ctgcttccag gcctgggtgg aagctgtcaa aggcagagtc cccagtgccc caggcggctc   37320
cagtactgag catggtttct cctctaagtg tcgtgcatcc atgccctcct ccacgcagag   37380
gagatcctga ggtgccaccc tgagggtctct gacgccactc aagatcccct tcttgctgag   37440
aggctatagg aagtgcctct tttgggggtt tcgggagacc cttggccccc ttgtcagaca   37500
cagcactctc ttgtggatct ggctgccgga cttcaggttg gggagagggt acaatgcagg   37560
agacttgata ttcctctttg ttttcacagc tgccaaaagc ctattgaaca agaagtcgga   37620
tggcggtgtc aagtaagtg tctccagcct ctgaacagac tggcctcttt ctccccgcag   37680
tcactatggg aattcttggc acctggttcc ccctttccca gggaatcttc ctatccttgc   37740
tagtctgctt taaccagat gcctttgtgc tcagaacaga aggttctgct ggcctgagag   37800
ggaagtaggg aggtatttttt cctggcccta gctggatggg aatgactcag gggaagtgat   37860
ccaaatcata gtttataccca gagctgaatc cggaacctga cttctacacg gatgcttcat   37920
ctccagggct tgactctggg tttttaggt catttggtta tctttctttt tttccttttt   37980
agagcacaaa tcctttttaat caaatgaaag ccaaatttgc ctgagtgatt caggcagggt   38040
atagggcttg gaacctgaaa ccactctcct tttggtcttt ttccttctct ctacaacact   38100
ttcagatccc actgagtgca acagcctcga gctttcttga cgcataggct cctcagaaaa   38160
aggcaaaggc catggtggat cacggcttgt tcccactggg tgagggagct tttcccatgg   38220
gactggggca agaggaggga cctgggaccc accaggagcc ctgctgggaa tggctgcttg   38280
gccaaggtag aggagaggtg actggggcta cccacagggc ccaagacatt ctgtagatgc   38340
tttgggggca gaaaggatcc tggggctagg gcattgggta ggagctcatg ctatcttgaa   38400
gcctcccagc ttacactcta gactagattt tcactgggcc ttttcccaag atcttgtgtc   38460
aacagctgag atacacacac aagccccgtt ccctccccgt tccctcccca ctccctcctc   38520
tttccctcat tctctgcatg cctgcttctg tgttcttccg cccctcgcag gggagcctgg   38580
gctccgcgca caccctctga catggagctg ggggcatcgt gcggtcccca agctctgccc   38640
ctgagctaca tggatggagc caggtgagga aaagggggcag gtttagttgg agagagtgtt   38700
taataagtac ctgtcagtca gatgtccacg cagcattctg ttctgagggg tacacaacag   38760
```

-continued

```
aggtgtaaga gggggtgtgg ctttcagtcg ccataggaag ggggccgcac ctggagtcag    38820
ctgagcgctg ctagtggacc cacgcgagat ggtttagtcc aggaagctca taggagagag    38880
cgtactggag aaagctgcag ggacataggt gagactcact ttgcagtttt actttctgct    38940
atatgttttc tttaaattga aaatatgggt caggcttggt ggctcactcc tgtaatccca    39000
gcactttggg aggctaaggc gggtggatca cctggggtca ggaattcaag accagcctgg    39060
ccaacctggt gaaactccgt ctctacaaaa atacaaaaat tagccagtca taatgaccgg    39120
tgcctgtaat cccagccact cgggagtctg aggcaggaga atggcttgaa cctgggaggc    39180
ggaggttgca gtgagccaag attgcgccat tgcactccag cctgggcgac agagcaagac    39240
tccgtctgaa aataaagaaa agagaaaaga aacaacatg acatttctat aacttaaaaa      39300
caacaaatta tatttgtatg ggttctctta tacatattga tgttctctgc ccagtgagaa    39360
cacagggtgt gtggtagatt gatgtcaaaa atatggttgg atcagtctta tcaggcagaa    39420
ttggaagttt ctgtgtcaga ccatgggaaa taccataggc cattgagcag ggaagctatg    39480
gtgagagtgc tgatagaaat gatttggcaa gccgggtgcg gtggcttcac tcctgtaatc    39540
ccagcatttt gggatgctga ggcaagaaga ttgcttgagt ccaggagttt gagaccagcc    39600
tgggcaaaac cttgtctgtg aaaaaaaaaa aaaaaaatta actgggcata gtggtgtgca    39660
tctgtagtca cagctacttg ggaggctgag gtaagagaat tgcctaagcc cagggagttt    39720
gagcctgagg tgagccaaga tcaagccact gcactctcca gcctgggtga cagtgaaacc    39780
ctgcctcaaa aaaaaaaaaa agatacctgc tgtgcccta gaagttggga aggcaaaact    39840
taatctacct tttaaggtgt ttacagtggg agagacacaa ggcagctact gtttctatgg    39900
agtctgctaa ggtctcaggg aggtgtgcac ctggcaggtg ctgggggagc agacagataa    39960
acatccaaac caggacagga atcttctgga aggagatggc caggaattga gcttgaggga    40020
gtagctggat tttgctgggt taaggaggag acaggagggg agggatattc caggcagagg    40080
gaagagcgca tgtgaagata cacgaggttg aaacagcatg atgattctgg gaacttcagt    40140
atcttcttta tggctgaagg gaagagcaat tgcataaaat gagacctgaa ataaagcagt    40200
gactgttgag gtggagggga gaggatggaa aaggcaccat tacagaacag gtttctagcc    40260
aaactttcta gatactactg gtgtcaaaga tgaaggtcat gtgcagccat gtaagattag    40320
cccaaggagc cagctcaaac catgcacatc cagggcccag cttggaattc atgttctgga    40380
ggccttggct gggaggcaga atctgtgaat tttaaaaaca ctttcatgaa tccaaagcac    40440
atgaaggttt aagagtctgg taaaggcaaa attttggggt tatgtgttaa gaaagggctg    40500
gaacaagagt cggcaaagga aacagaggaa ggacagagag gtagggggaa aagagaaatg    40560
tgcagcagct gcagctcttc caggaaccct gaggatgagg gctgggcaga cacatcatta    40620
ggtaaaggct ttaaatgagg acgtgcgtgg ggaacctagc cctgcaatgt gttgtgtgtc    40680
tgaccctgat atgtgctcag taaatgagtt ttatgccaca ttcttttgag aaaagagctt    40740
caatatcatg gtgggaacca gaggccaatg atcacccaaa attaaaaggc caaccgcgta    40800
ttcgcagccg ttgtgatggg aggggttaat attttttattg aaagagtttc tgtgacaaat    40860
aatccctctt aaaacccagt agaagctggg cgtggtggct cacgcctgta atcccagcac    40920
tttgggaggc cgaggcgggt ggatcacgag gtcaggagat cgagaccatc ctggctaaca    40980
cggtgaaacc ccatctctac tgaaaataca aaaaattagc cgggtgtggt ggcaggcgcc    41040
tgtagtccca gctacttggg aggttgaggc aggagaatgg cgtgaacccg ggaggcggag    41100
```

```
cttgcagtga gctgagattg tgccactgca ctccatcctg ggtgacagag caagactccg   41160
tctcaaaaaa aaaaaaaaaa aaaaaaaaaa acccagtaga taggctaggt gtggtggctc   41220
acatctgtaa tcccagcact ttgggatgct gaggtgggct gatcacttga ggccaggagt   41280
tcgagaccag cctggccaac atggtgaaac cccctctcta ctaaaaatac aaaaagtagc   41340
cagtagtggt ggtgcacgcc tgtagtccca gctactcggg aggctgagat aggagaatca   41400
cttgaacctt gcgggggca gaggttgccg tgagctggga ttacaccact gcactccagc   41460 ctggggaca gagcaagact ctgtctcaaa aaaaaaaaa aggaagatag atgatcaaag    41520
aaaataaact gacaacctga aaacaaggaa gtagaactgg ataacaaatg tggaaaaatt   41580
tctagcctca ctagtatcag agaaatgcaa attgaaacaa ggtgccattt ttggactcta   41640
gttagtgatg gtagtgaaaa ccagaatggt cctttctaaa acagcctgtg tgtcaaaacc   41700
ataaaaatgc ttctacctct ttttaccctg ttaattctac ttctgagagt ttttcctaaa   41760
gaaataattc aaaataggaa aaagctaaaa gcagaaaaat gttgaacatg acattattta   41820
tagctgtgga aagattggag gctgggcaca gtggcttatg cttgtaatct cagcactttg   41880
tgaggccaag ttgggaggat tgcttgaacc caagagcttg agaccagcct gggaaacgta   41940
gtgagacccc atctcttaaa aaaaaaaaa aaaattagct gagtgtggtg aacgtgcct    42000 gtagtcccag ctacttggga ggctgaggtg ggaggattgc ttgagcccag gaggctgagg   42060
ttacagccag gatcacacca ctgcgctcca gcctgggtga cagagtgagg ctctgtttaa   42120
aaaaaaaaaa aaagagaga gaagaaaaaa aagattggag acaatttgaa aagccagtaa   42180
ggagccagac acagtggtgc gtacctatag tcccagctac tcaggaggct gtcgcaggac   42240
agaattgctt gagcccagga attcgaggcc agctgggcaa catagtgaga cccccaactc   42300
ttaaaaatgt ttttaaattt aaaataaaa agatttttta aaagccagta atgactaaa    42360 taattatggg aaatctactt aataaactat tcaaagtta ttaattttca tgaccgtagg    42420
gatattttaa gtgaaaaata aagtgcagaa atgttttata ttaagtgaag gaagtggtat   42480
ataaaggagt acagacaagc caggcacggt ggctcacgcc tgtaatccca gcactttggg   42540
agcccgaggc agacagatca cgaggtcagg agatcgagac cagcctggcc aacatggtga   42600
aaccccgtct tactaaaaa tacaaaaatt agctgggcgt ggtggtgcgt gcctgtaatc   42660
ccagccactt ggaaggctga ggcaggagaa tcgtttgaac tagggagtcg gaggttgcgg   42720
tgagccaagt gcgccactgc actccagcct ggtgacagag caagattctg tctcaaaaaa   42780
taaaaaaaaa aaggagtaca tacactatca ttctaaattt ggtttgaaga aacgtgtttg   42840
tagatattta ttcagtatat aatatgtgga taaaaaggg actggaagaa agcccactaa    42900
gtgtcaacag taacttcacc aggtgatggg aatttgagaa acttttttgc ttacacattt   42960
ttctgtattc ctatattttt catctagatt gtgcactact gttatcagaa ttttttttaa   43020
atactatttt tttttaaag taaagcataa taccaggtgt ggcaactcat gcctggtaat    43080
cccagctact gggaggctga ggtgggagga ttgcttgagc ccaggaggtt cagcctgggc   43140
aacataagca agactccatc tcaattaaaa aaaaagaaa agaggtaaga catgtgcttg    43200
tattattata tcttataatg atatcttttt ttttgttttt tgagacaggg tctcactctg   43260
tccccctggc tggagtgtag tggtgtgatc ttggctcact gcaacctccg cctcccgggc   43320
tcaagtgatt cttccacctc agcctcctga gtagctggga atacgggcat gtgccaccac   43380
gcccggctga ttttttgtatt tttagtagag acggggttgc ccaggctagt cttgaactcc   43440
tgagctcagg tgatctgccc gcctcaacct cctgaagtgc gggggttaca ggcatgagcc   43500
```

```
accacgcctg gcctataatg atatcttaaa agattgcttt cttttttttt tttttttttt    43560
ttttttagac ggagtctcac tctcacccag gctggagtgc aatggcatgg tcttggctca    43620
ctgcaacctc cgcctcccgg gttcaaacaa ttctccaacc tcagcctccc aagtagctgg    43680
gactacaggc gcgtgccacc acacccagct aattttttata ttttttagtag agacggggtt    43740 ttgctatgtt ggccaggctg gtctcgatct cctgaccttg tgatccaccc gcctcagcct    43800
cccaaagtgc tgggattaca ggcatgaacc accgtgcccg gccaattgca ttttttaaaa    43860
agactggaag attgctagga gtattagtgg ttttcccatg ccccttctct gttttccaaa    43920
ttgcttgtat tgtggctgca gtcctttat aatatgaaac aggtaaataa caacttatgt    43980
tgtggctgca tcaaggggt gagaaacgaa aaggagagga caaagcaaga tgtgcagagt    44040
tcgacctttc caggctctct caaagtcaag gttttgatca atgttatgag ggaggcctgt    44100
gaagtagctc agatggtctt gagctttcag catcatggat tcttctttta gatcccatct    44160
tcccttccca actccccctt cctcaattcc tactgcttaa gtgtccatag ggcgatttct    44220
ttttcactgt tcagaagctt tctgcaagat gttcaaaata ctagcattgg tttgagcagc    44280
tagtctgtct tgtgttcttg atttgggga cttagcttct atttagattt ctttgaagct    44340
ggatgccagt gacccaggggt ctatggaaga gtaagagcca cttgtgagga tgactgaaga    44400
ggccacaaac tctcagatcc tgagagtgta ggacaacttg tgccttctgc tagtcccagg    44460
ccagaatggc catcctatct ttaaaaaaga aagcaagcaa gaaaaacgaa aggttatagt    44520
tatttcccta agtactattt gaattatttt gttaaattaa gtatgagaaa gaggtttgaa    44580
cgcttttcca gcttaaaatt taaaataaat atacagttttt taagtaaaag tgagatatga    44640
ttctttagaa atcatctggc atttagccag gcatggtggt gtgcacctgt agtcctagct    44700
actcaggtgg ctgaggcagg aagatccctt gagcccagga ggttgaggct gcagtgagcc    44760
atgatcatgc cagtacttca gcccgggcaa tagagcaaga ccttatctct aaaaaaataa    44820
taaaaagacc tcacatttag acaatgtggt agtgtgctgg ttcagaagga gcccagctat    44880
gcatggctaa gggcaaatcc ctgaatggag aaggaaattg aaaaatgttg actaacctga    44940
gaaacagtct ttggaaaagg gtgatctcag gttctcatgc aggacaattt aggaaaaaga    45000
gagcaagcca ggagaaggct gagaacttat tccccattag tcaaaaatct gctttaagtc    45060
aagatcctgc aatggccttt cacaacaagc ccctgaaaat cagcagaaca aagactgggc    45120
ctggtgagtg agtgcctacg cagagttctt gctgccgtga ttcagtgcaa gttagaaacc    45180
tgtgctcttc tttagcctgg ggaaaaacca aagtcagcaa acccagctca actcagcaaa    45240
ctttcgtcgc ctgtatgcta actataaggc atgttgctag gtactgtgga aattgtaaag    45300
acacataaga taggaacctt cctgaaagca gtaacacttt agttgggtaa agggataagg    45360
agatatacac acacacacac acacacacac acacacacac cccactactt atatatatga    45420
atataaggga actccttctt tttgagggat gattttcgaa gtaaaatatc atatttgagc    45480
atatttaaaa ggccactgta aggctgtgtg cggtggctca cgcttgtaat cccagcactt    45540
tgggaggccg aggtaggtgg atcacctgag gtcaggaatt cgagaccagc ctggccaaca    45600
tggcgaaacc agtctctcta ctaaaaatac aaaaaaaat cagtggggcg tggtggcggg    45660
cgcctgtaat cccagccact caggaggcta aggcaggaga attgcttgaa ccagggaggc    45720
ggaggttgca gtgagccgag atggtgccac tgcactccag cctgggcaac agagtgagac    45780
tccctaaaaa taaataaata aataaataaa taaataaata aataaataaa taaaaggcca    45840
```

-continued

| | | | | |
|---|---|---|---|---|
| atgtaaaaga | ggcctaacta | tatttaggtt | tttcttttcc | tttaaatcta attctaaatt | 45900 |
| atggaccatt | gtcaatattt | gtagcctctt | tcgttgatta | taataataat ccctgaaaat | 45960 |
| gccttctaaa | gaatgctggc | cgcttgaggg | caggagcagt | ttatcagctg tgtttacctg | 46020 |
| aaacagccct | cagtgtttgc | tgggcattgt | taaatgaatg | tgcaaaagtt gaacgacaga | 46080 |
| cggacatatt | acaggggggac | cttaccccca | gtgagctaat | gatgacattg ataattaccc | 46140 |
| ttcatttttt | agacacagtc | ttctgggata | tattttcagt | gttccacgtg gtcttcatct | 46200 |
| tgatgcgtct | gtttcacatg | tgaacgtaaa | gttcgtgagc | atctagttga ggctgaggaa | 46260 |
| tcactgcttt | caacattccc | tgtggcttac | atccctgcat | ttttatgatc actgtagttt | 46320 |
| taatcactgg | cactcctgtg | tttctatttt | ccacgaattg | caaaatgcaa taaaaaattc | 46380 |
| aaatattgta | aacaagcatg | gctatactga | caaaggaagg | ccaacattta actgctaggt | 46440 |
| gattttcaaa | agctcagcat | ctttatgtaa | aaagcatagt | agggatgcag cgaagtcaga | 46500 |
| agtcaaattt | tattagagct | gaggagagcc | tgtagtagct | tttgctttt ccctggtggc | 46560 |
| tgctcacttg | aatttcagac | agttctagta | atgagagaaa | ataaataaca ttacagggtg | 46620 |
| agctaaccct | atgaacccag | acctgtaaat | ttgtagcaaa | atgatactta acctcacaga | 46680 |
| cttgtgtctt | aatctcctta | agaggctttt | tttgagcaag | gctgagacat ctcagaagat | 46740 |
| actaaatctg | tgtctatgaa | cctgaccaca | aaagagttct | tccctcccag ggtctggagg | 46800 |
| gtgtgagtgc | ctgtcggtcc | gtgtgctgtt | taaccctctg | gtgctggact ccgggtctcc | 46860 |
| ctccgctctt | ttctccctga | tgcagagccc | acactggtgc | gctaacctgc agcgtctctg | 46920 |
| tgcttctctt | cttacctcct | cttcccctt | ctctttccct | cttgctgtgg tgtgtccaga | 46980 |
| aaaggaagtc | gagttccagc | gtgcacctaa | tggtgagcct | tgcctgccca cccatcgccc | 47040 |
| actccatgct | gcctgtgccc | gcctgccagc | cacgcaaacc | tgttctgcca cgtgcgtgtg | 47100 |
| cctcactcat | cctcactgca | tgtctgtgct | gtgtgggcag | gtgtggcctg tcctgccagg | 47160 |
| cgggggccat | tgcccaaggt | cacccagtag | cctaaaaagt | ggacattgga aggggtggta | 47220 |
| cggcaccccc | tgctgtggag | cttggacaga | ccccagcgac | ccagggtagg atgtgaagct | 47280 |
| ggtagggact | tggggcaagc | aagggagaga | ccctcactct | cttgtcaccc agaaggagag | 47340 |
| gccctgcttc | ccaggcatga | ggagctgctt | cctacagact | ggcagctgga gggcaactgt | 47400 |
| gtggtgggca | gaggagctgg | ttgcaggctc | ccacttgtga | gtctcgctct cctggctctg | 47460 |
| cccccgtgca | aatcccattc | tctctagctg | tgcccagtgg | tttattctgc ccacccagcc | 47520 |
| ctcgggggac | agctaactca | tctttctcac | gggacactgg | gcaccaaggg caacacagca | 47580 |
| gcctgagtca | ttatgaaacc | atccattaaa | accagaggtg | ggggccgggc gcgatggctc | 47640 |
| acgcctgtaa | tcctagcact | ttgggaggcc | gaggcgggtg | gatcacaagg tcaggagatc | 47700 |
| aagaccataa | cacggtgaaa | ccctgtctct | actaaaaatg | caaaaaatta gccaggtgtg | 47760 |
| gtggtgggcg | cctgtagtcc | cagctactca | ggaggctgag | gcaggagaat ggcgtgaacc | 47820 |
| caggaggcgg | agcttgcagt | gagccgagat | cgcgccactg | cgctccagcc tgggcgacag | 47880 |
| agctagactc | cgtctcaaaa | aataaataaa | ccagaggtgg | ggccacttgg gtgacatccc | 47940 |
| agccctctgc | aggttttgtg | ggcacccctgg | agtccttgcc | cctgtgagg gtcttggcct | 48000 |
| cagctgggat | ttacaggtag | ggcagccctc | tctaaccaac | cccgaacagg tcagcatcat | 48060 |
| tcactgagct | aggtgggctt | tgcttcttgg | tgggaatgag | agacagcaga gctcccgtga | 48120 |
| gtttagaccc | accgtctcac | tactcctggg | cccctcttc | tctagcctgt cgcagtctgt | 48180 |
| ggagtcttgt | tcagtggagt | cacttggtgc | ctggcttgag | gttccatgcc tagccctggg | 48240 |

```
tttggggatg tctgagccat tgacagcaag ctggcggtgg acggcttcag gtctggtcca   48300
agaggcctcc aggcaagaag taggacagtc aggatgcttt ctgtgtatgt cctaggagag   48360
aagacacaca ttctagctgt cgatgtatca tctgtgccct gtgcagggat ggtagccaca   48420
catttgtctc actgcctatt gaagaacttg caggcatcag gctgctcctc agtggccccc   48480
aaccccactg gaactcagtg agatggagta cgctggttag ggaactatca gaggcaaaga   48540
acatcacatg gatatggctc cctgccctgg agatcagcct tcttcctttc ttccatcttc   48600
cccttgcccc tcccttgctg tgcccctccg tgtaatgttt tgtttgttc gtttgctttt   48660 ggtttttga gatggagtct tgctctgttg cccaggctgg agtgcagtgg tgcaatcttg   48720
gctcactgca atctctgcct cccaggttca agcaattctc ttgtctcagc ctcccgagta   48780
gctgggatta caggcatgtg ccaccatgcc cggctaattt ttgtattttt agtagagacg   48840
gggtttcacc atgttggcca ggctggtctt gaactcctga cctcaggtga tccacccgcc   48900
ttggcctccc aaagtgctga gattacaggt gtgagccacc gtgcccaccc acccaccatg   48960
tagttttgaa aggcaaggag atatccctgg tggtcatggt gctgttggga atgttggcct   49020
gtgtgtggcc tactctgtcc tgggggctgg attctgggac tacagctaca gccccgctgg   49080
gtttcacctg cccctccccg gaacactgcc cttctagctg atcaggccta agatttgtca   49140
gacaaaaagg tgaacagcac agtcctgact ctgctccctg aggtcagtga atgcattttg   49200
tgtctgaaag ggacttccac ccccatcctc tggacaccat ctcttaggcc aggcatactt   49260
ttcttttctc cttcctcttt gtttcaggct tcgagctggt gttgtaagaa ggaaatacag   49320
gtgctgggtt gaaagtgcag caggagactg cccacagata ggggaccaga gtttctgaat   49380
tttgttctgc tttcttataa actaccccc ttttcctgt acagtgggaa gaagatcttg   49440
aacttctttg ggtcaggtgt ggattttgca atgacctggc acctggcata agcagagatt   49500
tctggaggga tgctttaaaa caaggctttg ggctggtccc accttgaggg tgcccccaga   49560
gctaggtctc tgggccccac aaatacttcc tctgatcatc tctctagcca tcgctcccat   49620
ctacacagcg ttatggaggc cacctcaggc ctacctcctc caggccagac caggggcaa   49680 gggaggtctg ggagttgaac ctgagtggcc ttggggactc tggaggaact aaaccatctg   49740
ttttcttgtc tcagccacag agcaacaaca aaaacagtct cgtaagccca gcccaagagc   49800
ccgcgccctt gcagacggcc atggtacctc ctgactacag cttctccgcc tctgaccctg   49860
gctgcctcct gccccttccc tcttcctcct cttgtgcccc ctccctggcc tctggcctg   49920 ttcctttctt ggtccccata gaactgactg cttgtgtgc cgccctgtat gccccttccc   49980
cttcattgtc ccgcctggcc gcgctccatc ccgcatggca gaagtgctgc tcctgctcct   50040
gctcctttcg ctggtggggg gaagagtgat cagggctctc agctgaacct cccaggccca   50100
gcccaggacc cctagtgggt ctgctgtggg ggctgggaag tgagttgct taggaaagga   50160 gagggtagga gctttcttgg gacctgaaca tcagttcttg gaggcccct tgtaaaacct   50220 gcctcagcct ctcctttgca aagccagaaa caggaaagag gctgggtc cccacctctg   50280 gatggtgctg aggtctccag gctcctggag tgcctcatgc tggctaagtt ctctctgggc   50340
tcctccaggt gttctgtgtg ctcttggagg tccctctgct agtggtggct aactagagag   50400
tcagcagggg ggtgactggg aaagagggag aggtgatgtt gcctgctact cccctccttg   50460 cggacccctca taccacgtga cgtggcgcg tggggccagg aactagggaa ggcagaaggc   50520
gggcgcagtg ggcagctctc tgggctcagc ttgctgaggg ggcctcctgt cctggctctt   50580
```

-continued

```
tctgggagac ctcattcttc tgcccatgtt cctgcctcac acattcccg tgatgaacgc    50640
tgtgggcggg gcccggcctg tgccctcagt cccacagctc ctctagtgta cctgccccgt    50700
gggaacccca tgtggaaaga gccctcagaa ctgacaggaa tcaggacag aggcccttgc    50760
tgtcagcctc ctgggcacct gcacctgcca ggcctctctt tcttaccagc ccagtgctgc    50820
tgccaaaatc cagggctatc ccagctgccc ggaccccag ttgagccggg atattttgtc    50880
ttctggagat ggctggtggg caggcctcag tggtcatcat agggtctgcg ggggtcctgg    50940
ggtgcaggtg gggctcctca gggaagagcc atagtctgtc cccaagtcgg aagggtaatc    51000
ttcatcttct ctcacaggag ccacaaacca ctgtggtaca caacgctaca gatgggatca    51060
aggtgagtgg ctcctgagcc tgcctcctgc tttccaggtc agcaggagac aggtgggctg    51120
ggtcccaggg gtctacaggc tgcaccctga ggccaaggtg tttgcagagg ctcagctgaa    51180
ggtagcctgt gcccacagtt gctccatgct gaggaagggc attatacctt acagagctca    51240
ggctttgcag tcagacagac ctggtctgaa tcctggcct gcaccttagt atcctttatc    51300
tgcaaattgg ggatgataat aatagaatct tcctccatat gtcggaagtt taaatgagag    51360
taaacgttca ctgaaaaaat aggcaagagt atctccagac cctggagcgt tctccatggc    51420
ctgacccctt tgtgcccttg atgttttcac cagcattcct gaacatctgt taagcccaga    51480
taccatccat ggctctggct tacagagtg acaagacaaa ttatctgttc aaacggtggg    51540
tgggatggga ggcagataaa aaccaataa gcaaacagat aagataagct gggcaccgtg    51600
gctcacacct gtaatcctca cactttggga ggccaaggtg cgcagatcgc ctgagctcag    51660
gagttagaga ccaccttggg caacatggtg aaaccctgtc tctactaaaa tacaaaaaag    51720
taggcaggtg tggtggcgcg tgcctgtagt cccagctact gggaggctg aggcacgata    51780
attgcttgag cctgggaggt ggaggttgca gtgagctgag atcacgccac tgcactccag    51840
cttgggctac gcagtgagac ttaatctctc aaaaaaaata aataagataa aatctaatgt    51900
caataggtaa tctgaagaaa atggcagaaa gtagagagag gccaggtgc ggtggctcat    51960
gcctgtaatc ctagcacttt gggaggccaa ggcgggcgga tcacttgagg tcaggagttc    52020
aaaaccagcc tggccaacat ggcaaaaccc catctctact aaagatacag aaattacctg    52080
gggatggtgg cacatgcctg taatcccagc tacctgggag gctgaggcag gagaatcgct    52140
tgaacctggg aggcggaggt tgcagtgagc tgaaatcgtg ccactgcact tcagcctggg    52200
cgacagagca agactccatc taaaaaatga aaaacagaaa aacctcacca aactagacag    52260
agagaacagg gccttgaatt aagtagtcag gagagggctt cttttcagga gtgatatctg    52320
agctagaaac tgaatggtgg gtgggaagga ggcagccagg ccagctctga ggctgagtgc    52380
cctaagcaga aggaactgaa gctcagatgt ggcctttgta atcaagcaga gggaagagca    52440
aagtgagacg gggagaacca taggagagtg atgaggttgg agaagcagca gggcctgcta    52500
cagaggccct tgtaggagtt tgcattttct tccagcagca aggagaagct attgggagtt    52560
cttagcagga gtaacagaat ctagttgaca ctttaaaaca ccactctggc ctcatgatca    52620
agaactctag ggaggcccgg gcgtggtggc tcacgcccgt aatccctgca cttttggaagg    52680
ccgaggcgag tggatcagca aggtcagga gctcgagacc agcctggcca acatgatgaa    52740
acccatctc taataaaaat acaaaaatta gccaggcatg gtggcaggca cctgtaatcc    52800
cagctactca ggaggctgag acaggagaat cacttgaacc cgggaggcag aggttgcagt    52860
gagccgagat catgccattg cactccagcc tgtgcaacaa gagcaaaact ctgtttcaaa    52920
aaagaaaaac tctagggagg aggtaagtgt ggaagttagg gagaccatga agctgttatc    52980
```

```
atggttcagg tgtgagatgc tggtggcctg gagtcaggtt gtagctgtgc attggaagtg    53040
aagaggtaag acatggggtt tactttggag gcagaaccag aagattttat tttagattgg    53100
gcgatctgaa tataagggaa aaagagaaag agaaggattg aggatgactc caggttttag    53160
cctgagtaac tgggtagatg gtggcattta ccaactgggg gaagactagg gaggggattt    53220
gggaagagtc agacagccag ggtggaagca gaaccttcca caattcctcc ttgcacctct    53280
tgtaggagca gaaactctgc ttttgttctg ctttgctcct ctggcttcca agggatggag    53340
catatagaaa catgttcttt ttggcctaca gggctccaca gagagctgca acaccaccac    53400
agaagatgag gacctcaaag gtaggtgctg gcccttggag ggggaaggac tccagcagtg    53460
acccaggtac ctgggctcca atggggcacc tgccttttct gtccccagaa ctgggaatgc    53520
tggctcctat gccoctagga gagggcttgg tataaaagct actttccacg agccaagata    53580
tgaggcccct gtctggtgtt gctgagttgg gcaagaggct tctcttcttt gaccccaagt    53640
ctaaaatagc taagctagag attctccagg ggccagggct cagagaactg ttcctgttgc    53700
tgataatgat gtgccatcca agaacagggg tacoccaagt ccctgccgaa gtagcctgta    53760
agtgctatga gtcataaata gagtgaccaa tcactcctgg ttttcctcgg acacagaact    53820
tttggtttta agactgtgat gggccaggag tgctggctca cacctgtaat cccagaact    53880 ttgggagggc cagggcagaa ggattgcttg agaccaggag tttgagacaa gcttgggcaa    53940
catagcaaga ccttgtctct attaaaaaaa aaaaattagg aacaaataaa taggccaggt    54000
gcggtgactc acacctgtaa tccccacact ttgggaggcc gaggcaagtg gatcacttga    54060
ggtcaggagt tcaaaaccag cctggccaac atgatgaaac cccgtctcta ctaaaaatac    54120 aaaaaaggc cgggcgtagt ggctcacgcc tgtaatccca cactttggg aggccaaggt    54180 gggtggatca cctgaaggtc agaagttcaa gaccagcctg ccaacatgg tgaaactcca    54240 tctctactaa aaatataaaa aattagccag gtgtgggca ggtgcctgta atcgtagcta    54300
ctcgggaggc ggaggtggga aatcgcttg aacctgggag gtggaggttg cagtgagccg    54360
agatcacccc attgcactcc agcctgggca acaagagcga aacttcttct caaaaaaaaa    54420
aaaaaaaaaa aaaaaattag ccgggtgtgg tggcggggtc ctgtaatccc agctactcgg    54480
gagactgagg catgaaaatg gcttgaaccc gggaggtgga ggttgcagtg agctgagatt    54540
gcaccactgc actccagcct gggtgacaga gcgagactct gtctcaagaa aaaaaaaaa    54600 aaaaatatat atatatatat atatatatat atatatataa atataaaacc cagatagtcc    54660
tgggaacact gggatgagtt ggtcactcta gtcttaagat tttggcctga atgatggagt    54720
tggaactaat ctgacaaccg tgaggccaca tttggtcatg tcctggtggg cccgtaagga    54780
ccactagcct aagcttgggc ctggctagag tgccagggcg gtgggagggc atggcaggct    54840
ggacccccgg gaatctctgt cctgctcttt gattgggcct cctggaattg ctccctttgc    54900
ctgaattcag taagtgacct tgggccagga catcagaaaa gacagaggaa cactctagga    54960
cagagctggg agagcatgcc ctgggtggca aggggggcacc aaacctttg gaaccaaaaa    55020 aaatagcaga aagctgcgag gaagtgaatc atagtagctc caggcccctg tgagtgaggt    55080
cagatcagtt ttgattccgg cactgctggc aacataggag gcgctgtcac tgctgggctc    55140
tggaccctgt ggcctggccc cctggaacat cttccccggg atcagggtc cttggacagg    55200 ctgttgtaag gctcgtctgg aagccacagc ccaggtctgg gcacctgcct ggtgccctca    55260
gctgggaggc ctctctggca gaggcggcgg cgtgggatgt cgtccagtgt ccacagcagc    55320
```

```
ctgaggcgag gcgtcccctt gccccggctc tacagcgcca tgggctcggg gcctgtctgg   55380
cttgctcgct cacctgcctt gttctgtttg ttttggctgc tctgccttgc cctgccctgc   55440
cctgccctgg ctggctagct gccccgctcc gcactgggaa tggcagctcg gtgcctgaag   55500
gacggagctc ccgggacaga acagccccct ctgcaggcat gcagcccag ccttctctct   55560 gctcctcagc cagtaagtgt gagggaggca cattctggct tccgtctccc tggctcgtcc   55620
tgaagcccct cagggacccc caccacagct gtcagtccca cccacctgcc cgtggtagta   55680
agctctggga gcatggcctc tgctgggggt gggggtaga ctggaggtgc tgttgagacc   55740
aggcaggggc ccctgagtct ggggcccaaa gaaatatgag aagtgtgggt ggaaaaacat   55800
ggcctgggat gagggagta gaaagccccc aggatgtgca gtgggccttg cctcagcgct   55860
gagccaggaa gaagggcaga gtcggaagtc aggtctgtgg gggtgggagt gggatgatgg   55920
ggaaatcgtg acagcgagga actgtgttgg ggatgtagtg cttcctgagt ctcagcataa   55980
cagtattaag agcatggggt cagaggcaag atagatctga gtttaaatcc cagctacact   56040
gccttcaaga gtgtgaagtt taacctccca gagctgcagg ttccttatct gtaatgtgga   56100
aataaaatgg cacgcacctc agagccttgt tagataaaag acaaggcagt aggaagtctt   56160
gatacggtgc ctcgatgggt tatcagtagc tcatcctcat atttctagtt acgtctgtgc   56220
tggaggatgc cttttgtctgc tgcttttcct cccaccatct atccttgcag agtttctaag   56280
cacaaccctc ttcgcccgtg gggcccccagt caggtcatcc agatgggtct ggtgggggttg   56340 gagagggtgt gtgtgttgtg ggtgcacacc tgcctgctgc ttttggaagc cgatcgaact   56400
ccttgcttcc cttaacctgc tgcttgctca cctggagctg tggcctagcg gggctgacgg   56460
ctgtggggcc ccctcctgga tgtgccttg gctgcgctgc cctgtcccaa ctgtgctgct   56520
tggctgtgct ggcccggctg ggccgtggtg gtgctgttct aacgcttgca gttgtcttgc   56580
agccttttgc tcctgtgagg aaagggttgt ggcctggccc cgcccagggc tcgggttagg   56640
atgagcccaa gctcaaccca agctctccct taccctggtg gcagcccctg ctggtagtgg   56700
cattccctat aagagaagcc catgccggca ggacatcacc agctgtccct tggctttgga   56760
tgggttgggg aggaggcctc tggagggcac cacctctgcc tgcctgtcag tctgagccct   56820
gtctggtttt cctgaggaac acgtcctggc aatgagagct ggtgtgaaat gtgcagcttt   56880
cccaagcctc gagaggtaaa tggagcagcc tctctggtac aggctgtccc aagtttttac   56940
agttctggga tcatttctcc cagaaaagcc ctgtggagtt gagcagtggg aagcatccat   57000
cctagggttc tgatggtctt ttggcacccc agccctagct ggattctgct gtcaggctac   57060
ctgtcaccca gggctgggtc ctggccactg aatgagggct acgagtgggg gtggtgattg   57120
agacctgact gagccccttc aggtgagaga agtaaattgg gggtggaagc ggccttattg   57180
ggagatgctt gtgagagagg ctgctcatac aggggagggg ctcacagcat tcacgatgta   57240
ccaggctcct cacctgttaa aggcaagcgt gtttttctgca acctggttgt tgatggaaag   57300
ggaggcaaag gccaagaac cataactaat ggctgggctt caggagaaag tggtcattgt   57360
ctctgcagac tgcagagagg gagacgggag ggaaggtgtg ttcgctcttc ctgccaaggg   57420
ccctagagac agagaagagg gatgtctttg tcataagcga tcacagggga ctcctgagga   57480
ctggggaggg ctctctgtaa cttggaggt tccccagtag gtaaattgat ggatttttct   57540
cccccacagt gcgaaaacag gagatcatta agattacaga acagctgatt gaagccatca   57600
acaatgggga ctttgaggcc tacacgtaag tagagaccca tttttttttg tgacctaagt   57660
catctcccaa ggccttccct gcttccagac aacaattagg accctgggga aagggaggtt   57720
```

```
ggaccttggg caaagtatct gagttaagcc ctctcctaaa ctgggagccc ttccaggtag   57780
attccctgag ctcacccatg gtatcctggc agtgggccga aagcacaggg ctgagtggct   57840
cagcaggcag gcctggaaga tctttgctgt cttgtctggc atggccacag gtagcctgct   57900
gctactggat agacaccgct gataaggaag gaagacaagt cactccatag aagcctgata   57960
ggctgctttt ttttttctcc ctgtaggaag atttgtgatc caggcctcac ttcctttgag   58020
cctgaggccc ttggtaacct cgtggagggg atggatttcc ataagtttta ctttgagaat   58080
cgtgagtggg ttcgtgctgc tgatatactc ctgcctgccc ctttacccct ttgtctctgt   58140
ctcctgctca ccttctcatc ccagttgccc acttttccct tatttgacct tcgtgctgca   58200
ctcctactct gtatgcttgt ccccttgtgc ccgatggtt gtagacaggc acctttgaag   58260
gccctgctcc tgagctccaa gtgccattca ttctgcagct gctttgtggc agtgccagtc   58320
accacaatca agctcactta tttcttgccg ggcgcggtgg cttacgcctg taatcccaac   58380
actttgggag gctgaggctg gcggatcacg aggtcaggag atcgaggcca tcctggctaa   58440
cacggtgaaa ccccatctct actaaaaata caaaaaatta gccgggcttg gtggcagtgc   58500
ctgtagtccc agctactcgg gtggctgagg caggagaatg atgtgaacct gggaggcaga   58560
gcttgcagtg agccaagatc aggccactgc actccagcct gggcaacaga gcaagactcc   58620
atctcaaaaa aaaagaaaaa attatttaag cctcacctct ttccaagacg gattggaagg   58680 aaacccttg agattaggtt gagatgatct cagcacataa gaactaagct ctgtgtctgc   58740
aggtttcaca atagaggaaa ttaaaaccag gataagaatg tgcaaaccag ggcactgttg   58800
gtgatttgcg agatcggaag ttgtggctag aatcttcctg actatggagg aaggcagacg   58860
tcttgtatag ggggtggggt gtacattctg gacagttcgt ggaaaataag gggataagaa   58920
gctgaatcat cacccctcc catctttctc tctgctctat gagaccctcc ccttccttat    58980
ttttatctct tcccacttta tgctgggcct tccctatcct gccctgagtt atagttagtc   59040
actaacttct ccgctggctc ccaccttat cacatctcag ctacatatat aaactctctg    59100
ttatctaagt aattctatta gccagaagca attccagagt ttatattagt actaggaagg   59160
tgtcatgtag cccctgtcta acatttgaat tgaactaaaa tgtgaatctc aataaaagca   59220
acacagtttt cacagcatat gctgataatg gcaatccaac ttcttttgcc ttttccccag   59280
agaatcctgg gaatatcctg agcttggtgc tttgatgatt ctatttcagc tttggtgcct   59340 taaaaaaat tacaaatcaa ttttgaatgg tttaagttca tgattttgtt ctgcagccct    59400
agctaggggt gagccaagcc ttatgaaatc taaactcagc ctaacagaat agaaaatcta   59460
taggctttag ttaagagtca catggtcctg agttcaggtg tgtgatttga gcaaattatt   59520
ccttgagcct atttcctcat cttataatga agaaaatatt atccaccaag aaatacagct   59580
cgggcatgta aaaccccagc acaatgcctg attaaaagcg cagcaggtac tgtcactgtt   59640
acccatcttt ctgttccttt tggataaagg agactaatgt aatgtggcat cctggcctct   59700
ggagggcgtt caggggttcg ggggtggggg gggcggtac ttggagattc tgggagtggt    59760
tgcttgggag atggtaagac ttggaagtgc aggctgggag gaaaatgcag gtgcccaggc   59820
ctgatgtcct cttacctacc ccaccctgcc ctgcagtcct gtccaagaac agcaagccta   59880
tccataccac catcctaaac ccacacgtcc acgtgattgg ggaggacgca gcgtgcatcg   59940
cctacatccg cctcacccag tacatcgacg ggcagggtcg gcctcgcacc agccagtcag   60000
aagagacccg ggtctggcac cgtcgggatg gcaagtggct caatgtccac tatcactgct   60060
```

```
cagggccccc tgccgcaccg ctgcagtgag ctcagccaca ggtgcacctg gttgacgggg    60120 gagagggct  ggaagggcct gggataggtg gggtcagagg aagaagagaa ggctgggagg    60180
tggtcctggg agaggaggtg tgggccgtcc cagaggactg gcaaagcctg gcagaatggt    60240
tgcaataagt tatgcttgga aatcagacag actagggtct ggctccgtga ctccaaattg    60300
gatgacctca gacaggttac ttcccctccc taaactgttt ccttagctgt caagaaaagg    60360
cagagagtgg tgcctacctc atttaatcat tgtgaggatt aagtaagata ctataagtaa    60420
agcacttagt tagtgcttag caaatgggag gcagttttgt atttaagcat tagcttcacc    60480
cactttcccc accttctcag gccgacttgg ccatgtgttt agcgtgctaa agtcgctgga    60540
actcatctgt gtgctcattg tcctctgttc tgttaccaca ttctgtcctg tttgacaggg    60600
gctttaggag attccagccg gaggtccaac cttcgcagcc agtggctctg gagggcctga    60660
gtgacagcgg cagtcctgtt tgtttgaggt ttaaaacaat tcaattacaa aagcggcagc    60720
agccaatgca cgcccctgca tgcagccctc ccgcccgccc ttcgtgtctg tctctgctgt    60780
accgaggtgt tttttacatt taagaaaaaa aaaaagaaa aaaagattgt ttaaaaaaaa    60840
aaggaatcca taccatgatg cgttttaaaa ccaccgacag cccttgggtt ggcaagaagg    60900
caggagtatg tatgaggtcc atcctggcat gagcagtggc tcacccaccg gccttgaaga    60960
ggtgagcttg gcctctctgg tccccatgga cttaggggga ccaggcaaga actctgacag    61020
agctttgggg gccgtgatgt gattgcagct cctgaggtgg cctgcttacc ccaggtctag    61080
gaatgaactt ctttggaact tgcataggcg cctagaatgg ggctgatgag aacatcgtga    61140
ccatcagacc tacttgggag agaacgcaga gctcccagcc tgctgtggag gcagctgaga    61200
agtggtggcc tcaggactga gagcccggac gttgctgtac tgtcttgttt agtgtagaag    61260
ggaagagaat tggtgctgca gaagtgtacc cgccatgaag ccgatgagaa acctcgtgtt    61320
agtctgacat gcactcactc atccatttct ataggatgca caatgcatgt gggccctaat    61380
attgaggcct tatccctgca gctaggaggg ggaggggttg ttgctgcttt gcttcgtgtt    61440
ttcttctaac ctgcaagga gagagccagg ccctggtcag ggctcccgtg ccgcctttgg    61500
cggttctgtt tctgtgctga tctggaccat cttttgtcttg ccttttcacg gtagtggtcc    61560
ccatgctgac cctcatctgg gcctgggccc tctgccaagt gccctgtgg dayatgggagga    61620 gtgaggcagt gggagaagag gtggtggtcg tttctatgca ttcaggctgc ctttggggct    61680
gcctcccttg ttattcttcc ttgctgcacg tccatctctt ttcctgtctt tgagattgac    61740
ctgactgctc tggcaagaag aagaggtgtc cttacagagg cctctttact gaccaactga    61800
agtatagact tactgctgga caatctgcat gggcatcacc cctccccgca tgtaacccaa    61860
aagaggtgtc cagagccaag gcttctacct tcattgtccc tctctgtgct caaggagttc    61920
cattccagga ggaagagatc tataccctaa gcagatagca aagaagataa tggaggagca    61980
attggtcatg gccttggttt ccctcaaaac aacgctgcag atttatctgc acaaacatct    62040
ccacttttgg gggaaaggtg ggtagattcc agttccctgg actaccttca ggaggcacga    62100
gagctgggag aagaggcaaa gctacaggtt tacttgggag ccagctgaga agagagcaga    62160
ctcacaggtg ctggtgcttg gatttagcca ggctcctccg agcacctcat gcatgtccca    62220
gcccctgggc cctagccctt tcctgccctg cagtctgcag tgccagcacg caaatccctt    62280
caccacaggg tttcgttttg ctggcttgaa gacaaatggt cttagaattc attgagaccc    62340
atagcttcat atgctgctc cagccccact tcttagcatt cttactcctc ttctgggggct    62400 aatgtcagca tctatagaca atagactatt aaaaaatcac cttttaaaca agaaacggaa    62460
```

```
ggcatttgat gcagaatttt tgcatgacaa catagaaata atttaaaaat agtgtttgtt    62520
ctgaatgttg gtagaccctt catagctttg ttacaatgaa accttgaact gaaatattt    62580 aataaaataa cctttaaaca gtccattgtg ttactgctgt tggaggttta cggccagagg    62640
cgtagatttt agcagcctgg gttaccaggt tggagagagt acctcctcct actcccttg    62700 ggtacttttg agaataaaac ttcctcatgc ctgtaatccc agtactttgg gaggccgagg    62760
cgggcgaatc acgaggtcag gagttcgaga ccagcctggc taat                    62804
```

<210> SEQ ID NO 4
<211> LENGTH: 556
<212> TYPE: PRT
<213> ORGANISM: Human

<400> SEQUENCE: 4

```
Met Ala Thr Thr Ala Thr Cys Thr Arg Phe Thr Asp Asp Tyr Gln Leu
 1               5                  10                  15

Phe Glu Glu Leu Gly Lys Gly Ala Phe Ser Val Val Arg Arg Cys Val
             20                  25                  30

Lys Lys Thr Ser Thr Gln Glu Tyr Ala Ala Lys Ile Ile Asn Thr Lys
         35                  40                  45

Lys Leu Ser Ala Arg Asp His Gln Lys Leu Glu Arg Glu Ala Arg Ile
     50                  55                  60

Cys Arg Leu Leu Lys His Pro Asn Ile Val Arg Leu His Asp Ser Ile
 65                  70                  75                  80

Ser Glu Glu Gly Phe His Tyr Leu Val Phe Asp Leu Val Thr Gly Gly
                 85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
    290                 295                 300

Leu Thr Thr Met Leu Val Ser Arg Asn Phe Ser Ala Ala Lys Ser Leu
```

-continued

```
305                 310                 315                 320
Leu Asn Lys Lys Ser Asp Gly Gly Val Lys Pro Gln Ser Asn Asn Lys
                325                 330                 335
Asn Ser Leu Val Ser Pro Ala Gln Glu Pro Ala Pro Leu Gln Thr Ala
                340                 345                 350
Met Glu Pro Gln Thr Thr Val Val His Asn Ala Thr Asp Gly Ile Lys
            355                 360                 365
Gly Ser Thr Glu Ser Cys Asn Thr Thr Thr Glu Asp Glu Asp Leu Lys
            370                 375                 380
Ala Ala Pro Leu Arg Thr Gly Asn Gly Ser Ser Val Pro Glu Gly Arg
385                 390                 395                 400
Ser Ser Arg Asp Arg Thr Ala Pro Ser Ala Gly Met Gln Pro Gln Pro
                405                 410                 415
Ser Leu Cys Ser Ser Ala Met Arg Lys Gln Glu Ile Ile Lys Ile Thr
                420                 425                 430
Glu Gln Leu Ile Glu Ala Ile Asn Asn Gly Asp Phe Glu Ala Tyr Thr
            435                 440                 445
Lys Ile Cys Asp Pro Gly Leu Thr Ser Phe Glu Pro Glu Ala Leu Gly
    450                 455                 460
Asn Leu Val Glu Gly Met Asp Phe His Lys Phe Tyr Phe Glu Asn Leu
465                 470                 475                 480
Leu Ser Lys Asn Ser Lys Pro Ile His Thr Thr Ile Leu Asn Pro His
                485                 490                 495
Val His Val Ile Gly Glu Asp Ala Ala Cys Ile Ala Tyr Ile Arg Leu
                500                 505                 510
Thr Gln Tyr Ile Asp Gly Gln Gly Arg Pro Arg Thr Ser Gln Ser Glu
            515                 520                 525
Glu Thr Arg Val Trp His Arg Arg Asp Gly Lys Trp Leu Asn Val His
    530                 535                 540
Tyr His Cys Ser Gly Ala Pro Ala Ala Pro Leu Gln
545                 550                 555
```

NUCLEIC ACID MOLECULES ENCODING HUMAN CALCIUM/CALMODULIN (CAMK) DEPENDENT KINASE PROTEINS

FIELD OF THE INVENTION

The present invention is in the field of kinase proteins that are related to the calcium/calmodulin-dependent protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phogphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast.

The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Calcium/calmodulin-dependent Protein Kinases

The novel human protein, and encoding gene, provided by the present invention is related to the family of calcium/calmodulin-dependent protein kinases, which are serine/threonine kinases. The protein of the present invention shows a particularly high degree of similarity to calcium/calmodulin-dependent protein kinase II (CaM II). CaM II is comprised of alpha, beta, gamma, and delta subunits. Each subunit is encoded by a separate gene and alternatively splice forms of each subunit have been found (Breen et al., *Biochem. Biophys. Res. Commun.* 236 (2), 473–478 (1997)). CaM II exerts important effects on hormones and neurotransmitters that utilize calcium as a second messenger. Beta-cell CaM II activity is associated with insulin secretion, and multiple isoforms of CaM II are expressed in human islets of Langerhans (Breen et al., *Biochem. Biophys. Res. Commun.* 236 (2), 473–478 (1997)). It has been suggested that CaM II controls activation-induced cellular differentiation, and is important for imparting antigen-dependent memory to T cells (Bui et al., *Cell* 100: 457–467, 2000). For a further review of CaM II, see Li et al., *Cytogenet. Cell Genet.* 66: 113–116, 1994.

Kinase proteins, particularly members of the calcium/calmodulin-dependent protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the calcium/calmodulin-dependent protein kinase subfamily.

SUMMARY OF THE INVENTION

The present invention is based in part on the identification of amino acid sequences of human kinase peptides and proteins that are related to the calcium/calmodulin-dependent protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain.

FIG. 2 provides the predicted amino acid sequence of tle kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 16 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the calcium/calmodulin-dependent protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the calcium/calmodulin-dependent protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the calcium/calmodulin-dependent protein kinase subfamily and the expression pattern observed. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known calcium/calmodulin-dependent protein kinase family or subfamily of kinase proteins.

Specific Embodiments

Peptide Molecules

The present invention provides nucleic acid sequences that encode protein molecules that have been identified as being members of the kinase family of proteins and are related to the calcium/calmodulin-dependent protein kinase subfamily (protein a sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. For example, a nucleic acid molecule encoding the kinase peptide is cloned into an expression vector, the expression vector introduced into a host cell and the protein expressed in the host cell, The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcrip/cDNA nucleic acid sequences shown in FIG. 1 (SEQ ID NO:1) and the genomic sequences provided in FIG.

3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5 or 6. In yet another preferred embodiment, the percent identity between two nucleotide sequences is determined using the GAP program in the GCG software package (Devereux, J., et al., Nucleic Acids Res. 12(1):387 (1984)) (available at http://www.gcg.com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50 wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 10 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genonic information provided in FIG. 3, such as the genomic sequence mapped to the reference human. The gene encoding the novel kinase protein of the present invention is located on a genome component that has been mapped to human chromosome 10 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 16 different nucleotide positions. Some of these SNPs, which are located 5' of the ORF and in introns, may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which tle mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain. A large percentage of pharmaceutical agents are being developed that modulate the activity of kinase proteins, particularly members of the calcium/calmodulin-dependent protein kinase subfamily (see Background of the Invention). The structural and functional infonnation provided in the Background and Figures provide specific and substantial uses for the molecules of the present invention, particularly in combination with the expression information provided in FIG. 1. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain, Such uses can readily be determined using the information provided herein, that which is known in the art, and routine experimentation.

The proteins of the present invention (including variants and fragments that may have been disclosed prior to the present invention) are useful for biological assays related to kinases that are related to members of the calcium/calmodulin-dependent protein kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerydirin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3 both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3, Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 10 (as indicated in FIG. 3), which is supported by multiple lines of evidence, such as STS and BAC map data.

FIG. 3 provides information on SNPs that have been found in the gene encoding the kinase protein of the present invention. SNPs were identified at 16 different nucleotide positions. Some of these SNPs, which are located 5' of the ORF and in introns, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 16 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determing the chromosomal positions of the nucleic acid molecules by means of in situ hybridization methods. The gene encoding the novel kinase protein of the present invention is located on a genome component that has been mapped to human chromosome 10 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in the placenta, breast (including mammary adenocarcinoma), skin melanotic melanoma, ovary adenocarcinoma, uterus leiomyosarcoma, Burkitt's lymphoma (lymph), duodenal adenocarcinoma (small intestine), and fetal brain.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 16 different nucleotide positions. Some of these SNPs, which are located 5' of the ORF and in introns, may affect control/regulatory elements. The gene encoding the novel kinase protein of the present invention is located on a genome component that has been mapped to human chromosome 10 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 16 different nucleotide positions. Some of these SNPs, which are located 5' of the ORF and in introns, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that the kinase proteins of the present invention are expressed in humans in the placenta, breast (including mammary adenocarcinoma), skin melanotic melanoma, ovary adenocarcinoma, uterus leiomyosarcoma, Burkitt's lymphoma (lymph), and duodenal adenocarcinoma (small intestine), as indicated by virtual northern blot analysis. In addition, PCR-based tissue screening panels indicate expression in fetal brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the fall length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic ingtruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 16 different nucleotide positions. Some of these SNPs, which are located 5' of the ORF and in introns, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933– 943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be usefull to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed; Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells acontaining expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be farther used to produce non-human transgenic animals. A fransgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from a in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What which is claimed is:

1. An isolated nucleic acid molecule encoding a calcium/calmodulin-dependent protein kinase, wherein the nucleic acid molecule consists of a nucleotide sequence selected from the group consisting of:
   (a) a nucleotide sequence that encodes a protein comprising the amino acid sequence of SEQ ID NO:2;
   (b) a nucleotide sequence consisting of SEQ ID NO:1; and
   (c) a nucleotide sequence consisting of SEQ ID NO:3.

2. A nucleic acid vector comprising a nucleic acid molecule of claim 1.

3. A host cell containing the vector of claim 2.

4. A process for producing a polypeptide comprising SEQ ID NO:2, the process comprising culturing the host cell of claim 3 under conditions sufficient for the production of said polypeptide, and recovering said polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claims 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 1.

* * * * *